US010156564B1

(12) United States Patent
Chen et al.

(10) Patent No.: US 10,156,564 B1
(45) Date of Patent: Dec. 18, 2018

(54) METHODS OF DETECTING BIOMARKERS OF ENDOPLASMIC RETICULUM (ER) STRESS-ASSOCIATED KIDNEY DISEASES

(71) Applicants: Ying Chen, Fenton, MO (US); Yeawon Kim, Saint Louis, MO (US)

(72) Inventors: Ying Chen, Fenton, MO (US); Yeawon Kim, Saint Louis, MO (US)

(73) Assignee: Washington University, St. Louis, MO (US)

( * ) Notice: Subject to any disclaimer, the term of this patent is extended or adjusted under 35 U.S.C. 154(b) by 0 days.

(21) Appl. No.: 15/664,476

(22) Filed: Jul. 31, 2017

Related U.S. Application Data

(60) Provisional application No. 62/369,445, filed on Aug. 1, 2016, provisional application No. 62/369,462, filed on Aug. 1, 2016.

(51) Int. Cl.
*G01N 33/50* (2006.01)
*G01N 33/531* (2006.01)

(52) U.S. Cl.
CPC ....... *G01N 33/531* (2013.01); *G01N 33/5091* (2013.01); *G01N 2800/347* (2013.01)

(58) Field of Classification Search
None
See application file for complete search history.

(56) References Cited

U.S. PATENT DOCUMENTS

| | | | | |
|---|---|---|---|---|
| 2010/0022495 A1* | 1/2010 | Hotamisligil | ........ | A61K 31/397 514/182 |
| 2014/0030735 A1* | 1/2014 | Merali | ............... | G01N 33/6893 435/7.21 |
| 2015/0301058 A1 | 10/2015 | Schettini et al. | | |
| 2016/0015725 A1* | 1/2016 | Chae | .................... | A61K 31/519 514/23 |

OTHER PUBLICATIONS

Van Der Vekiens et al., Human and equine cardiovascular endocrinology: beware to compare, Cardiovascular Endocrinology 2013, vol. 2, No. 4, pp. 67-76. (Year: 2013).*
Torzewski et al., Animal Models of C-Reactive Protein, Hindawl Publishing Corporation, Mediators of Inflammation, vol. 2014, Article ID 683598, 2014, pp. 1-7. (Year: 2014).*
Bando et al., 2004, ORP150/HSP12A protects renal tubular epithelium from ischemia-induced cell death, FASEB J, vol. 18, pp. 1401-1403.
Bek et al., 2006, Expression and function of C/EBP homology protein (GADD153) in podocytes, Am J Pathol, vol. 168, pp. 20-32.
Bernascone et al., 2006, Defective intracellular trafficking of uromodulin mutant isoforms, Traffic, vol. 7, pp. 1567-1579.
Bernascone et al., 2010, A transgenic mouse model for uromodulin-associated kidney diseases shows specific tubulointerstitial damage, urinary concentrating defect and renal failure, Human Molecular Genetics, vol. 19, pp. 2998-3010.
Brunati et al., 2015, The serine protease hepsin mediates urinary secretion and polymerisation of Zona Pellucida domain protein uromodulin, Elife, vol. 4.
Bydash et al., 2011, Acute Kidney Injury and Chronic Kidney Disease: A Work in Progress, Clinical Journal of the American Society of Nephrology, vol. 6, pp. 2555-2557.
Cameron et al., 2011, Transcriptional Profiling of Chondrodysplasia Growth Plate Cartilage Reveals Adaptive ER-Stress Networks That Allow Survival but Disrupt Hypertrophy, PLOS ONE, vol. 6, e24600.
Chen et al., 2013, Laminin beta2 gene missense mutation produces endoplasmic reticulum stress in podocytes, J Am Soc Nephrol, vol. 24, pp. 1223-1233.
CRELD2 Gene from GeneCards obtained from http://www.genecards.org/cgi-bin/carddisp.pl?gene=CRELD2 on Jun. 12, 2016 (14 pages).
Cybulsky et al., 2002, Complement C5b-9 membrane attack complex increases expression of endoplasmic reticulum stress proteins in glomerular epithelial cells, J Biol Chem, vol. 277, pp. 41342-41351.
Cybulsky et al., 2005, Role of the endoplasmic reticulum unfolded protein response in glomerular epithelial cell injury, J Biol Chem, vol. 280, pp. 24396-24403.
Cybulsky et al., 2009, Glomerular epithelial cell injury associated with mutant alpha-actinin-4. Am J Physiol Renal Physiol, vol. 297, F987-995.
Dong et al., 2014, Ischemia/reperfusion-induced CHOP expression promotes apoptosis and impairs renal function recovery: the role of acidosis and GPR4, PLoS One,vol. 9, e110944.
Drozdova et al., 2013. Nephrin missense mutations: induction of endoplasmic reticulum stress and cell surface rescue by reduction in chaperone interactions. Physiol Rep, vol. 1, e00086.
Eckardt et al., 2015, Autosomal dominant tubulointerstitial kidney disease: diagnosis, classification, and management—A KDIGO consensus report, Kidney International, vol. 88, pp. 676-683.
El Karoui et al., 2016, Endoplasmic reticulum stress drives proteinuria-induced kidney lesions via Lipocalin 2, Nature Communications, vol. 7.
Evans et al., 2008, Intrarenal oxygenation: unique challenges and the biophysical basis of homeostasis, Am. J. Physiol. Renal Physiol, vol. 295, F1259-F1270.
Fan et al., 2009. R168H and V165X mutant podocin might induce different degrees of podocyte injury via different molecular mechanisms, Genes to Cells, vol. 14, pp. 1079-1090.
Fedeles et al., 2015, Sec63 and Xbp1 regulate IRE1alpha activity and polycystic disease severity. J Clin Invest, vol. 125, pp. 1955-1967.
Gast et al., 2015. Collagen (COL4A) mutations are the most frequent mutations underlying adult focal segmental glomerulosclerosis, Nephrol Dial Transplant, vol. 31, pp. 961-970.
Gillies et al., 2015. GeneVetter: a web tool for quantitative monogenic assessment of rare diseases, Bioinformatics, vol. 31, pp. 3682-3684.
Glomerular Diseases, National Kidney and Urologic Diseases Information Clearinghouse, NIH Publication No. 14-4358,2014, pp. 1-11 (12 pages).

(Continued)

*Primary Examiner* — Gary Counts

(57) ABSTRACT

Among the various aspects of the present disclosure is the provision of methods of detecting biomarkers of endoplasmic reticulum (ER) stress-associated kidney diseases. Another aspect of the present disclosure provides for a method of treating an endoplasmic reticulum (ER) stress-associated kidney disease in a subject.

21 Claims, 50 Drawing Sheets

Specification includes a Sequence Listing.

(56) References Cited

OTHER PUBLICATIONS

Grimm et al., 2015, The evaluation of tools used to predict the impact of missense variants is hindered by two types of circularity, Human Mutation, vol. 36, pp. 513-523.
Hartley et al., 2013, Armet/Manf and Creld2 are components of a specialized ER stress response provoked by inappropriate formation of disulphide bonds: implications for genetic skeletal diseases, Human Molecular Genetics, vol. 22, pp. 5262-5275.
Heymann et al., 2017, Therapeutics for APOL1 nephropathies: putting out the fire in the podocyte. Nephrol Dial Transplant, vol. 32: i65-i70.
Himmelfarb et al., 2007. Acute kidney injury: changing lexicography, definitions, and epidemiology. Kidney International 71:971-976.
Hinkes et al., 2007, Nephrotic syndrome in the first year of life: two thirds of cases are caused by mutations in 4 genes (NPHS1, NPHS2, WT1, and LAMB2), Pediatrics , vol. 119, e907-919.
HSPA5 Gene from GeneCards obtained from http://www.genecards.org/cgi-bin/carddisp.pl?gene=HSPA5 on Jun. 17, 2016 (5 pages).
Inagi et al., 2014, Proteostasis in endoplasmic reticulum—new mechanisms in kidney disease, Nat Rev Nephrol, vol. 10, pp. 369-378.
Inoki et al, 2011, mTORC1 activation in podocytes is a critical step in the development of diabetic nephropathy in mice, J Clin Invest, vol. 121, pp. 2181-2196.
Johnson et al., 2017, Uromodulin p.Cys147Trp mutation drives kidney disease by activating ER stress and apoptosis. J Clin Invest, vol. 127, pp. 3954-3969.
Kemter et al., 2013, Type of uromodulin mutation and allelic status influence onset and severity of uromodulin-associated kidney disease in mice, Human Molecular Genetics, vol. 22, pp. 4148-4163.
Kim et al., 2016, Mesencephalic Astrocyte-Derived Neurotrophic Factor as a Urine Biomarker for Endoplasmic Reticulum Stress-Related Kidney Diseases, Journal of the American Society of Nephrology, vol. 27, pp. 2974-2982.
Li et al., 2013, Acute kidney injury: global health alert, Kidney International, vol. 83, pp. 372-376.
Liu et al., 2001, Defective nephrin trafficking caused by missense mutations in the NPHS1 gene: insight into the mechanisms of congenital nephrotic syndrome. Hum Mol Genet, vol. 10, pp. 2637-2644.
Lovric et al., 2015, Genetic testing in steroid-resistant nephrotic syndrome: when and how, Nephrol Dial Transplant, Nephrol Dial Transplant, vol. 31, pp. 1802-1813.
Madhusudhan et al., 2015, Defective podocyte insulin sign 5 alling through p85-XBP1 promotes ATF6-dependent maladaptive ER-stress response in diabetic nephropathy, Nature Communications, vol. 6.
Markan et al., 2009, Up regulation of the GRP-78 and GADD-153 and down regulation of Bcl-2 proteins in primary glomerular diseases: a possible involvement of the ER stress pathway in glomerulonephritis. Mol Cell Biochem, vol. 324, pp. 131-138.
Miner et al., 2006, Transgenic isolation of skeletal muscle and kidney defects in laminin beta2 mutant mice: implications for Pierson syndrome, Development, vol. 133, pp. 967-975.
Nundlall et al., 2010, An unfolded protein response is the initial cellular response to the expression of mutant matrilin-3 in a mouse model of multiple epiphyseal dysplasia, Cell Stress Chaperones, vol. 15, pp. 835-849.
Oh-Hashi et al., 2009, CRELD2 is a novel endoplasmic reticulum stress-inducible gene, Biochem Biophys Res Commun, vol. 387,pp. 504-510.
Oh-Hashi et al., 2011, Biosynthesis and secretion of mouse cysteine-rich with EGF-like domains 2, FEBS letters, vol. 585, pp. 2481-2487.
Oh-Hashi et al., 2015, Characterization of the Role of MANF in Regulating the Secretion of CRELD2, Biological & Pharmaceutical Bulletin, vol. 38, pp. 722-731.

Olden et al., 1979, Evidence for role of glycoprotein carbohydrates in membrane transport: specific inhibition by tunicamycin, PNAS, vol. 76, pp. 791-795.
Ortiz et al., 2005, The cysteine-rich with EGF-Like domains 2 (CRELD2) protein interacts with the large cytoplasmic domain of human neuronal nicotinic acetylcholine receptor a4 and b2 subunits, J. Neurochem., vol. 95, pp. 1585-1596.
Panayi et al., 2014, Immunoglobulin heavy-chain-binding protein (BiP): a stress protein that has the potential to be a novel therapy for rheumatoid arthritis, Biochem. Soc. Trans., vol. 42, pp. 1752-1755.
Papazachariou et al., 2014, Frequency of COL4A3/COL4A4 mutations amongst families segregating glomerular microscopic hematuria and evidence for activation of the unfolded protein response. Focal and segmental glomerulosclerosis is a frequent development during ageing. PLoS One, vol. 9, e115015.
Pennica et al., 1987, Identification of Human Uromodulin as the Tamm-Horsfall Urinary Glycoprotein, Science, vol. 236, pp. 83-88.
Pieri et al., 2014, Evidence for Activation of the Unfolded Protein Response in Collagen IV Nephropathies, J Am Soc Nephrol, vol. 25, pp. 260-275.
Rampoldi et al, 2003, Allelism of MCKD, FJHN and GCKD caused by impairment of uromodulin export dynamics, Human Molecular Genetics, vol. 12, pp. 3369-3384.
Rampoldi et al., 2011, the rediscovery of uromodulin (Tamm-Horsfall protein): from tubulointerstitial nephropathy to chronic kidney disease, Kidney International, vol. 80, pp. 338-347.
Ron et al., 2007, Signal integration in the endoplasmic reticulum unfolded protein response, Nat Rev Mol Cell Biol, vol. 8, pp. 519-529.
Rupp et al., 2002, Identification, genomic organization and mRNA expression of CRELD1, the founding member of a unique family of matricellular proteins, Gene, vol. 293, pp. 47-57.
Sampson et al., 2015, Opportunities and Challenges of Genotyping Patients With Nephrotic Syndrome in the Genomic Era, Seminars in nephrology, vol. 35, pp. 212-221.
Sampson et al., 2015, Using Population Genetics to Interrogate the Monogenic Nephrotic Syndrome Diagnosis in a Case Cohort, Journal of the American Society of Nephrology, vol. 27, pp. 1970-1983.
Schaeffer et al., 2014, Protein trafficking defects in inherited kidney diseases, Nephrology Dialysis Transplantation, vol. 29, pp. 33-44.
Schurek t al., 1990, Evidence for a preglomerular oxygen diffusion shunt in rat renal cortex, Am. J. Physiol., vol. 259, F910-F915.
Siew et al., 2011, Biological Markers of Acute Kidney Injury, Journal of the American Society of Nephrology, vol. 22, pp. 810-820.
Singbartl et al., 2012, AKI in the ICU: definition, epidemiology, risk stratification, and outcomes, Kidney International, vol. 81, pp. 819-825.
Tervaert et al., 2010, Pathologic Classification of Diabetic Nephropathy, Journal of the American Society of Nephrology, vol. 21, pp. 556-563.
Thastrup et al., 1990, Thapsigargin, a tumor promoter, discharges intracellular $Ca2+$ stores by specific inhibition of the endoplasmic reticulum $Ca2(+)$-ATPase, PNAS, vol. 87, pp. 2466-2470.
Trautmann et al., 2015, Spectrum of steroid-resistant and congenital nephrotic syndrome in children: the PodoNet registry cohort, Clinical journal of the American Society of Nephrology, vol. 10, pp. 592-600.
Vylet'Al et al., 2006, Alterations of uromodulin biology: A common denominator of the genetically heterogeneous FJHN/MCKD syndrome, Kidney International, vol. 70, pp. 1155-1169.
Welch et al., 2001, Nephron pO2 and renal oxygen usage in the hypertensive rat kidney, Kidney Int., vol. 59, pp. 230-237.
Yang et al., 2014, Ischemia-reperfusion induces renal tubule pyroptosis via the CHOP-caspase-11 pathway, Am J Physiol Renal Physiol, vol. 306, F75-84.
Zinszner et al., 1998, CHOP is implicated in programmed cell death in response to impaired function of the endoplasmic reticulum, Genes Dev, vol. 12, pp. 982-995.

\* cited by examiner

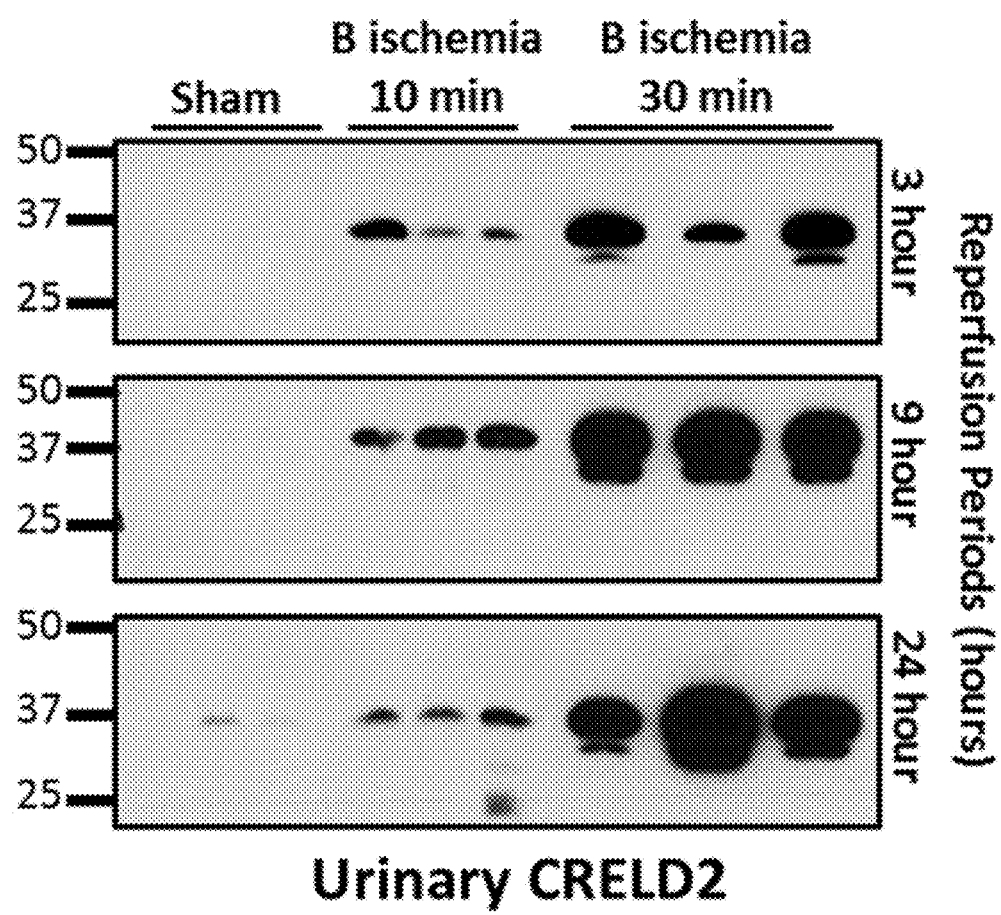

Urinary KIM-1

Urinary NGAL

4x
M: Medulla; G: Glomerulus

40x
M: Medulla; G: Glomerulus

Kidney lysates

Sham mice (n=4)
I/R-injured mice (n=9)

METHODS OF DETECTING BIOMARKERS OF ENDOPLASMIC RETICULUM (ER) STRESS-ASSOCIATED KIDNEY DISEASES

CROSS-REFERENCE TO RELATED APPLICATIONS

This application claims priority from U.S. Provisional Application Ser. No. 62/369,462 filed on 1 Aug. 2016 and U.S. Provisional Application Ser. No. 62/369,445 filed on 1 Aug. 2016, which are incorporated herein by reference in their entirety.

STATEMENT REGARDING FEDERALLY SPONSORED RESEARCH OR DEVELOPMENT

This invention was made with government support under grant numbers DK089015 and DK106451 awarded by National Institutes of Health. The government has certain rights in the invention.

MATERIAL INCORPORATED-BY-REFERENCE

The Sequence Listing, which is a part of the present disclosure, includes a computer readable form comprising nucleotide and/or amino acid sequences of the present invention. The subject matter of the Sequence Listing is incorporated herein by reference in its entirety.

FIELD OF THE INVENTION

The present disclosure generally relates to detection of biomarkers of ER stress in kidneys or detection of an ER-stress associated kidney disease.

SUMMARY OF THE INVENTION

Among the various aspects of the present disclosure is the provision of methods of detecting biomarkers of endoplasmic reticulum (ER) stress-associated kidney diseases.

Another aspect of the present disclosure provides for a method of treating an endoplasmic reticulum (ER) stress-associated kidney disease in a subject.

In some embodiments, the method of detecting or treating an endoplasmic reticulum (ER) stress-associated kidney disease in a subject can include providing a biological sample from a subject suspected of having an endoplasmic reticulum (ER) stress-associated kidney disease; contacting the biological sample with at least one antibody that binds an ER stress biomarker under conditions sufficient for formation of a primary complex comprising the at least one antibody and the ER stress biomarker comprising CRELD2 or BiP if present; measuring a quantity of the primary complex; comparing the quantity of the primary complex to a quantity of a control complex formed from the at least one antibody and a biological sample of an individual who does not have an endoplasmic reticulum (ER) stress-associated kidney disease; or detecting an endoplasmic reticulum (ER) stress-associated kidney disease if the primary complex comprises the ER stress biomarker comprising Cysteine-rich with EGF-like domain protein 2 (CRELD2) or Immunoglobulin binding protein (BiP) at a statistically significant elevated level compared to the control complex.

In some embodiments, the method of detecting or treating an endoplasmic reticulum (ER) stress-associated kidney disease in a subject can include providing a biological sample from a subject suspected of having an endoplasmic reticulum (ER) stress-associated kidney disease; contacting the biological sample with at least one antibody that binds an ER stress biomarker under conditions sufficient for formation of a primary complex comprising the at least one antibody and the ER stress biomarker comprising CRELD2 or BiP if present; measuring a quantity of the primary complex; comparing the quantity of the primary complex to a quantity of a control complex formed from the at least one antibody and a biological sample of an individual who does not have an endoplasmic reticulum (ER) stress-associated kidney disease; detecting an endoplasmic reticulum (ER) stress-associated kidney disease if the primary complex comprises the ER stress biomarker comprising Cysteine-rich with EGF-like domain protein 2 (CRELD2) or Immunoglobulin binding protein (BiP) at a statistically significant elevated level compared to the control complex; or treating the subject by (i) administering a therapeutically effective amount of a pharmaceutical agent suitable for treatment of an ER stress associated disease or (ii) administering a therapeutic method suitable for treatment of an ER stress associated disease.

In some embodiments, the ER stress biomarker comprises BiP and CRELD2.

In some embodiments, the biological sample comprises urine or a kidney tissue sample.

In some embodiments, the ER associated kidney disease, disorder, or condition is selected from one or more of the group consisting of advanced diabetic glomerulosclerosis, autosomal dominant tubulointerstitial kidney disease (ADTKD), acute kidney injury (AKI), acute post-streptococcal glomerulonephritis (PSGN), acute renal failure, Alport syndrome, bacterial endocarditis-caused glomerular disease, chronic kidney disease, congenital nephrotic syndrome (CNS), cyclosporine A treatment induced ER stress, diabetic nephropathy (DN), focal segmental glomerulosclerosis (FSGS), genetic mutations of renal proteins, glomerular disease, glomerular diseases associated with proteinuria, glomerulonephritis, glomerulosclerosis, Goodpasture's syndrome, hereditary nephritis, hereditary proteinuric disease, HIV-associated glomerular disease, infection-related glomerular disease, IgA nephropathy, inflammation induced renal injury, ischemia-reperfusion-induced acute kidney injury or proteinuria, kidney disease associated with missense mutations in nephrin or podocin, kidney disease associated with underglycosylation of nephrin, kidney hypoxia, medullary cystic kidney disease, membranous nephropathy, minimal change disease (MCD), nephrotic syndrome (NS), nodular glomerular sclerosis, osmolar contrast-induced renal injury, protein overload, puromycin aminonucleoside nephrosis (PAN), renal fibrosis, systemic lupus erythematosus (SLE), total kidney failure, tubular disease, tubulointerstitial disease, tunicamycin-induced acute kidney injury or proteinuria, or polycystic kidney disease.

In some embodiments, the method of detecting an endoplasmic reticulum (ER) stress-associated kidney disease in a subject is performed before significant proteinuria or glomerulosclerosis develops.

In some embodiments, the method of detecting or treating an endoplasmic reticulum (ER) stress-associated kidney disease in a subject can include identifying a subject with a high risk for development or progression of proteinuria or renal function deterioration if CRELD2 or BiP levels are statistically significantly elevated compared to a control.

In some embodiments, the at least one antibody is a monoclonal antibody.

In some embodiments, the at least one antibody is a polyclonal antibody.

In some embodiments, the detecting comprises an immunoprecipitation assay, an ELISA, a radioimmunoassay, a Western blot assay, a dip stick assay, or a bead assay.

In some embodiments, the contacting can include contacting the biological sample with a solid surface that binds the ER stress biomarker selected from CRELD2 or BiP if present; and contacting the solid surface with the at least one antibody; or the ER stress biomarker comprises BiP and CRELD2.

In some embodiments, the at least one antibody is bound to a polystyrene bead.

In some embodiments, the method of detecting or treating an endoplasmic reticulum (ER) stress-associated kidney disease in a subject can include contacting a control biological sample from a person not suspected of having an endoplasmic reticulum (ER) stress-associated kidney disease with the at least one antibody that binds CRELD2 or BiP under conditions sufficient for formation of a control complex comprising the at least one antibody and CRELD2 or BiP if present; or measuring the quantity of the control complex.

In some embodiments, the method of detecting or treating an endoplasmic reticulum (ER) stress-associated kidney disease in a subject can include detecting with a Western blot assay or an ELISA.

In some embodiments, the ER stress-associated kidney disease is a hereditary proteinuric disease, human diabetic neuropathy, nephrotic syndrome (NS), acute kidney injury after bypass surgery, or autosomal dominant tubulointerstitial kidney disease (ADTKD).

In some embodiments, the ER stress-associated kidney disease is glomerulosclerosis.

In some embodiments, the glomerulosclerosis is a focal segmental glomerulosclerosis, a familial form of focal segmental glomerulosclerosis, a non-familial form of focal segmental glomerulosclerosis, nodular glomerular sclerosis, or advanced diabetic glomerulosclerosis.

In some embodiments, the ER stress-associated kidney disease is Alport syndrome, membranous nephropathy, acute kidney injury, congenital nephrotic syndrome (CNS), nephrotic syndrome, minimal change disease, human diabetic nephropathy (DN), or medullary cystic kidney disease.

In some embodiments, the ER stress biomarker is detected after a suspected kidney injury; after cardiopulmonary bypass surgery; after treatment of an ER stress associated kidney disease to monitor treatment response or kidney condition or recovery; before diagnosis of an ER associated kidney disease for early detection or risk determination; within 30 minutes, 9 hours, or 24 hours after a suspected kidney injury; or between 0 and 6 hours or up to 2 days after cardiopulmonary bypass surgery.

Other objects and features will be in part apparent and in part pointed out hereinafter.

DESCRIPTION OF THE DRAWINGS

Those of skill in the art will understand that the drawings, described below, are for illustrative purposes only. The drawings are not intended to limit the scope of the present teachings in any way.

FIG. 9A is an image of a Western blot showing mouse primary podocytes were treated with DMSO (control), tunicamycin (TM) (2 µg/ml) or thapsigargin (TG) (1 µM) for 24 h. Cell lysates were analyzed by WB with the indicated antibodies. TM and TG are ER stress inducers.

FIG. 9B is a series of images showing control and TM- or TG-treated mouse podocytes, as described in FIG. 9A stained for CRELD2 (red) and BiP (green). Nuclei were counterstained with Hoechst 33342 (blue). Scale bar, 40 µm.

FIG. 9C is an image of an immunoblot analysis for CRELD2 secretion into the media by cultured primary podocytes described in A (20 µl medium each group).

FIG. 9D is a bar graph showing quantitative real-time PCR analysis of CRELD2 mRNA in primary podocytes from control Lamb2$^{+/-}$, Lamb2$^{-/-}$; Tg-C321R which has podocyte ER stress and control Lamb2$^{-/-}$; Tg-WT mice at P27. CRELD2 expression was normalized as a ratio to mouse podocyte-specific WT-1 mRNA, and the average CRELD2/WT-1 mRNA ratio in Lamb2$^{+/-}$ mice was set as one (n=5 mice per genotype; mean±SD). ***P<0.001 by ANOVA.

FIG. 9E is an image of a Western blot (WB) showing primary podocyte cell lysates from age-matched Lamb2$^{+/-}$, Lamb2$^{-/-}$; Tg-C321R and Lamb2$^{-/-}$; Tg-WT mice at P27 were analyzed by WB with the indicated antibodies.

FIG. 9F is an image of a Western blot (WB) showing Immunoblot analysis for CRELD2 secretion into the media by primary podocytes (20 µl each group) from the indicated genotypes at P27.

FIG. 9G is an image showing urinary CRELD2 excretion was assessed by WB from Lamb2$^{-/-}$; Tg-C321R mice and their Lamb2$^{+/-}$ littermates and age-matched Lamb2$^{-/-}$; Tg-WT mice (n=8, n=8, and n=3, respectively). Shown is one representative experiment at the indicated ages.

FIG. 9H is an image showing Immunoblot analysis of CRELD2 in crude urine specimens from one pair of Lamb2$^{+/-}$ and Lamb2$^{-/-}$; Tg-C321R littermates following the disease course. Shown is one representative experiment. Three more independent experiments were performed with similar results.

FIG. 9I is an image showing CRELD2 excretion in unprocessed urine specimens was detected by WB from Lamb2$^{-/-}$; Tg-C321R mice and their Lamb2$^{+/-}$ littermates and Lamb2$^{-/-}$; Tg-WT mice at 8-16 wks. The urinary CRELD2 excretion was normalized to urine Cr excretion such that the urine volume applied to the gel reflected the amount of urine containing 1 µg of Cr for FIG. 9G-FIG. 9I. All WB images are representative of at least three independent experiments.

FIG. 10A is a bar graph showing quantitative RT-PCR analysis of relative transcript levels of CRELD2 in kidneys at the indicated time points following TM injection (1 mg/kg, IP) as compared to DMSO vehicle-injected controls. Absolute levels were normalized first to those of GAPDH and then to the levels in the control kidneys (mean±SD). P<0.01 and *P<0.001 by ANOVA (n=3 mice per group).

FIG. 10B is a series of images showing dual IF staining for CRELD2 (green) and LTL (red) on paraformaldehyde-fixed, sucrose-cryoprotected kidney sections from mice treated with vehicle or TM (1 mg/kg) at the indicated time points. Nuclei were counterstained with Hoechst 33342 (blue). G: glomerulus. Scale bars, 40 μm.

FIG. 10C is a Western blot showing whole-kidney lysates from mice treated with or without TM (1 mg/kg) at different time points were analyzed by WB for levels of CRELD2 and β-actin.

FIG. 10D is a bar graph showing quantification of CRELD2 normalized to β-actin in kidney lysates in 5 independent experiments. The average CRELD2/β-actin ratio in vehicle-treated mice was set as 1 (mean±SD). *P<0.05 by ANOVA.

FIG. 10E is an image of a Western blot showing the detection of urinary CRELD2 within 1 day of TM injection. Urines were collected for 24 hours after the mice were injected with vehicle or 1 mg/kg TM (IP). Crude urine samples from mice treated with vehicle (n=8) or TM (n=8) were analyzed by WB for CRELD2 excretion. The urinary CRELD2 excretion was normalized to 2 μg of urine Cr excretion.

FIG. 11A-FIG. 11L is a series of images and graphs showing CRELD2 is induced and excreted in urine in a mouse model of AKI caused by bilateral ischemia-reperfusion (I/R).

FIG. 11A is an image of the timeline for the bilateral (B) ischemia-reperfusion model that is based on clamping of bilateral renal vascular pedicles for 30 minutes+reperfusion 3 h/9 h/24 h/3 d/7 d/14 d.

FIG. 11B is a graph demonstrating renal function (serum blood urea nitrogen (BUN)) data that show elevation of BUN at 3 h, peaking of BUN at 24 h and gradually returning to normal renal function at day 14 after ischemic injury.

FIG. 11C is a series of H&E and PAS staining images of paraffin sections from kidneys undergoing sham operation or I/R after 3/9/24 hours and 3/14 days of reperfusion (post-ischemic injury). These images show very mild tubular injury at 3 h, tubular necrosis at 9 h and more severe tubular necrosis at 24 h after ischemic injury. At day-3 post-ischemic injury, tubular recovery was observed, and at day-14 tubular injury resolved.

FIG. 11D is a western blot showing CRELD2 was mildly upregulated in post-ischemic kidneys at 3 hours of reflow compared with sham-operated kidneys. A significant induction at both 9 hours and 24 hours of reflow was observed in kidneys after ischemic injury. CRELD2 expression subsided at day 3 of reflow as compared to that at both 9 hours and 24 hours in post-ischemic kidneys. CRELD2 levels at day 14 became indistinguishable from that in mice undergoing sham surgery.

FIG. 11E is a series of imaging showing that, consistent with WB, dual immunofluorescence (IF) staining of sham-operated and post-ischemic kidney sections for CRELD2 and LTL, which is a marker for proximal tubules, demonstrated that significant CRELD2 induction occurred in injured proximal tubular cells by 9 hours and peaked by 24 hours after the ischemic Injury. In contrast, the glomeruli (G) were devoid of CRELD2 expression.

FIG. 11F is an image of a Western blot showing the levels of urinary CRELD2 excretion after bilateral 30 min ischemia correlate with the AKI severity in the disease course and thus can be used to monitor AKI progression or recovery.

FIG. 11G is a series of images of renal histology (HE and PAS staining) of a bilateral ischemia 10 min model, which causes subclinical renal I/R injury compared to the 30 minute model.

FIG. 11H is a graph showing renal function (serum blood urea nitrogen (BUN)) data comparing the sham and the B/I/R for 10 minutes and 30 minutes.

FIG. 11I is a series of images of Western blots showing urinary CRELD2 excretion was detected as early as 3 h of reperfusion in subclinical renal I/R injury even when post-ischemic kidneys did not show any evidence of kidney function decline or histologic changes. In addition, urinary CRELD2 levels correlated with the severity of the ischemic injury.

FIG. 11J is a bar graph showing relative CRELD2 levels at 3/9/24 h post-ischemic injury for both B ischemia 10 min and 30 min.

FIG. 11K-L are a series of Western blots that compare CRELD2 to two known AKI biomarkers Kim-1 and NGAL.

FIG. 11K is an image of a Western blot of KIM-1. Urinary KIM-1 levels did not correlate with the ischemic injury severity. Data clearly demonstrate the superiority of CRELD2 compared to Kim-1.

FIG. 11L is an image of a Western blot of NGAL. At 3 h of reperfusion, urine NGAL levels did not differ between sham and mice subjected to bilateral ischemia 10 min. Data clearly demonstrated the superiority of CRELD2 compared to NGAL.

FIG. 12A is a series of images showing Masson's trichrome and PAS staining of paraffin kidney sections from ADTKD patients carrying UMOD mutation p.H177-R185del (c-d) or p.W202S (e-f) as well as from normal kidneys after nephrectomy (a-b). Scale bar: 40 μm.

FIG. 12B is a series of representative IF images of human renal biopsies obtained from patients with p.H177-R185del or p.W202S UMOD mutation and from normal kidneys, stained for CRELD2 (green) and uromodulin (red) with a nuclear counterstain (Hoechst 33342, blue). Scale bar: 40 μm.

FIG. 12C-FIG. 12D is a series of images of a Western blots (WBs) showing crude urine samples from human ADTKD-UMOD patients harboring H177-R185del (FIG. 12C) or other disease-causing mutations including C106F, D172H, V93-G97delinsAASC, R178P and G103C (FIG. 12D) as well as from genetically unaffected family members were analyzed by WB for CRELD2 excretion. The urinary CRELD2 excretion was normalized to 10 μg of urine Cr excretion.

FIG. 12E is a series of images showing the same urine samples in FIG. 12C-FIG. 12D analyzed by SDS-PAGE (the urine volume was normalized to 4 μg of urine Cr excretion) and stained with Coomassie G-250. 1.2 μg of BSA was used as a reference for the band density equaling to UACR 300 μg/mg in the urine containing 4 μg of Cr from ADTKD patients. The control and patient numbers listed in FIG. 12C-FIG. 12E corresponded to the same number in TABLE 1.

FIG. 13A is a series of representative images showing H&E and Jones Methenamine Silver staining of paraffin kidney sections from human diabetic nephropathy (DN) patients (n=5) as compared to normal kidneys from nephrectomy samples (n=4). Scale bar: 40 μm.

FIG. 13B is a series of representative images of double IF staining for CRELD2 (green) and podocyte marker synaptopodin (red) with a nuclear counterstain (Hoechst 33342, blue) on formalin-fixed, paraffin-embedded kidney sections from a human patient with DN (patient 3) and normal kidneys (n=4). Scale bar, 40 μm. DN patient showed significant mesangial matrix expansion in kidneys.

FIG. 13C is a series of H&E, Jones Methenamine Silver and Masson's trichrome staining images of paraffin kidney sections from a human early DN patient (patient 6) which did not show any histological change. Scale bar, 40 μm.

FIG. 13D is a series of representative immunofluorescent images of human renal biopsies obtained from early DN or normal kidneys, stained for CRELD2 (green) and synaptopodin (red) with a nuclear counterstain (Hoechst 33342, blue). Scale bar, 30 μm.

FIG. 13E-FIG. 13F is a series of Western blot images showing urinary CRELD2 excretion was assessed by WB from human patients with class III-IV (FIG. 13E) or class I-IIa (FIG. 13F) DN as well as normal controls. The urinary CRELD2 excretion was normalized to 4 μg of urine Cr excretion for FIG. 13E and FIG. 13F. The control and patient numbers listed in FIG. 14E-FIG. 14F corresponded to the same number in TABLE 2.

FIG. 15A shows upregulation of BiP in the podocytes of C321R-LAMB2 transgenic mice (Tg-C321R) compared to BiP expression in the podocytes of control WT-LAMB2 transgenic mice (Tg-WT).

FIG. 15B shows immunodetection of BiP in glomerular lysates.

FIG. 15C shows immunodetection of BiP in primary podocytes.

FIG. 2 23A is a series of images showing, at 24 h of reperfusion, compared with mice with 30 min bilateral ischemia, mice with 10 min bilateral ischemia do not manifest any histological changes.

DETAILED DESCRIPTION OF THE INVENTION

Figure 1:
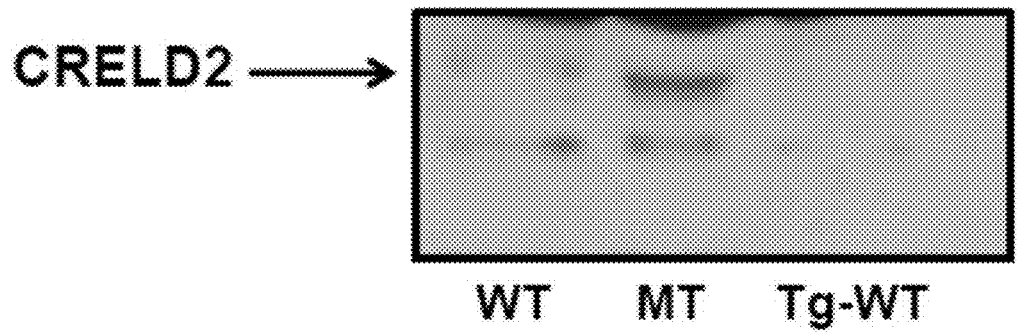
FIG. 1 illustrates immunodetection of increased CRELD2 secretion by ER-stressed C321R podocytes (primary podocyte media).

The present disclosure is based, at least in part, on the discovery that cysteine-rich with EGF-like domain protein 2 (CRELD2) and/or immunoglobulin binding protein (BiP)/glucose-regulated protein (GRP)78 as a urine biomarker for endoplasmic reticulum (ER) stress-related kidney diseases.

Surprisingly, biomarker excretion, concurrent with podocyte or tubular cell ER stress, preceded clinical or histologic manifestations of the corresponding disease.

Endoplasmic Reticulum (ER) Stress Associated Kidney Disease

The methods as described herein can be used in detecting a biomarker before, during, or after the treatment of an ER-stress associated kidney disease. The methods as described herein can be used to detect, diagnose, or monitor an ER-stress associated kidney disease. An ER-associated kidney disease can be any kidney disease, disorder, or condition that is associated with, mediated by, or characterized by endoplasmic reticulum (ER) stress or is preceded by ER stress.

Endoplasmic reticulum (ER) stress in podocytes or renal tubular cells can occur before clinical manifestations of diseases. Early diagnosis and detection of ER stress can be imperative for early therapeutic intervention. Identification of ER stress biomarkers is essential for early diagnosis, proteinuria progression prediction, and treatment response monitoring. Thus, it is imperative to develop noninvasive biomarkers for detecting ER stress in podocytes or tubular cells in the incipient stage of disease, when a kidney biopsy is not yet clinically indicated.

Endoplasmic reticulum (ER) stress and induction of the unfolded protein response have emerged as a signaling platform that underlies the pathogenesis of various glomerular and tubular diseases. Thus, there is an urgent need to identify novel ER stress biomarkers in the early stages of ER stress-mediated kidney disease, when a kidney biopsy is not yet clinically indicated.

Mounting evidence has established the importance of endoplasmic reticulum (ER) stress in the pathogenesis of various glomerular and tubular diseases (1). The ER is the central site for folding, post-translational modifications, and transport of secretory and membrane proteins. A mismatch between the load of unfolded/misfolded proteins and the folding capacity of the ER leads to ER stress (2). The ER responds to stress by activating intracellular signaling pathways, collectively known as the unfolded protein response (UPR), which aligns cellular physiology to the demands imposed by ER stress (2). Dysregulation of the UPR under persistent or intense ER stress eventually results in death of glomerular and/or tubulointerstitial cells.

Nephrotic syndrome (NS), characterized by heavy proteinuria and hypoalbuminemia, is accompanied by an increased risk for infection, venous thromboembolism, and progression to end-stage renal disease (ESRD). Nearly 100% of patients with congenital onset and 44% with infantile onset of NS have podocyte gene mutations and the overall mutation detection rate is as high as 52% in steroid-resistant pediatric NS patients (3). The leading mutated podocyte genes include laminin β2 (LAMB2) causing congenital NS and Pierson syndrome and collagen IV α chain (COL4A) underlying Alport syndrome (AS) and familial focal segmental glomerulosclerosis (FSGS) (4). Emerging evidence has demonstrated that podocyte ER stress may be an important functional link from genetic mutations to disease phenotype in primary NS. It was recently shown that a C321R missense mutation in LAMB2, which encodes an important constituent of the mature glomerular basement membrane (GBM), induces podocyte ER stress and activates the pro-apoptotic C/EBP homologous protein (CHOP) pathway in the development of proteinuria (5). In addition, the G1334E mutation in COL4A3 triggers podocyte ER stress and leads to podocytopathy and AS (6). Multiple studies have also linked podocyte ER stress to the pathogenesis of diverse sporadic nephropathies including FSGS, membranous nephropathy, minimal change disease and diabetic nephropathy (DN) in both experimental models (7-9) and human kidney biopsies (10, 11).

Accumulating evidence has also highlighted a pathogenic role for ER dysfunction and the derangement of ER proteostasis in the onset and progression of renal tubulointerstitial disease, which ultimately advances to ESRD. Autosomal dominant tubulointerstitial kidney disease (ADTKD), due to mutations in the UMOD gene encoding uromodulin, is characterized by gout, alterations in urinary concentration, and progressive loss of kidney function (12, 13). Proteinuria is typically mild or absent. Uromodulin (Tamm-Horsfall protein) is exclusively expressed in the thick ascending limb (TAL) of Henle's loop. Currently more than 50 UMOD mutations have been identified, and most of them are missense mutations (13). In vitro and in vivo studies have shown that all mutations that have been studied cause protein misfolding, ER retention and ER stress activation in TAL cells (14-18). Additionally, tubular ER stress induced by ischemia, albuminuria and nephrotoxins contributes to a variety of acquired forms of tubular injury (19, 20).

Although multiple lines of evidence from clinical and experimental studies have demonstrated that a maladaptive ER response is mechanistically linked to the pathogenesis of glomerular and tubular disorders, the absence of biomarkers for monitoring podocyte or tubular cell ER stress has hampered early detection and effective therapeutic intervention to restore ER homeostasis. Mesencephalic astrocyte-derived neurotrophic factor (MANF) as a urinary ER stress biomarker in mouse models was recently identified (21).

Here, it was investigated if another secreted, ER stress-inducible protein-cysteine-rich with EGF-like domains 2 (CRELD2) is also a candidate urinary ER stress biomarker in both mouse models and human patients.

CRELD2 was recently identified as a novel ER stress-inducible gene through microarray analysis of Neuro2a mouse neuroblastoma cells treated with thapsigargin (TG) (22). It is a ~50 kDa secretory glycoprotein that predominantly localizes to the ER and Golgi apparatus (22, 23). Its promoter region, which is well conserved among various species, contains a typical ER stress response element (ERSE) (CGTGG-N9-ATTGG) that is positively regulated by the ER stress master regulator ATF6 (22). By overexpressing wild-type (WT) and various mutant CRELD2 constructs in HEK293 or COS7 cells, it has been reported that four C-terminal amino acids (REDL) play a crucial role in CRELD2 secretion and that Ig binding protein (BiP) and MANF significantly enhance its secretion (23, 24). However, very few studies have been carried out to characterize the intrinsic induction and secretion of CRELD2 in vitro and in vivo. The only published in vivo study has shown that CRELD2 is upregulated and secreted following ER retention of the mutant cartilage extracellular matrix protein in mouse knock-in models of chondrodysplasia resulting from mutations in matrilin-3 (Matn3) or type X collagen (Col10a1) (25). The function of CRELD2 under pathophysiological conditions remains poorly understood. The aim of this study was to determine whether CRELD2 can serve as an early urinary ER stress biomarker for ER stress-mediated kidney diseases by studying a combination of in vitro and in vivo mouse models as well as human patient samples.

Endoplasmic reticulum (ER) stress refers to physiological or pathological states that result in accumulation of misfolded proteins in the ER. To handle misfolded proteins, the ER has in place quality control mechanisms, including the unfolded protein response and ER-associated degradation (ERAD). Endoplasmic reticulum (ER) stress and disrupted proteostasis contribute to the pathogenesis of a variety of kidney diseases, including glomerular and tubular diseases such as, but without limitation, glomerulonephritis, glomerulosclerosis, tubulointerstitial disease, autosomal dominant tubulointerstitial kidney disease (ADTKD), nodular glomerular sclerosis, advanced diabetic glomerulosclerosis, hereditary proteinuric disease such as congenital nephrotic syndrome (CNS) and focal segmental glomerulosclerosis (FSGS) caused by podocyte gene mutations, membranous nephropathy, infection-related glomerular disease, minimal change disease, diabetic nephropathy, Alport syndrome, acute kidney injury, medullary cystic kidney disease, or polycystic kidney disease.

A tubulointerstitial ER stress response, in some cases associated with tubular cell apoptosis, may occur in glomerular diseases associated with proteinuria, including puromycin aminonucleoside nephrosis, protein overload, and experimental and human diabetic nephropathy. Certain missense mutations in nephrin and podocin, as well as underglycosylation of nephrin, result in misfolding and retention in the ER, and eventually ERAD.

Kidney diseases associated with ER stress can be a chronic kidney disease or hypoxia (e.g., chronic kidney hypoxia, including hypertension and diabetes). Hypoxia is a pathologic condition which is characterized by an insufficient supply of oxygen to meet demand. The blood supply to the kidneys is very large, accounting for roughly 25% of cardiac output. However, owing to the presence of an arteriovenous oxygen shunt in the kidney (Schurek et al., 1990; Welch et al., 2001), no more than 10% of the oxygen delivered through the renal artery is utilized (Evans et al., 2008). Oxygen utilization by the kidney therefore appears to be inefficient, suggesting in turn that the kidney might be particularly susceptible to hypoxia. Chronic hypoxia triggers ER stress. Hypoxia induces cell stress, which leads the production of reactive oxygen species (ROS), a situation termed oxidative stress. ROS are produced in several organelles, including the ER. Altered redox homeostasis in the ER can cause ER stress.

ER stress is evoked in various kidney diseases, including diabetic nephropathy, renal fibrosis, inflammation or osmolar contrast-induced renal injury, ischemia-reperfusion, genetic mutations of renal proteins, proteinuria, or cyclosporine A treatment.

Other glomerular diseases that can be associated with ER stress can be Systemic lupus erythematosus (SLE), Goodpasture's Syndrome, IgA nephropathy, Hereditary Nephritis-Alport Syndrome, Infection-related Glomerular Disease, Acute post-streptococcal glomerulonephritis (PSGN), Bacterial endocarditis-caused glomerular disease, HIV-caused glomerular disease, Sclerotic Diseases, such as Glomerulosclerosis, Diabetic nephropathy or Focal segmental glomerulosclerosis (FSGS), Membranous nephropathy, Minimal change disease (MCD), Acute Renal Failure, Chronic Kidney Disease, Total Kidney Failure, or Nephrotic Syndrome.

Hereditary proteinuric diseases can be genetically heterogeneous disorders and can progress into end stage renal failure. Currently there is no treatment available. In the past two decades, there have been seminal advances in the understanding of the glomerular filtration barrier (GFB) and pathogenesis of proteinuria with major discoveries of podocyte-specific gene mutations in human nephrotic syndrome (NS) patients. The leading mutated genes are NPHS1 encoding nephrin, NPHS2 encoding podocin, WT-1, and LAMB2 encoding laminin β2. However, how the gene mutations cause proteinuria is still largely unknown.

Missense mutations can lead to protein misfolding and disruption of protein trafficking. Alterations in protein trafficking occur mainly in the ER, which is the central site for folding, post-translational modifications, and transport of secretory and membrane proteins. Protein folding is aided by ER-resident molecular chaperones and enzymes, such as BiP/GRP78, calnexin, calreticulin and protein disulfide isomerase. An imbalance between the load of misfolded proteins and the folding capacity of the ER leads to ER stress and the unfolded protein response (UPR).

Misfolded proteins and the resultant ER stress represent an important cause of ER storage diseases including, such as but without limitation, cystic fibrosis, α1-antitrypsin deficiency, retinitis pigmentosa or Alzheimer's disease.

At present, more than 90 different mutations in NPHS1, 100 in NPHS2, 50 in LAMB2 and 500 in COL4 encoding collagen IV have been identified. In cell culture studies it has been found that a few nephrin or podocin missense mutants cause ER stress. Moreover, in animal models, it has been shown that podocyte ER stress is induced in FSGS caused by α-actinin-4 K256E and in Alport syndrome caused by COL4α3 G1334E.

Endoplasmic reticulum (ER) stress and disrupted proteostasis contribute to the pathogenesis of a variety of glomerular and tubular diseases. Previous data demonstrate that podocyte ER stress can be pathogenic and can occur before significant proteinuria and glomerulosclerosis. Thus, podocyte ER stress markers can be important to determine subjects with a high risk for development/progression of proteinuria and renal function deterioration. In addition, early detection and intervention aimed at alleviating podocyte ER stress and restoring ER homeostasis can be less challenging than reversing established podocyte injury. Thus, it is imperative to develop noninvasive biomarkers for detecting ER stress in podocytes or tubular cells in the incipient stage of disease, when a kidney biopsy is not yet clinically indicated. Therefore, identification of ER stress biomarkers is essential for early diagnosis, proteinuria progression prediction, and treatment response monitoring. MANF is an example of a urine biomarker for detecting ER stress (Kim, Y. et al. J Am Soc Nephrol 2016; U.S. patent application Ser. No. 14/730,465, incorporated herein by reference).

ER Stress Biomarkers

The present disclosure provides for the identification of ER stress biomarkers for the early diagnosis, detection, or monitoring of ER-associated kidney disease.

For example, an increase in ER biomarkers can be indicative of or predict the onset of an ER associated disease. As another example, monitoring ER biomarker levels during treatment can be used to monitor disease progression or drug efficacy.

Immunoglobulin Binding Protein (BiP).

Detection of Immunoglobulin binding protein (BiP) as a biomarker for endoplasmic reticulum (ER) stress-associated kidney diseases is disclosed. Elevated BiP levels can be detected in urine and tissue samples from subjects with diseases such as hereditary proteinuric diseases caused by different podocyte gene mutations, familial and non-familial forms of focal segmental glomerulosclerosis, Alport syndrome, membranous nephropathy, acute kidney injury, and medullary cystic kidney disease. Elevated BiP levels can also be detected in urine and kidney tissue in animal models of endoplasmic reticulum (ER) stress-associated kidney disease. BiP levels can provide early signs of developing an ER stress-associated kidney disease. BiP levels can also be measured to monitor progress of treatments of such diseases. BiP levels in a urine or tissue sample can be determined using a monoclonal or a polyclonal antibody.

The present disclosure provides methods of detecting and diagnosing diseases that involve ER stress in podocytes or renal tubular cells. These methods comprise, consist essentially of, or consist of, detecting levels of Immunoglobulin binding protein (BiP) in a biological sample (e.g., urine sample, saliva, blood, plasma, biopsy) from a subject. Immunoglobulin binding protein (BiP) localizes to the ER and is secreted in response to ER stress in several cell types. A diagnosis of an ER stress-associated disease can be made if the level of urinary BiP is statistically greater (e.g., significantly or statistically significantly) than that of a control sample, such as a urine sample from an individual not suspected of having an ER stress-associated disease. In some embodiments, urinary BiP excretion concurrent with podocyte or tubular cell ER stress can precede clinical or histologic manifestations of the corresponding disease. In addition, the inventors detected urinary BiP excretion in human diabetic nephropathy (DN) patients caused by podocyte ER stress, in ADTKD-UMOD and severe ischemic AKI patients caused by tubular ER stress, but not in healthy controls. Thus, BiP can serve as a urine diagnostic or prognostic biomarker in ER stress-associated kidney diseases and can help stratify disease risk, predict disease progression, monitor treatment response, and identify subgroups of patients who can be treated with ER stress modulators. Furthermore, there can be clinical use of BiP as a urine biomarker for ER-stress-associated kidney diseases such as hereditary proteinuric diseases caused by different podocyte gene mutations, familial and non-familial forms of focal segmental glomerulosclerosis, Alport syndrome, membranous nephropathy, acute kidney injury, or medullary cystic kidney disease.

ER stress in podocytes or renal tubular cells can occur before clinical manifestations of diseases. Early diagnosis and detection of ER stress can be imperative for early therapeutic intervention. BiP can be used as a urine biomarker for early diagnosis, predicting disease progression, monitoring treatment response in a variety of kidney diseases and for identifying subgroups of patients who can be treated with ER stress modulators.

BiP is an important ER molecular chaperone that can aid protein folding. Recently it has been found that BiP can be secreted extracellularly in response to ER stress. BiP has not yet been used as an ER stress biomarker in kidney diseases (Panayi, G S et al., Biochem. Soc. Trans. 42: 1752, 2014). ER stress upregulated BiP expression in podocytes and tubular cells. Notably, urinary BiP excretion concurrent with podocyte or tubular cell ER stress preceded clinical or histologic manifestations of the corresponding disease. In addition, without being limited by theory, the present inventors detected urinary BiP excretion in human diabetic nephropathy (DN) patients caused by podocyte ER stress, in ADTKD-UMOD and severe ischemic AKI patients caused by tubular ER stress, but not in healthy controls. Thus, BiP can serve as a urine diagnostic or prognostic biomarker in ER stress-associated kidney diseases to help stratify disease risk, predict disease progression, monitor treatment response, and identify subgroups of patients who can be treated with ER stress modulators in a highly targeted manner. BiP can be used as a clinical urine biomarker for ER-stress-associated kidney diseases including, such as and without limitation, hereditary proteinuric diseases caused by different podocyte gene mutations, familial and non-familial forms of focal segmental glomerulosclerosis, Alport syndrome, membranous nephropathy, acute kidney injury, and medullary cystic kidney disease.

The present disclosure demonstrates in cell, animal models, and human patients that BiP is a useful urine biomarker for ER stress-associated kidney diseases. BiP can be used as a urine biomarker for early diagnosis, predicting disease progression, monitoring treatment response in a variety of kidney diseases and identifying subgroups of patients who can be treated with ER stress modulators in a highly targeted manner. The disclosed methods provide means for identifying subjects at high risk for development or progression of proteinuria and renal function deterioration.

The present teachings demonstrate that podocyte ER stress is pathogenic and occurs before significant proteinuria and glomerulosclerosis. Thus, podocyte ER stress markers are important to determine subjects with a high risk for development/progression of proteinuria and renal function deterioration. In addition, early detection and intervention aimed at alleviating podocyte ER stress and restoring ER homeostasis can be less challenging than reversing established podocyte injury.

BiP has been recently shown to be secreted in response to ER stress. The present inventors have shown that BiP can be induced in ER-stressed podocytes and renal tubular cells, and can be excreted in the urine at very early stage of diseases. The present teachings demonstrate that urinary BiP excretion can be detected in urine samples of human DN patients associated with podocyte ER stress, of ADTKD-UMOD and severe ischemic AKI patients caused by tubular ER stress. The present teachings have important clinical applications for early identification of individuals at risk for disease progression and for following the treatment response. There can be broad clinical uses of BiP as a urine biomarker for ER stress-associated kidney diseases including, such as and without limitation, CNS and FSGS caused by different podocyte gene mutations, Alport syndrome, and acute kidney injury.

Cysteine-Rich with EGF-Like Domain Protein 2 (CRELD2).

Cysteine-rich with EGF-like domains 2 (CRELD2) is a newly identified protein that is induced and secreted under conditions of ER stress. Here, for the first time, CRELD2 as an early mechanistic urinary biomarker for detecting ER stress in podocytes and renal tubular cells in murine models of podocyte ER stress-induced nephrotic syndrome and tunicamycin- or ischemic-reperfusion-induced acute kidney injury is disclosed. It was found that ER stress markedly upregulates CRELD2 expression in podocytes and tubular cells. Importantly, urinary CRELD2 excretion coinciding with podocyte or tubular ER stress can be detected in the incipient stage of the corresponding disease. Furthermore, it was shown that elevations in urinary CRELD2 occur in human patients with diabetic nephropathy, autosomal dominant tubulointerstitial kidney disease (ADTKD) caused by UMOD mutations, a prototypical tubular ER stress disease, and ischemic AKI.

In conclusion, the studies, as described herein, have identified CRELD2 as a novel urinary ER stress biomarker with potential utility in early diagnosis, risk prediction, monitoring treatment responses and developing highly-targeted therapies in the emerging era of precision medicine.

The present disclosure provides for methods of detecting and diagnosing diseases that involve ER stress in podocytes or renal tubular cells. These methods comprise, consist essentially of, or consist of detecting levels of Cysteine-rich with EGF-like domain protein 2 (CRELD2) in a urine sample from a subject. A diagnosis of an ER stress-associated disease can be made if the level of urinary CRELD2 is statistically significantly greater than that of a control sample, such as a urine sample from an individual not suspected of having an ER stress-associated disease. In some embodiments, urinary CRELD2 excretion concurrent with podocyte or tubular cell ER stress can precede clinical or histologic manifestations of the corresponding disease. In addition, the inventors detected urinary CRELD2 excretion in human diabetic nephropathy (DN) patients caused by podocyte ER stress, in ADTKD-UMOD and severe ischemic AKI patients caused by tubular ER stress, but not in healthy controls. Thus, CRELD2 can serve as a urine diagnostic or prognostic biomarker in ER stress-associated kidney diseases and can help stratify disease risk, predict disease progression, monitor treatment response, and identify subgroups of patients who can be treated with ER stress modulators. Furthermore, there can be clinical use of CRELD2 as a urine biomarker for ER-stress-associated kidney diseases such as hereditary proteinuric diseases caused by different podocyte gene mutations, familial and non-familial forms of focal segmental glomerulosclerosis, Alport syndrome, membranous nephropathy, acute kidney injury, and medullary cystic kidney disease.

Cysteine-rich with EGF-like domain protein 2 (CRELD2) is an approximately 60 kDa glycoprotein that contains two EGF-like domains. It is widely expressed in fetal and adult tissues. CRELD2 localizes to the endoplasmic reticulum (ER) and Golgi. It is upregulated during ER stress in several cell types and can also be secreted. CRELD2 has not been studied in the kidney disease yet (Rupp, P. A., et al., Gene, 293, 47, 2002; Ortiz, J. A., et al., J. Neurochem., 95, 1585, 2005; Oh-hashi, K., et al., Biochem. Biophys. Res. Commun., 387, 504, 2009; Oh-hashi, K et al., FEBS Lett. 585, 2481, 2011; Cameron, T L et al., PLOS ONE 6: e24600, 2011; Nundlall, S., et al., Cell Stress Chaperones, 15, 835, 2010.) CRELD2 localizes to the ER and is secreted in response to ER stress in several cell types.

CRELD2 can be used as a urine biomarker for early diagnosis, predicting disease progression, monitoring treatment response in a variety of kidney diseases and for identifying subgroups of patients who can be treated with ER stress modulators.

Detection of CRELD2 as a biomarker for endoplasmic reticulum (ER) stress-associated kidney diseases is disclosed. Elevated CRELD2 levels can be detected in urine and tissue samples from subjects with diseases such as hereditary proteinuric diseases caused by different podocyte gene mutations, familial and non-familial forms of focal segmental glomerulosclerosis, Alport syndrome, membranous nephropathy, acute kidney injury, and medullary cystic kidney disease. Elevated CRELD2 levels can also be detected in urine and kidney tissue in animal models of endoplasmic reticulum (ER) stress-associated kidney disease. CRELD2 levels can provide early signs of developing an ER stress-associated kidney disease. CRELD2 levels can also be measured to monitor progress of treatments of such diseases. CRELD2 levels in a urine or tissue sample can be determined using a monoclonal or a polyclonal antibody.

CRELD2 is a recently identified ER stress-inducible secreted protein and has not been studied in any kidney disease yet. The present inventors have found that CRELD2 is induced in ER-stressed podocytes and renal proximal tubular cells, respectively, and excreted in the urine at very early stage of diseases. Urinary CRELD2 excretion is detected in human DN patients associated with podocyte ER stress, in ADTKD-UMOD and severe ischemic AKI patients caused by tubular ER stress. The present teachings have important clinical applications for early identification of individuals at risk for disease progression and for following the treatment response. There are broad clinical uses of CRELD2 as a urine biomarker for ER-stress-associated kidney diseases including, such as but without limitation, CNS and FSGS caused by different podocyte gene mutations, Alport syndrome, and acute kidney injury.

Therapeutic Methods

Also provided is a process of treating an ER stress-associated disease in a subject in need administration of a therapeutically effective amount of a therapeutic agent, so as to substantially inhibit an ER stress-associated disease, slow the progress of an ER stress-associated disease, or limit the development of an ER stress-associated disease.

Therapeutic agents can include antibiotics or blood pressure/cholesterol/protein lowering medication, cytotoxic agents (e.g., cyclophosphamide), steroids (e.g., prednisolone), or immunosuppressants (e.g., mychophenolate mofetil (MMF)). A therapeutic method that can be administered can include dialysis, therapy for diabetes (e.g., insulin, blood sugar lowering medication), or therapy for high blood pressure (e.g., blood-pressure lowing medication).

Methods described herein are generally performed on a subject in need thereof. A subject in need of the therapeutic methods described herein can be a subject having, diagnosed with, suspected of having, or at risk for developing an ER stress-associated disease. A determination of the need for treatment can be typically be assessed by a history and physical exam consistent with the disease or condition at issue. Diagnosis of the various conditions treatable by the methods described herein is within the skill of the art. The subject can be an animal subject, including a mammal, such as horses, cows, dogs, cats, sheep, pigs, mice, rats, monkeys, hamsters, guinea pigs, and chickens, and humans. For example, the subject can be a human subject.

Generally, a safe and effective amount of a therapeutic agent is, for example, that amount that would cause the desired therapeutic effect in a subject while minimizing undesired side effects. In various embodiments, an effective amount of a therapeutic agent described herein can substantially inhibit an ER stress-associated disease, slow the progress of an ER stress-associated disease, or limit the development of an ER stress-associated disease.

According to the methods described herein, administration can be parenteral, pulmonary, oral, topical, intradermal, intramuscular, intraperitoneal, intravenous, subcutaneous, intranasal, epidural, ophthalmic, buccal, or rectal administration.

When used in the treatments described herein, a therapeutically effective amount of a therapeutic agent can be employed in pure form or, where such forms exist, in pharmaceutically acceptable salt form and with or without a pharmaceutically acceptable excipient. For example, the compounds of the present disclosure can be administered, at a reasonable benefit/risk ratio applicable to any medical treatment, in a sufficient amount to substantially inhibit an ER stress-associated disease, slow the progress of an ER stress-associated disease, or limit the development of an ER stress-associated disease.

The amount of a composition described herein that can be combined with a pharmaceutically acceptable carrier to produce a single dosage form will vary depending upon the host treated and the particular mode of administration. It will be appreciated by those skilled in the art that the unit content of agent contained in an individual dose of each dosage form need not in itself constitute a therapeutically effective amount, as the necessary therapeutically effective amount could be reached by administration of a number of individual doses.

Toxicity and therapeutic efficacy of compositions described herein can be determined by standard pharmaceutical procedures in cell cultures or experimental animals for determining the $LD_{50}$ (the dose lethal to 50% of the population) and the $ED_{50}$, (the dose therapeutically effective in 50% of the population). The dose ratio between toxic and therapeutic effects is the therapeutic index that can be expressed as the ratio $LD_{50}/ED_{50}$, where larger therapeutic indices are generally understood in the art to be optimal.

The specific therapeutically effective dose level for any particular subject will depend upon a variety of factors including the disorder being treated and the severity of the disorder; activity of the specific compound employed; the specific composition employed; the age, body weight, general health, sex and diet of the subject; the time of administration; the route of administration; the rate of excretion of the composition employed; the duration of the treatment; drugs used in combination or coincidental with the specific compound employed; and like factors well known in the medical arts (see e.g., Koda-Kimble et al. (2004) Applied Therapeutics: The Clinical Use of Drugs, Lippincott Williams & Wilkins, ISBN 0781748453; Winter (2003) Basic Clinical Pharmacokinetics, 4$^{th}$ ed., Lippincott Williams & Wilkins, ISBN 0781741475; Sharqel (2004) Applied Biopharmaceutics & Pharmacokinetics, McGraw-Hill/Appleton & Lange, ISBN 0071375503). For example, it is well within the skill of the art to start doses of the composition at levels lower than those required to achieve the desired therapeutic effect and to gradually increase the dosage until the desired effect is achieved. If desired, the effective daily dose may be divided into multiple doses for purposes of administration. Consequently, single dose compositions may contain such amounts or submultiples thereof to make up the daily dose. It will be understood, however, that the total daily usage of the compounds and compositions of the present disclosure will be decided by an attending physician within the scope of sound medical judgment.

Again, each of the states, diseases, disorders, and conditions, described herein, as well as others, can benefit from compositions and methods described herein. Generally, treating a state, disease, disorder, or condition includes preventing or delaying the appearance of clinical symptoms in a mammal that may be afflicted with or predisposed to the state, disease, disorder, or condition but does not yet experience or display clinical or subclinical symptoms thereof. Treating can also include inhibiting the state, disease, disorder, or condition, e.g., arresting or reducing the development of the disease or at least one clinical or subclinical symptom thereof. Furthermore, treating can include relieving the disease, e.g., causing regression of the state, disease, disorder, or condition or at least one of its clinical or subclinical symptoms. A benefit to a subject to be treated can be either statistically significant or at least perceptible to the subject or to a physician.

Administration of a therapeutic agent can occur as a single event or over a time course of treatment. For example, a therapeutic agent can be administered daily, weekly, biweekly, or monthly. For treatment of acute conditions, the time course of treatment will usually be at least several days. Certain conditions could extend treatment from several days to several weeks. For example, treatment could extend over one week, two weeks, or three weeks. For more chronic conditions, treatment could extend from several weeks to several months or even a year or more.

Treatment in accord with the methods described herein can be performed prior to, concurrent with, or after conventional treatment modalities for an ER stress-associated disease.

A therapeutic agent can be administered simultaneously or sequentially with another agent, such as an antibiotic, an anti-inflammatory, or another agent. For example, a therapeutic agent can be administered simultaneously with another agent, such as an antibiotic or an anti-inflammatory. Simultaneous administration can occur through administration of separate compositions, each containing one or more of a therapeutic agent, an antibiotic, an anti-inflammatory, or another agent. Simultaneous administration can occur through administration of one composition containing two or more of a therapeutic agent, an antibiotic, an anti-inflammatory, or another agent. A therapeutic agent can be administered sequentially with an antibiotic, an anti-inflammatory, or another agent. For example, a therapeutic agent can be administered before or after administration of an antibiotic, an anti-inflammatory, or another agent.

Kits

Also provided are kits. Such kits can include an agent or composition described herein and, in certain embodiments, instructions for administration. Such kits can facilitate performance of the methods described herein. When supplied as a kit, the different components of the composition can be packaged in separate containers and admixed immediately before use. Components include, but are not limited to an antibody to an ER stress biomarker (e.g., CRELD2 or BiP), a control sample, or a biological sample. Such packaging of the components separately can, if desired, be presented in a pack or dispenser device which may contain one or more unit dosage forms containing the composition. The pack may, for example, comprise metal or plastic foil such as a blister pack. Such packaging of the components separately can also, in certain instances, permit long-term storage without losing activity of the components.

Kits may also include reagents in separate containers such as, for example, sterile water or saline to be added to a lyophilized active component packaged separately. For example, sealed glass ampules may contain a lyophilized component and in a separate ampule, sterile water, sterile saline or sterile each of which has been packaged under a neutral non-reacting gas, such as nitrogen. Ampules may consist of any suitable material, such as glass, organic polymers, such as polycarbonate, polystyrene, ceramic, metal or any other material typically employed to hold reagents. Other examples of suitable containers include bottles that may be fabricated from similar substances as ampules, and envelopes that may consist of foil-lined interiors, such as aluminum or an alloy. Other containers include test tubes, vials, flasks, bottles, syringes, and the like. Containers may have a sterile access port, such as a bottle having a stopper that can be pierced by a hypodermic injection needle. Other containers may have two compartments that are separated by a readily removable membrane that upon removal permits the components to mix. Removable membranes may be glass, plastic, rubber, and the like.

In certain embodiments, kits can be supplied with instructional materials. Instructions may be printed on paper or other substrate, and/or may be supplied as an electronic-readable medium, such as a floppy disc, mini-CD-ROM, CD-ROM, DVD-ROM, Zip disc, videotape, audio tape, and the like. Detailed instructions may not be physically associated with the kit; instead, a user may be directed to an Internet web site specified by the manufacturer or distributor of the kit.

Compositions and methods described herein utilizing molecular biology protocols can be according to a variety of standard techniques known to the art (see, e.g., Sambrook and Russel (2006) Condensed Protocols from Molecular Cloning: A Laboratory Manual, Cold Spring Harbor Laboratory Press, ISBN-10: 0879697717; Ausubel et al. (2002) Short Protocols in Molecular Biology, 5th ed., Current Protocols, ISBN-10: 0471250929; Sambrook and Russel (2001) Molecular Cloning: A Laboratory Manual, 3d ed., Cold Spring Harbor Laboratory Press, ISBN-10: 0879695773; Elhai, J. and Wolk, C. P. 1988. Methods in Enzymology 167, 747-754; Studier (2005) Protein Expr Purif. 41(1), 207-234; Gellissen, ed. (2005) Production of Recombinant Proteins: Novel Microbial and Eukaryotic Expression Systems, Wiley-VCH, ISBN-10: 3527310363; Baneyx (2004) Protein Expression Technologies, Taylor & Francis, ISBN-10: 0954523253).

Definitions and methods described herein are provided to better define the present disclosure and to guide those of ordinary skill in the art in the practice of the present disclosure. Unless otherwise noted, terms are to be understood according to conventional usage by those of ordinary skill in the relevant art.

In some embodiments, numbers expressing quantities of ingredients, properties such as molecular weight, reaction conditions, and so forth, used to describe and claim certain embodiments of the present disclosure are to be understood as being modified in some instances by the term "about." In some embodiments, the term "about" is used to indicate that a value includes the standard deviation of the mean for the device or method being employed to determine the value. In some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the present disclosure are approximations, the numerical values set forth in the specific examples are reported as precisely as practicable. The numerical values presented in some embodiments of the present disclosure may contain certain errors necessarily resulting from the standard deviation found in their respective testing measurements. The recitation of ranges of values herein is merely intended to serve as a shorthand method of referring individually to each separate value falling within the range. Unless otherwise indicated herein, each individual value is incorporated into the specification as if it were individually recited herein.

In some embodiments, the terms "a" and "an" and "the" and similar references used in the context of describing a particular embodiment (especially in the context of certain of the following claims) can be construed to cover both the singular and the plural, unless specifically noted otherwise. In some embodiments, the term "or" as used herein, including the claims, is used to mean "and/or" unless explicitly indicated to refer to alternatives only or the alternatives are mutually exclusive.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and can also cover other unlisted steps. Similarly, any composition or device that "comprises," "has" or "includes" one or more features is not limited to possessing only those one or more features and can cover other unlisted features.

All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the present disclosure and does not pose a limitation on the scope of the present disclosure otherwise claimed. No language in the specification should be construed as indicating any non-claimed element essential to the practice of the present disclosure.

Groupings of alternative elements or embodiments of the present disclosure disclosed herein are not to be construed as limitations. Each group member can be referred to and claimed individually or in any combination with other members of the group or other elements found herein. One or more members of a group can be included in, or deleted from, a group for reasons of convenience or patentability. When any such inclusion or deletion occurs, the specification is herein deemed to contain the group as modified thus fulfilling the written description of all Markush groups used in the appended claims.

Citation of a reference herein shall not be construed as an admission that such is prior art to the present disclosure.

Having described the present disclosure in detail, it will be apparent that modifications, variations, and equivalent embodiments are possible without departing the scope of the present disclosure defined in the appended claims. Furthermore, it should be appreciated that all examples in the present disclosure are provided as non-limiting examples.

EXAMPLES

The following non-limiting examples are provided to further illustrate the present disclosure. It should be appreciated by those of skill in the art that the techniques disclosed in the examples that follow represent approaches the inventors have found function well in the practice of the present disclosure, and thus can be considered to constitute examples of modes for its practice. However, those of skill in the art should, in light of the present disclosure, appreciate that many changes can be made in the specific embodiments that are disclosed and still obtain a like or similar result without departing from the spirit and scope of the present disclosure.

Example 1: Cysteine-Rich with EGF-Like Domain Protein 2 (CRELD2) as a Biomarker for Endoplasmic Reticulum (ER) Stress-Associated Kidney Disease This example described the discovery of CRELD2 as a biomarker to detect an ER stress associated kidney disease.

Endoplasmic reticulum (ER) stress and disrupted proteostasis contribute to the pathogenesis of a variety of glomerular and tubular diseases. Thus, it is imperative to develop noninvasive biomarkers for detecting ER stress in podocytes or tubular cells in the incipient stage of disease, when a kidney biopsy may not yet be clinically indicated. Cysteine-rich with EGF-like domain protein 2 (CRELD2) localizes to the ER and is secreted in response to ER stress in several cell types.

In human autosomal dominant tubulointerstitial kidney disease (ADTKD) patients, diabetic nephropathy patients, and ischemic AKI patients, and by using mouse models of human nephrotic syndrome caused by mutant laminin β2 protein-induced podocyte ER stress and acute kidney injury (AKI) triggered by tunicamycin- or ischemia reperfusion-induced tubular ER stress, CRELD2 was examined as a potential urine biomarker for detecting ER stress in podocytes or renal tubular cells. ER stress upregulated CRELD2 expression in podocytes and tubular cells. Notably, urinary CRELD2 excretion concurrent with podocyte or tubular cell ER stress preceded clinical or histologic manifestations of the corresponding disease.

(i) Diabetic Neuropathy (DN)

Figure 8:
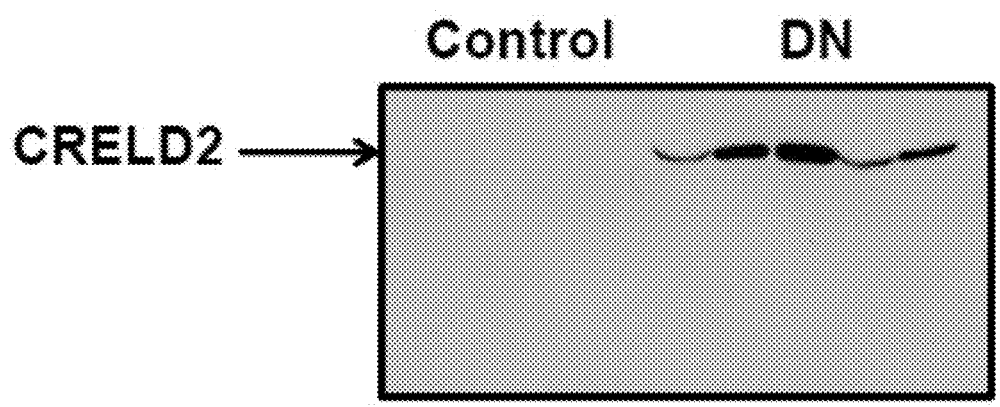
FIG. 8 illustrates immunodetection of CRELD2 excretion in the urines of human diabetic nephropathy (DN) patients with podocyte ER stress.

In addition, urinary CRELD2 excretion was detected in human diabetic nephropathy (DN) patients caused by podocyte ER stress, but not in healthy controls (see e.g., FIG. 8). Thus, CRELD2 can serve as a urine diagnostic or prognostic biomarker in ER stress-related kidney diseases to help stratify disease risk, predict disease progression, monitor treatment response, and identify subgroups of patients who can be treated with ER stress modulators in a highly targeted manner. Based on the above results, there can be extensive clinical use of CRELD2 as a urine biomarker for ER-stress-related kidney diseases including hereditary proteinuric diseases caused by different podocyte gene mutations, familial and non-familial forms of focal segmental glomerulosclerosis, Alport syndrome, membranous nephropathy, acute kidney injury, and medullary cystic kidney disease.

(ii) Tunicamycin (TM) or I/R-Induced Acute Kidney Injury (AKI) Mouse Model

Figure 3:
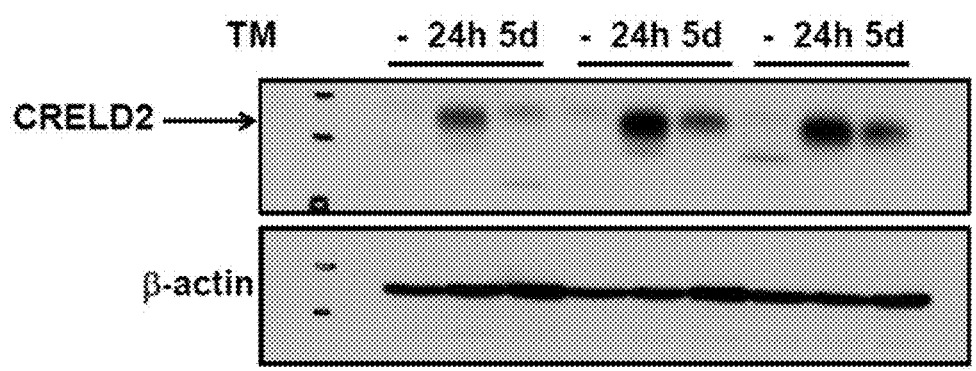
FIG. 3 illustrates immunodetection of CRELD2 induced in kidney lysates from TM-injected mice.
Figure 4:
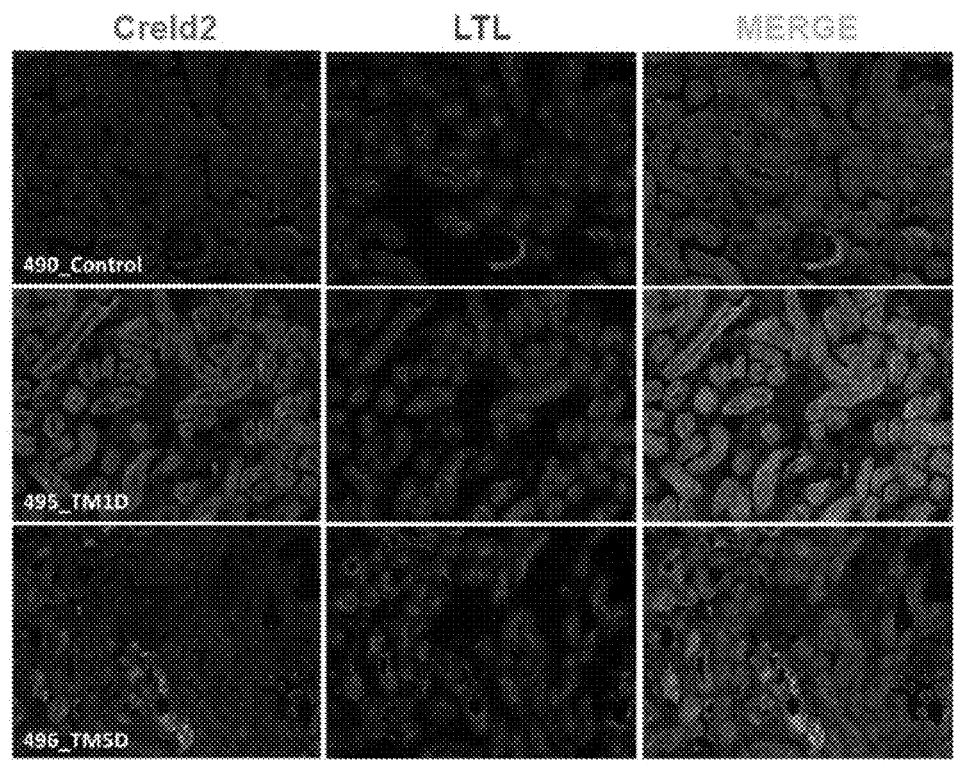
FIG. 4 illustrates immunofluorescence detection of CRELD2 in kidney tissue, and show that CRELD2 is upregulated in ER-stressed proximal tubular cells.
Figure 5:
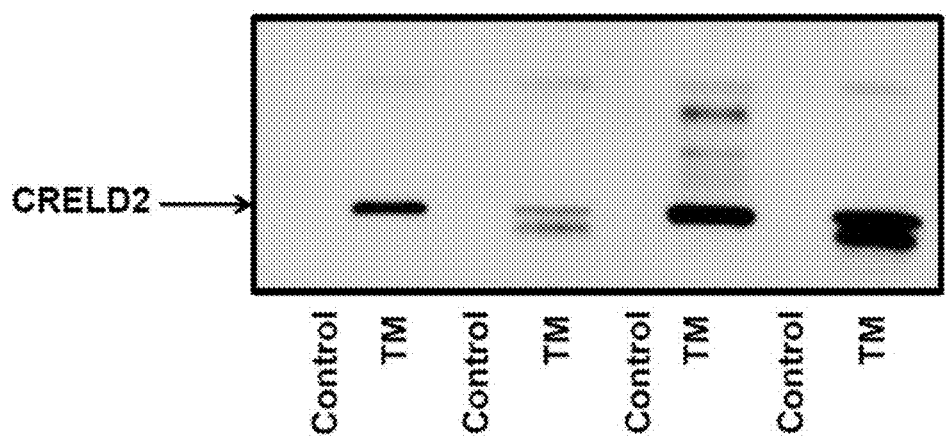
FIG. 5 illustrates immunodetection of CRELD2 in the urine of tunicamycin-injected mice 24 h after injection.
Figure 6:
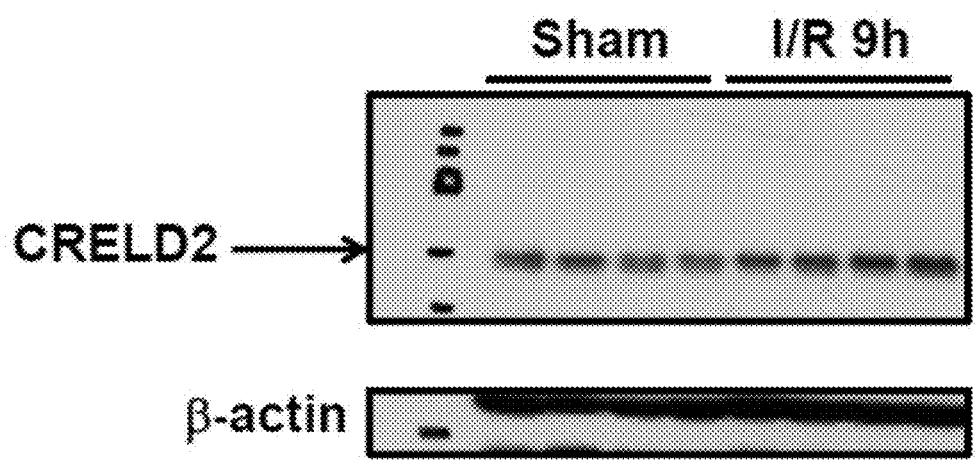
FIG. 6 illustrates immunodetection of CRELD2 in kidney lysates from I/R-injured mice as early as 9 h after reperfusion.
Figure 7:
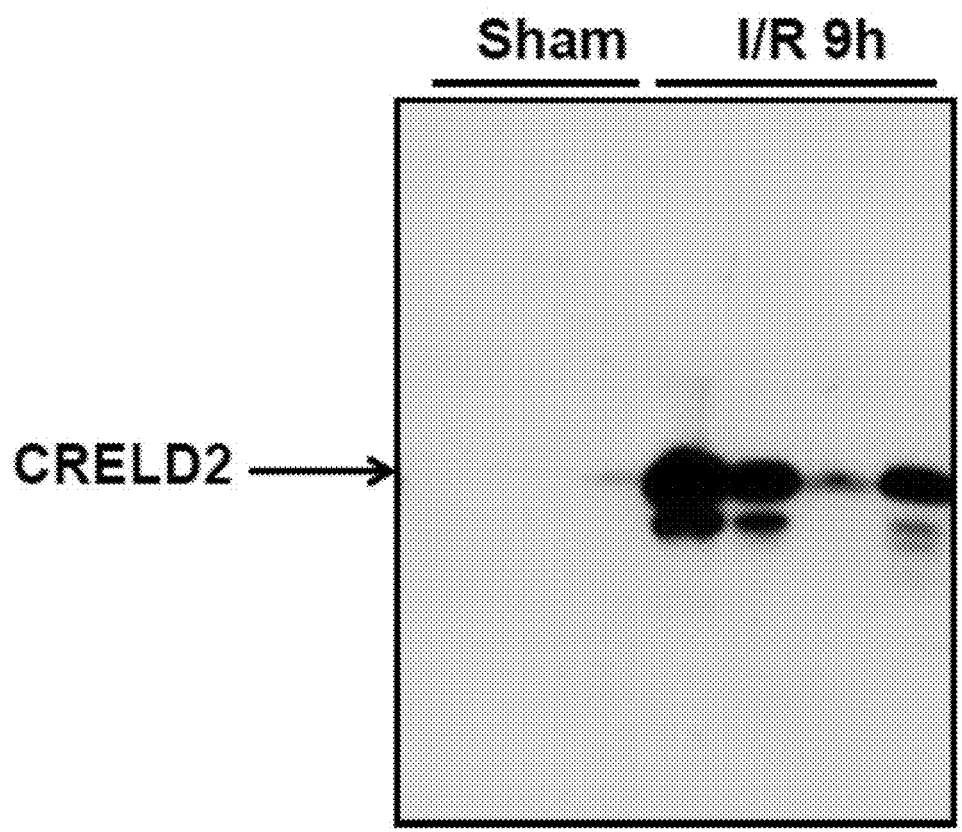
FIG. 7 illustrates immunodetection of CRELD2 in urine specimens within 9 h reflow from I/R injured mice.

FIG. 3 illustrates that CRELD2 is upregulated in the kidney due to tubular ER stress in a tunicamycin (TM)-induced acute kidney injury mouse model. TM is an ER stress inducer. CRELD2 is induced in kidney lysates from TM-injected mice. FIG. 4 illustrates that CRELD2 is upregulated in the ER-stressed proximal tubular cells (marked by LTL) at 1 day and 5 days post TM injection, respectively. FIG. 5 illustrates that CRELD2 can be detected in the urine of TM-injected mice 24 h after injection. FIG. 6 illustrates that CRELD2 is upregulated in the kidney lysate at 9 hours post ischemic-injury compared to sham-operated mice in an ischemia/reperfusion (I/R)-induced acute kidney injury mouse model. FIG. 7 illustrates immunodetection of CRELD2 in urine specimens within 9 h reflow from I/R injured mice.

(iii) Nephrotic Syndrome (NS)

Figure 2:
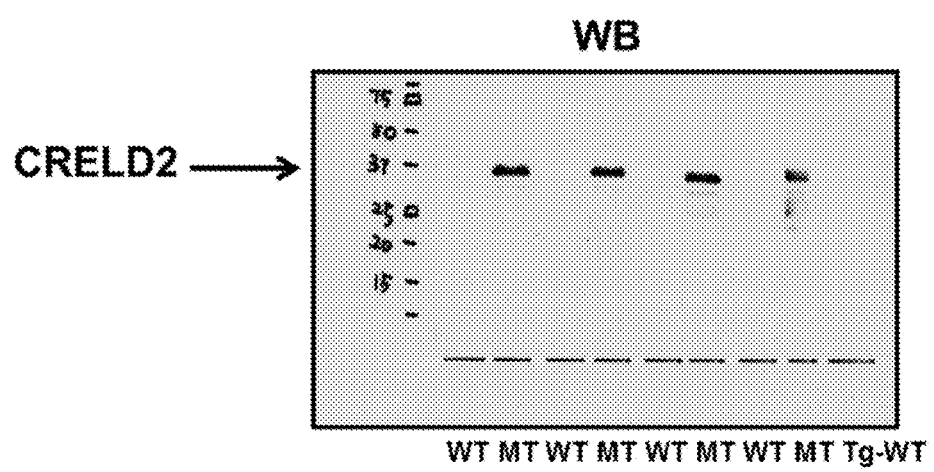
FIG. 2 illustrates CRELD2 can be detected from the urine of C321R mutant mice even when proteinuria is trace (P25).

FIG. 1 illustrates that CRELD2 secretion is increased by ER-stressed C321R podocytes. In FIG. 11, WT, Wild-type; MT, Mutant; Tg-WT, transgenic mice expressing WT-LAMB2 as controls. As shown herein, CRELD2 can serve as a urinary biomarker to detect podocyte ER stress in a podocyte ER stress-induced nephrotic syndrome (NS) mouse model, and can be detected using an antibody in a Western blot assay (see e.g., FIG. 2). Immunodetection of CRELD2 in urine samples from C321R mutant mice is possible even when proteinuria is in trace amounts (P25). In FIG. 2, WT denotes Wild-type; MT denotes Mutant; and Tg-WT denotes transgenic mice expressing WT-LAMB2 as controls.

Example 2: Further Studies of Cysteine-Rich with EGF-Like Domains 2 (CRELD2) as an Early Mechanistic Urinary Biomarker for Endoplasmic Reticulum (ER) Stress-Associated Kidney Disease This example describes further studies of CRELD2 as a urine ER stress biomarker is several models of human disease and in human patients.

(i) CRELD2 as an Early Biomarker in Nephrotic Syndrome (NS)

Figure 9A:
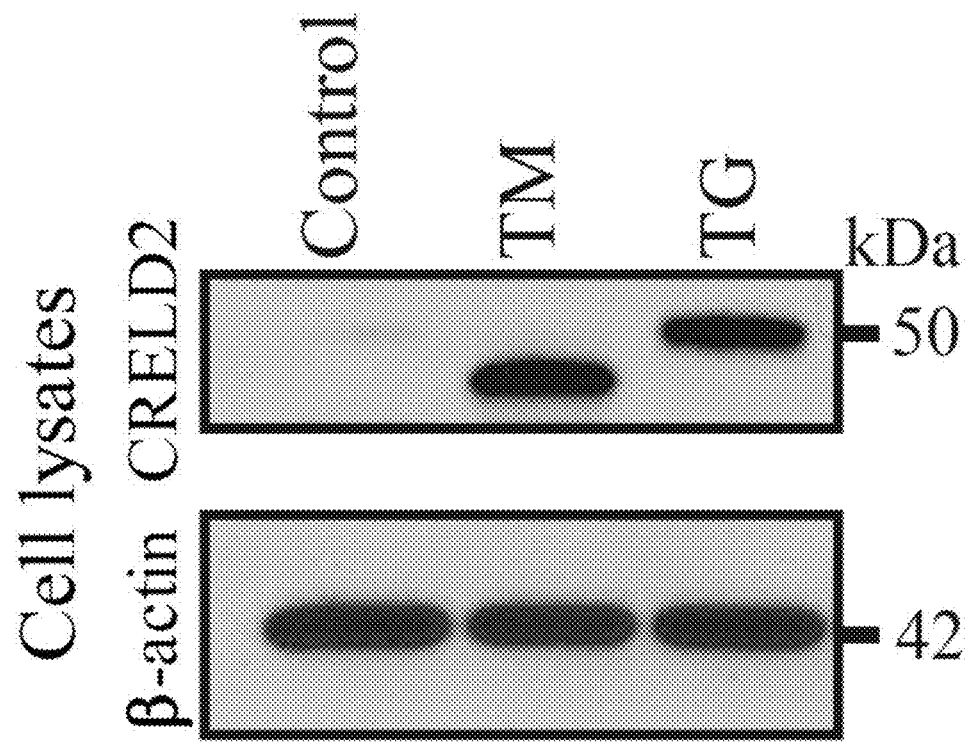
FIG. 9A-FIG. 9I is a series of images and graphs showing CRELD2 is a novel urinary biomarker for detecting podocyte ER stress in the early stages of NS. Primary podocytes (P1 or P2) were isolated and cultured from WT mice at P27 (FIG. 9A-FIG. 9C).
Figure 9B:
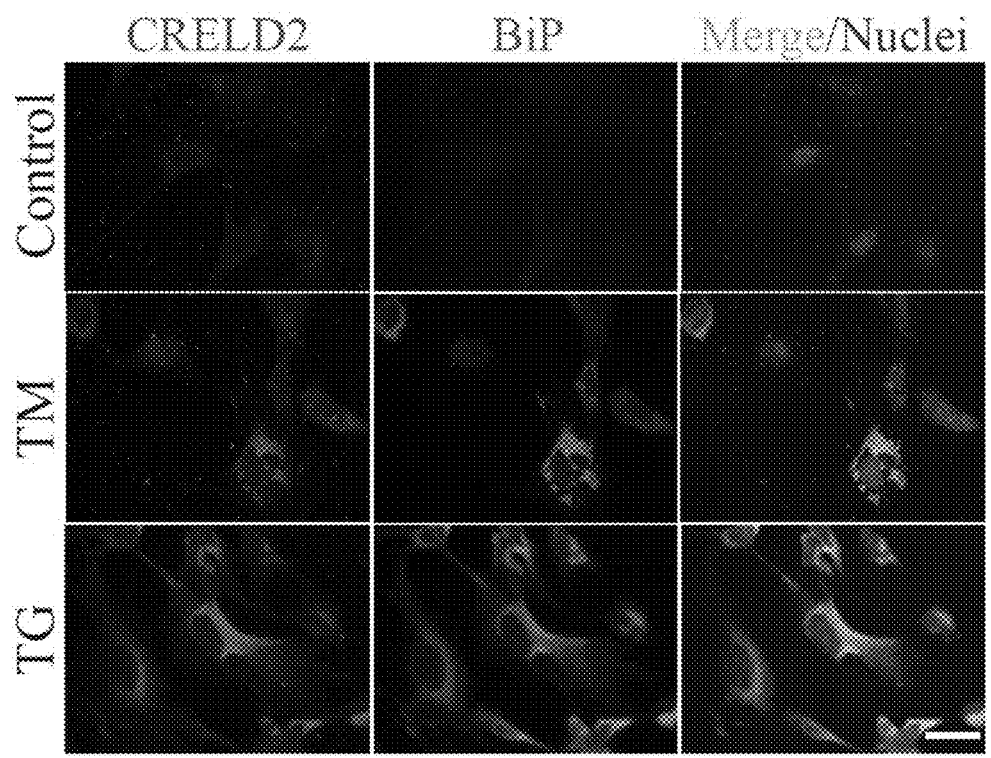

CRELD2 is a urinary biomarker for detecting podocyte ER stress in the early stages of podocyte ER stress-induced nephrotic syndrome (NS) in mice. Initial experiments (see e.g., Example 2) determined ER stress increases CRELD2 expression and secretion in mouse primary podocytes. Mouse podocytes were treated for 24 h with tunicamycin (TM), which activates ER stress by blocking N-linked glycosylation in the ER (26), or TG, which depletes ER calcium through inhibition of ER calcium ATPase (27). Consistent with prior results obtained from Neuro2a cells (22), both ER stressors induced expression of CRELD2, which was barely detectable in vehicle (DMSO)-treated cells (see e.g., FIG. 9A). As expected, it is also noted that TM treatment resulted in expression of an underglycosylated form of CRELD2. Immunofluorescence (IF) of mouse primary podocytes also showed that CRELD2 was upregulated by both ER stressors and that the upregulated CRELD2 in TM- or TG-treated podocytes overlapped exclusively with BiP, a well-known ER stress marker (see e.g., FIG. 9B). The effects of ER stress on CRELD2 secretion were also examined.

Figure 9C:
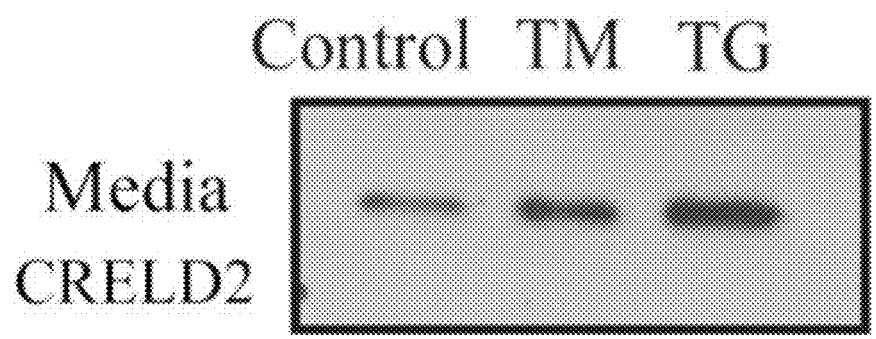

A Western blot (WB) showed that both ER stressors increased CRELD2 secretion into the culture medium by mouse podocytes (see e.g., FIG. 9C), whereas in the absence of ER stress, there was little CRELD2 secretion by mouse podocytes (see e.g., FIG. 9C). These data verify that the upregulation and secretion of CRELD2 induced by ER stress is not a cell-type specific response.

Figure 9D:
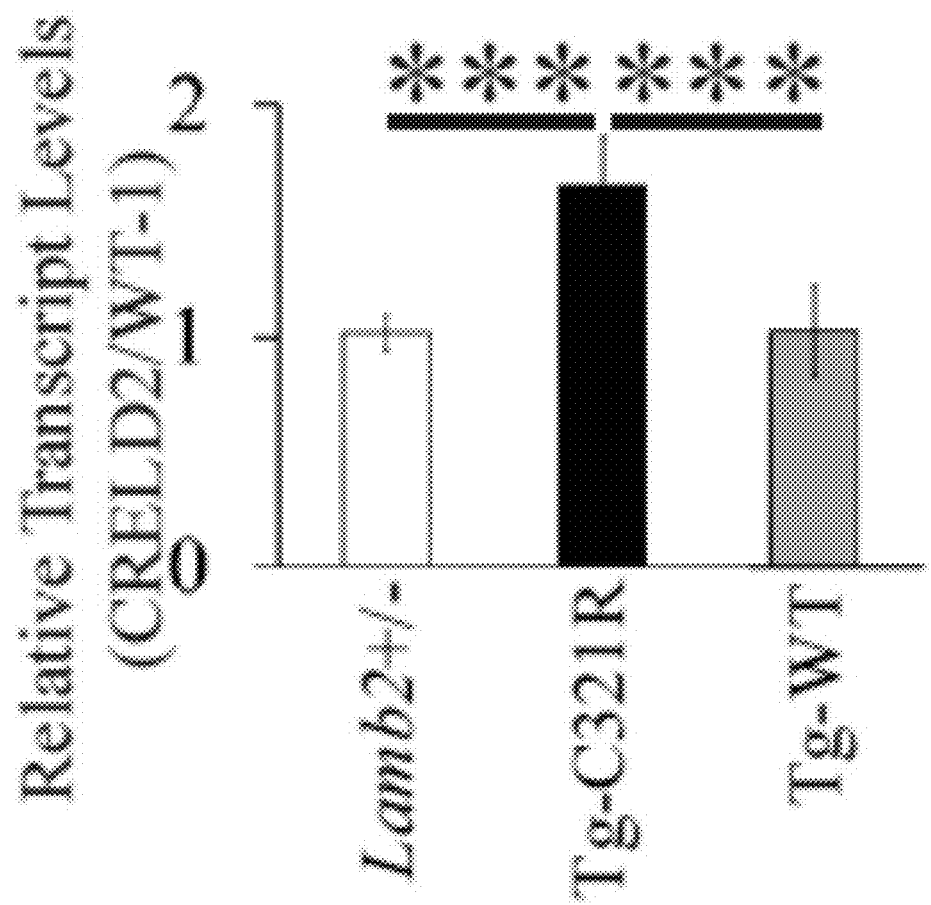
Figure 9E:
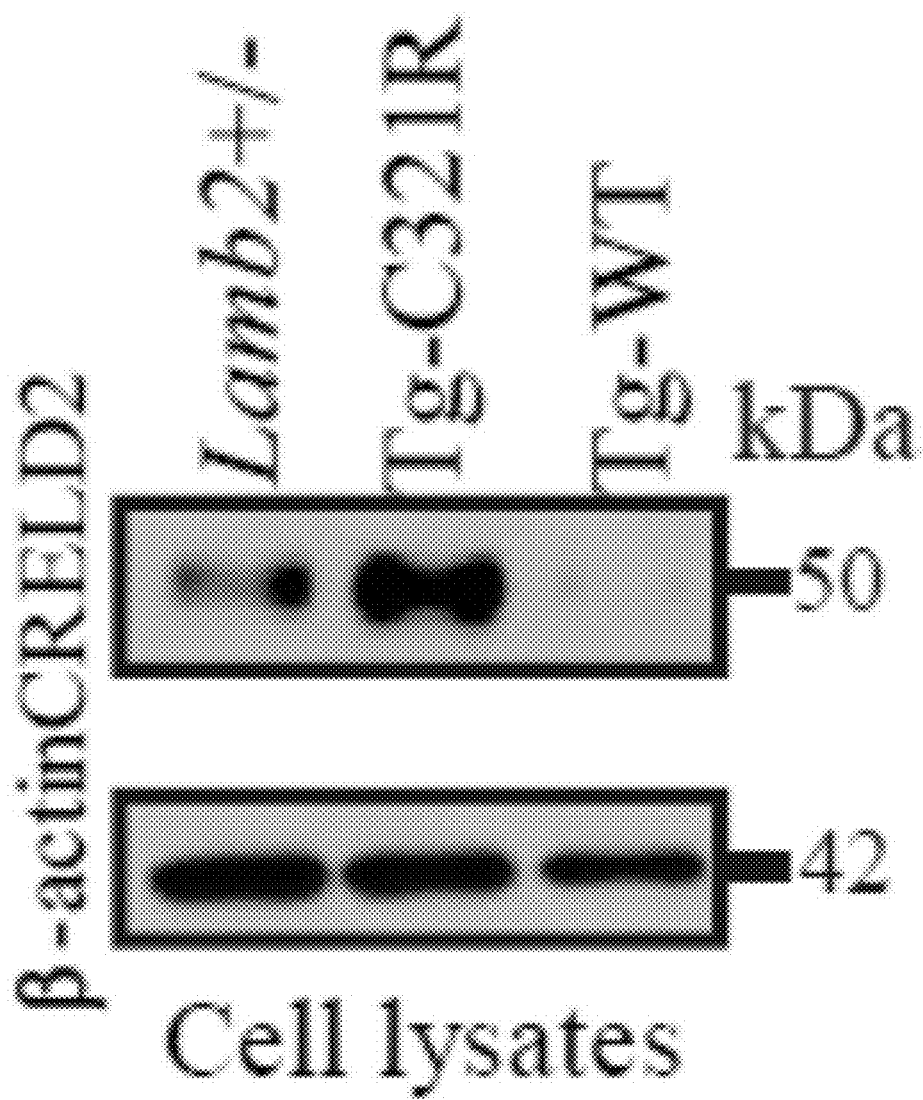
Figure 9F:
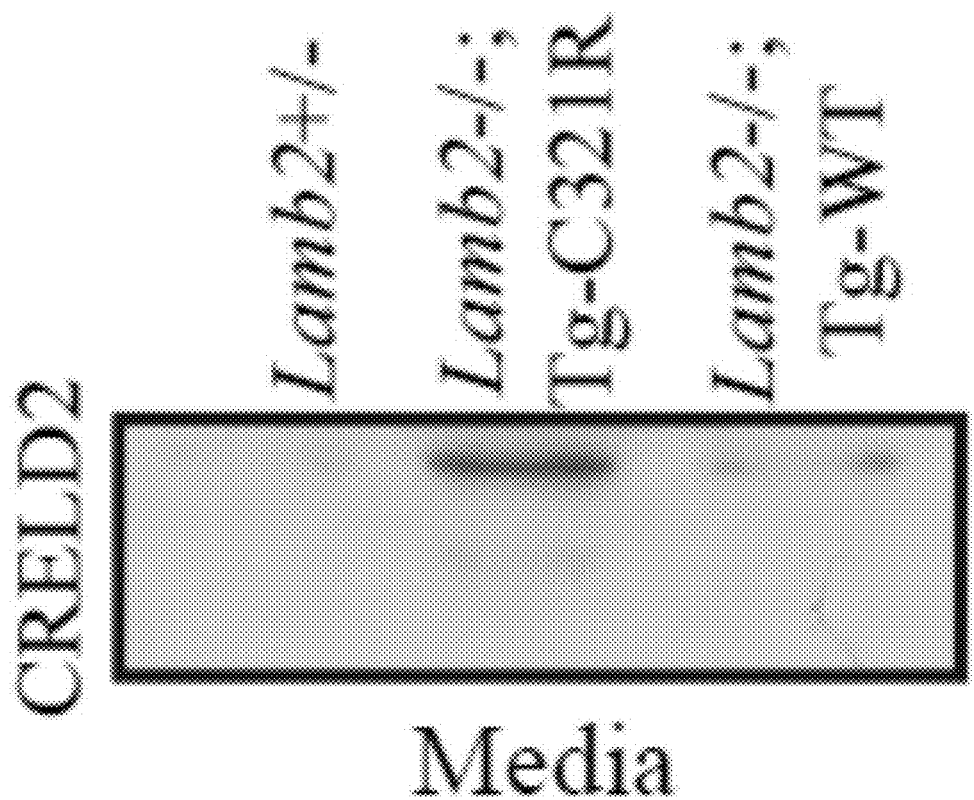
Figure 9G:
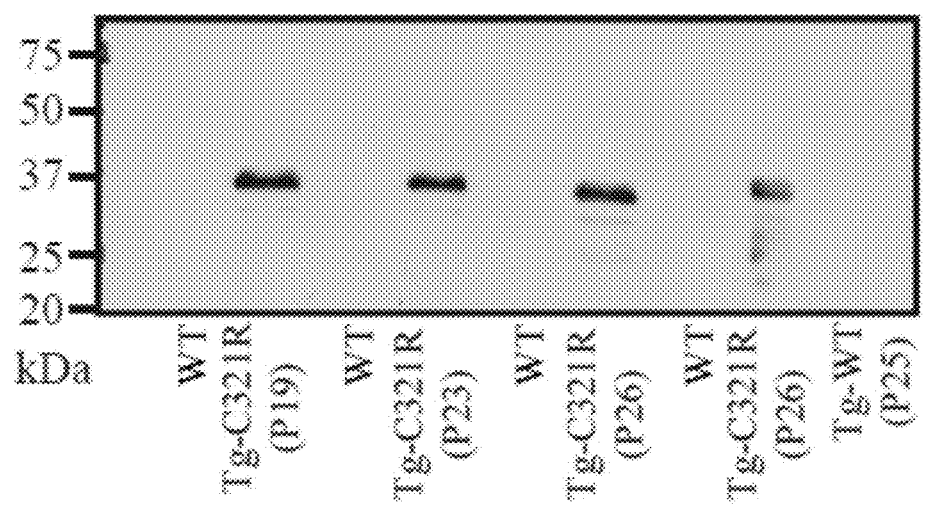
Figure 9H:
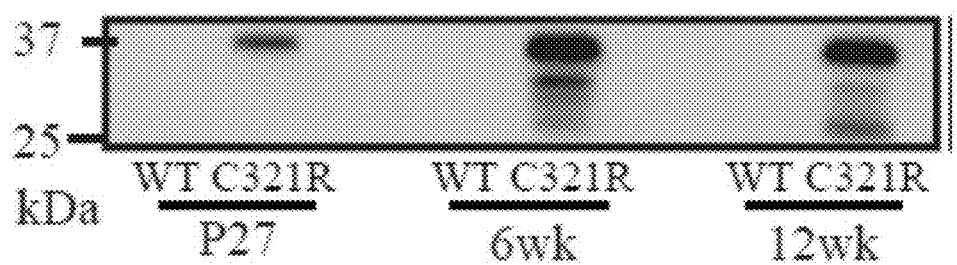
Figure 9I:

Next, CRELD2 was investigated to determine if CRELD2 could serve as a urinary biomarker to detect podocyte ER stress by utilizing a podocyte ER stress-induced nephrotic syndrome (NS) model that was developed (5). It was previously shown that Lamb2$^{-/-}$ mice expressing C321R LAMB2 in podocytes via the podocyte-specific mouse nephrin promoter (Lamb2$^{-/-}$; Tg-C321R mice) resemble features of human NS patients carrying the C321R-LAMB2 mutation (5). It was also shown that in expression-matched Lamb2$^{-/-}$; Tg-WT mice, the expression of WT LAMB2 cDNA in podocytes is sufficient to restore the integrity of the glomerular filtration barrier (GFB) in Lamb2$^{-/-}$ mice (28). For simplicity, Lamb2$^{-/-}$; Tg-C321R and Lamb2$^{-/-}$; Tg-WT mice will hereafter be referred to as Tg-C321R and Tg-WT mice, respectively. Tg-C321R mice begin to develop trace proteinuria by 4 weeks of age before any histological changes and then exhibit mild glomerulosclerosis, diffuse foot process effacement, GBM thickening and overt proteinuria at approximately 6-8 weeks, and finally die after 10-12 weeks. At P24-P28, when Tg-C321R mutants exhibit trace proteinuria without notable renal histological alterations, podocyte ER stress induced by the C321R misfolded protein is evident as demonstrated by the upregulation of BiP and CHOP in Tg-C321R podocytes compared with WT and Tg-WT podocytes. In the current study, these findings were expanded upon by determining whether CRELD2 was also induced and secreted by ER-stressed podocytes at the early stage of proteinuria. Primary podocytes were isolated and cultured from Lamb2$^{+/-}$, Tg-C321R and Tg-WT mice at P27. Real-time PCR demonstrated that CRELD2 transcript levels were significantly increased in Tg-C321R podocytes compared with the WT and Tg-WT podocytes (see e.g., FIG. 9D). A Western blot also revealed CRELD2 upregulation in Tg-C321R podocytes versus the WT and Tg-WT podocytes (see e.g., FIG. 9E). More importantly, as shown in FIG. 9F, secretion of CRELD2 by Tg-C321R podocytes was markedly higher as compared to WT and Tg-WT podocytes. Next, it was determined whether CRELD2 secreted from ER-stressed podocytes was detectable in urine. Using urinary creatinine (Cr) concentrations to normalize for sample loading, a Western blot showed that CRELD2 was easily detected in as little as 3 µl of unprocessed urine specimens from C321R mutants in the incipient stage of NS, but not from WT or Tg-WT mice (see e.g., FIG. 9G), analogous to the secretion of CRELD2 by cultured podocytes following ER stress (see e.g., FIG. 9F). Furthermore, urinary CRELD2 excretion increased in C321R mutants during disease progression from P27 to 6-12 weeks of age (see e.g., FIG. 9H). In contrast, CRELD2 excretion was not detected in the urine of WT or Tg-WT mice at any time point up to 16 weeks of age (see e.g., FIG. 9I). It is noted that CRELD2 in mouse urine had faster electrophoretic motility (37 kDa), which is most likely due to the effect of high concentrations of urinary sodium ions and urea, a well-described phenomenon. Taken together, these data show that CRELD2 cellular secretion and urinary excretion coincide with podocyte ER stress during the development of proteinuria and can be detected at the early stage of the disease.

(ii) CRELD2 is an Early Urinary Biomarker for Monitoring Tubular ER Stress in the TM-Induced Acute Kidney Injury (AKI) Mouse Model Intraperitoneal (IP) injection of TM in mice is a well characterized AKI model caused by renal proximal tubular ER stress (29). This work and others have shown that it manifests as extensive tubular dilation, epithelial flattening, tubular basement membrane denudation and loss of brush borders in proximal tubules which peaks between 4 and 5 days after injection (21, 29). In comparison, glomeruli and other organs are spared (21, 29).

Figure 10A:
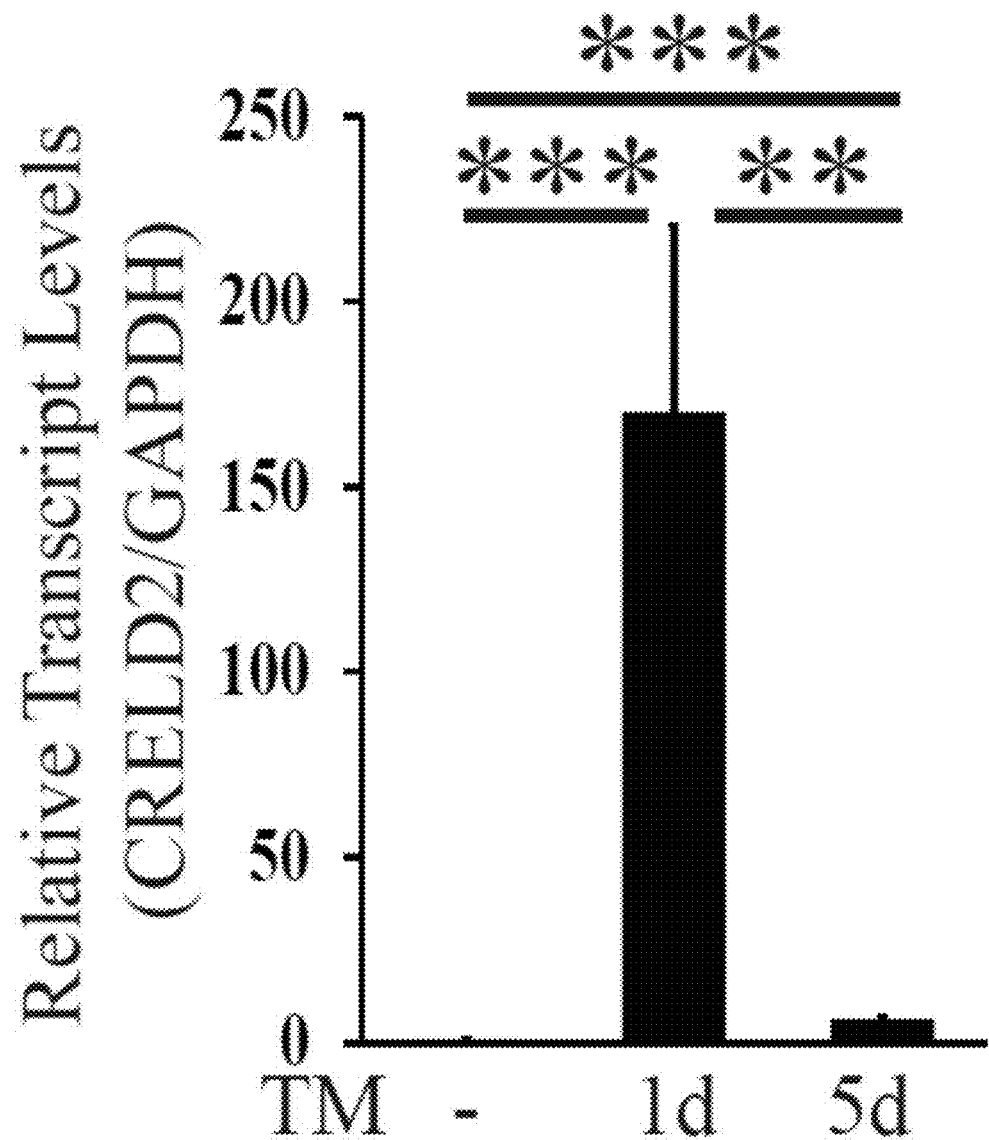
FIG. 10A-FIG. 10E is a series of graphs, images, and Western blots showing urinary CRELD2 excretion coincides with tubular ER stress in the TM-induced AKI mouse model.
Figure 10B:
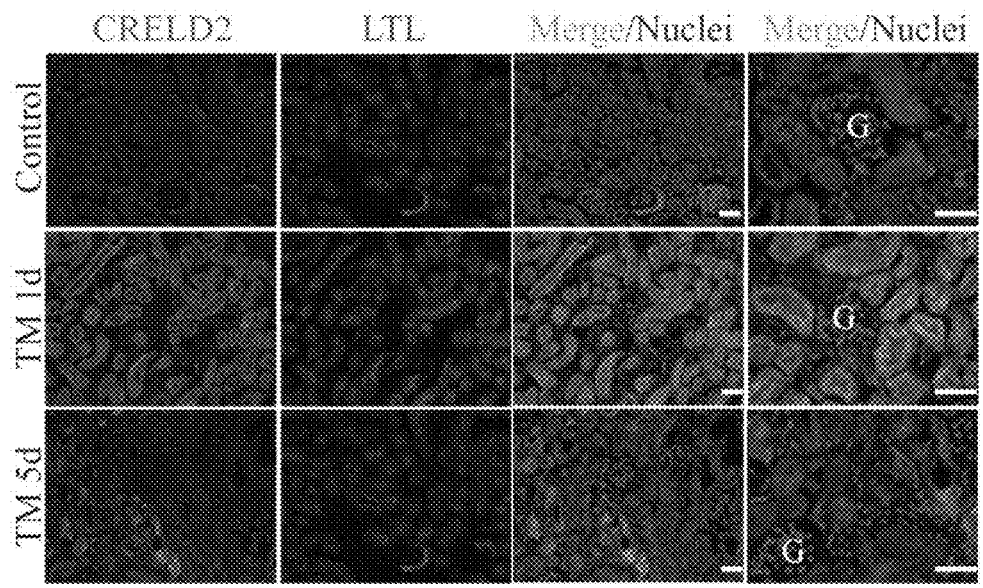
Figure 10C:
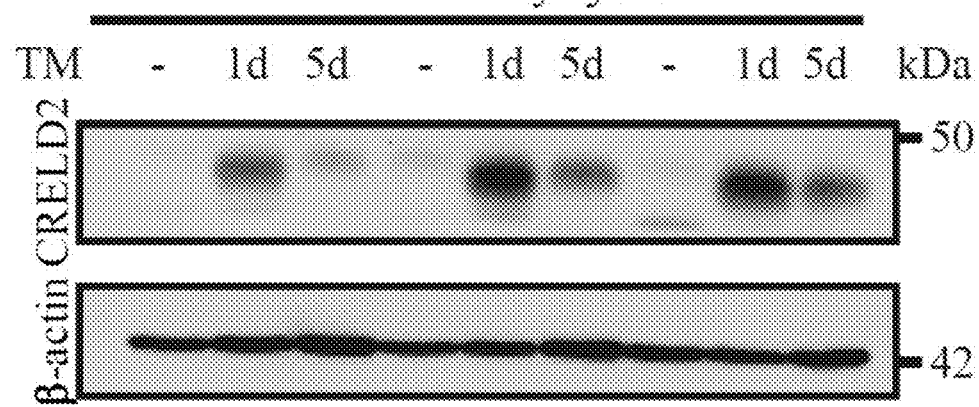
Figure 10D:
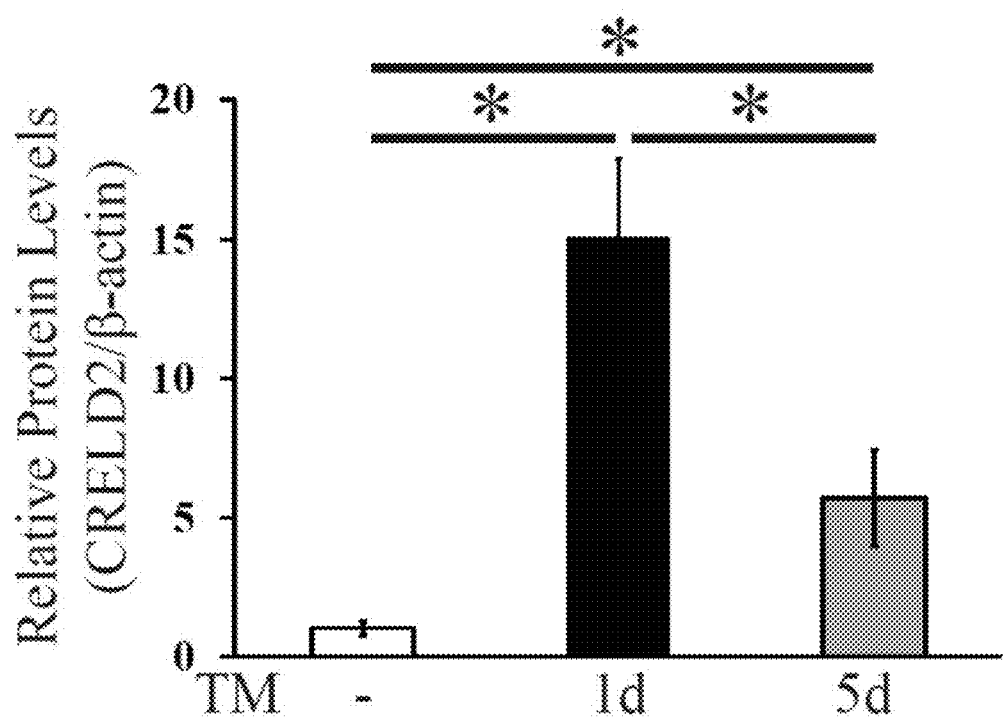
Figure 10E:
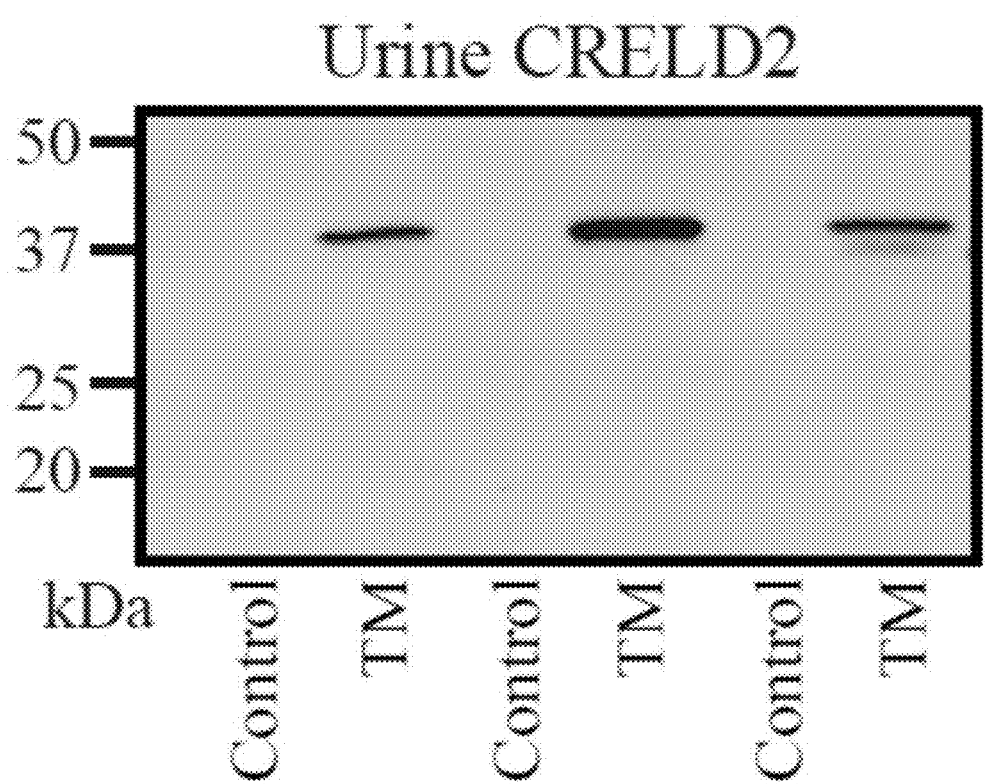

Here, it is also shown that despite normal renal function and the absence of conspicuous histologic changes on day 1 after TM injection, multiple ER stress response genes including BiP, CHOP, MANF and ER degradation-enhancing-mannosidase-like protein (EDEM) are upregulated (21). Whether CRELD2 was induced in ER-stressed renal tubules was further investigated. Indeed, CRELD2 transcript levels in whole-kidney lysates were significantly increased on day 1 after TM injection versus DMSO vehicle-injected controls or day 5 after injection (see e.g., FIG. 10A). Co-IF staining of CRELD2 and the proximal tubular marker Lotus tetragonolobus lectin (LTL) also showed that CRELD2 immunostaining in proximal tubules was substantially upregulated on day 1 following TM injection compared with controls and subsided by 5 days post-injection. Conversely, glomeruli in TM-injected kidneys did not exhibit CRELD2 induction (see e.g., FIG. 10B). WB analysis confirmed that CRELD2 protein expression in kidneys was higher on day 1 compared with controls or day 5 post-injection (see e.g., FIG. 10C-FIG. 10D). Next, it was determined if CRELD2 can be detected in urine on day 1 after treatment with TM. It was previously shown that this time point precedes renal histopathologic changes and upregulation of the early injury marker kidney injury molecule-1 (KIM-1) (21). Indeed, CRELD2 excretion was dramatically increased in urine specimens from TM-injected mice within 24 hours, but not from vehicle-injected mice (see e.g., FIG. 10E). Collectively, these data demonstrate that tubular cell ER stress increases urinary CRELD2 excretion prior to any evidence of the subsequent decline in kidney function or histologic changes due to ER stress-induced AKI, thus establishing the excellent early predictive capacity of CRELD2 as a biomarker.

(iii) CRELD2 is an Early Mechanistic Urinary Biomarker for ER-Stressed Tubular Cells in the Ischemia-Reperfusion-Induced AKI Mouse Model Here, CRELD2 excretion was assessed to determine if it correlates with the disease course in a mouse bilateral (B) 30 minute ischemia-induced AKI model. The controls are sham-operated control mice and the B ischemia model is based on clamping of bilateral renal vascular pedicles for 30 minutes+reperfusion periods of 3 h/9 h/24 h/3 d/7 d/14 d (see e.g., FIG. 11A).

Figure 11A:
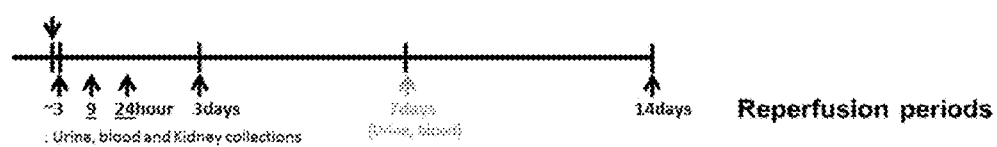
Figure 11B:
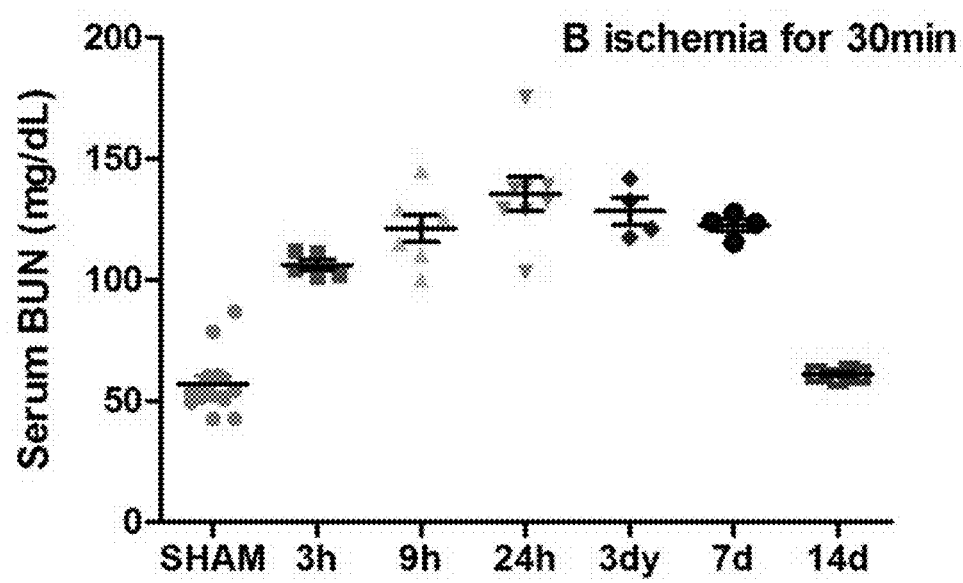

Renal function (serum blood urea nitrogen (BUN)) data demonstrated elevation of BUN at 3 h, peaking of BUN at 24 h and gradually returning to normal renal function at day 14 after ischemic injury (see e.g., graph in FIG. 11B).

Figure 11C:
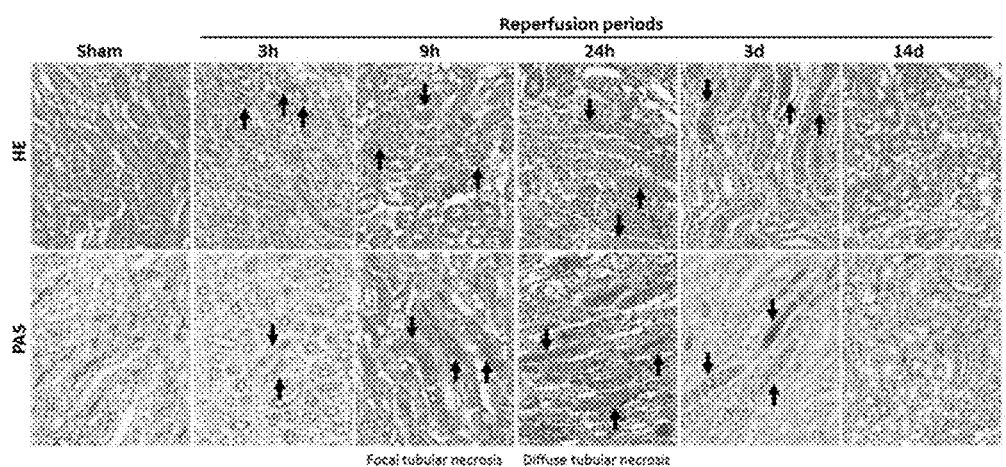

As shown in FIG. 11C, renal histology (HE and PAS staining) clearly showed very mild tubular injury at 3 h, tubular necrosis at 9 h and more severe tubular necrosis at 24 h after ischemic injury. At day 3 post-ischemic injury, tubular recovery was observed, and at day-14 tubular injury resolved.

Figure 11D:
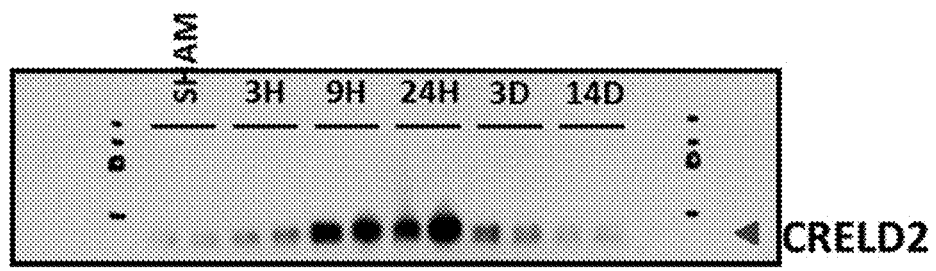
Figure 11E:
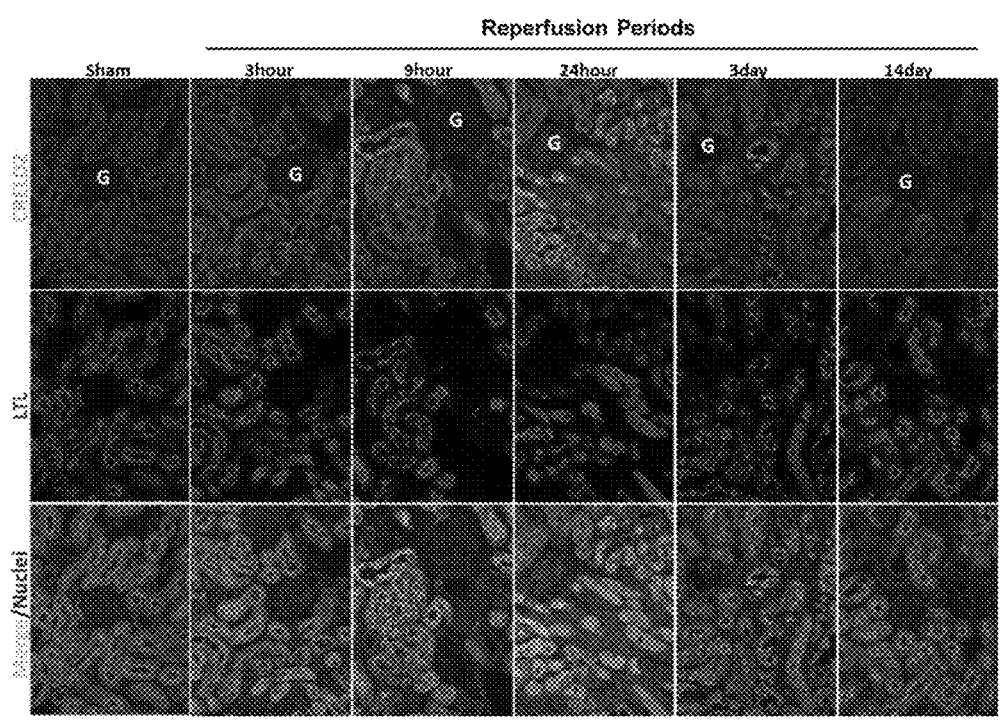

Western blot (WB) from kidney lysates showed that CRELD2 was mildly upregulated in post-ischemic kidneys at 3 hours of reflow compared with sham-operated kidneys (see e.g., FIG. 11D). A significant induction at both 9 hours and 24 hours of reflow was observed in kidneys after ischemic injury (see e.g., FIG. 11D). CRELD2 expression subsided at day 3 of reflow as compared to that at both 9 hours and 24 hours in post-ischemic kidneys (see e.g., FIG. 11D). CRELD2 levels at day 14 became indistinguishable from that in mice undergoing sham surgery (see e.g., FIG. 11D).

Consistent with the Western blot, dual immunofluorescence (IF) staining of sham-operated and post-ischemic kidney sections for CRELD2 and LTL, which Is a marker for proximal tubules, demonstrated that significant CRELD2 induction occurred in injured proximal tubular cells by 9 hours and peaked by 24 hours after the ischemic Injury. In contrast, the glomeruli (G) were devoid of CRELD2 expression (see e.g., FIG. 11E).

Figure 11F:
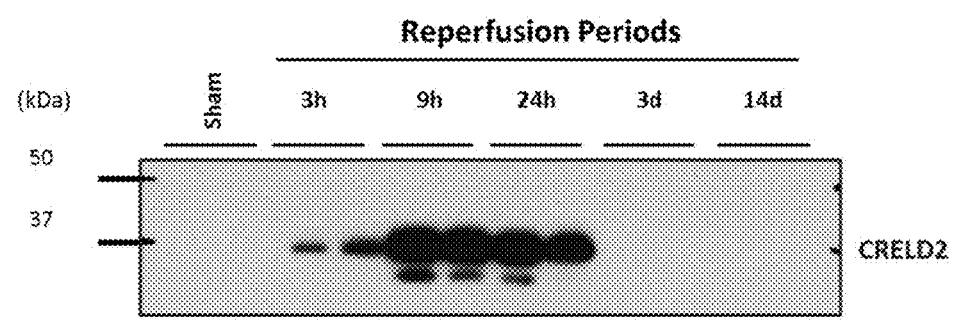

The levels of urinary CRELD2 excretion after bilateral 30 min ischemia correlate with the AKI severity in the disease course and thus can be used to monitor AKI progression or recovery (see e.g., FIG. 11F).

Figure 11G:
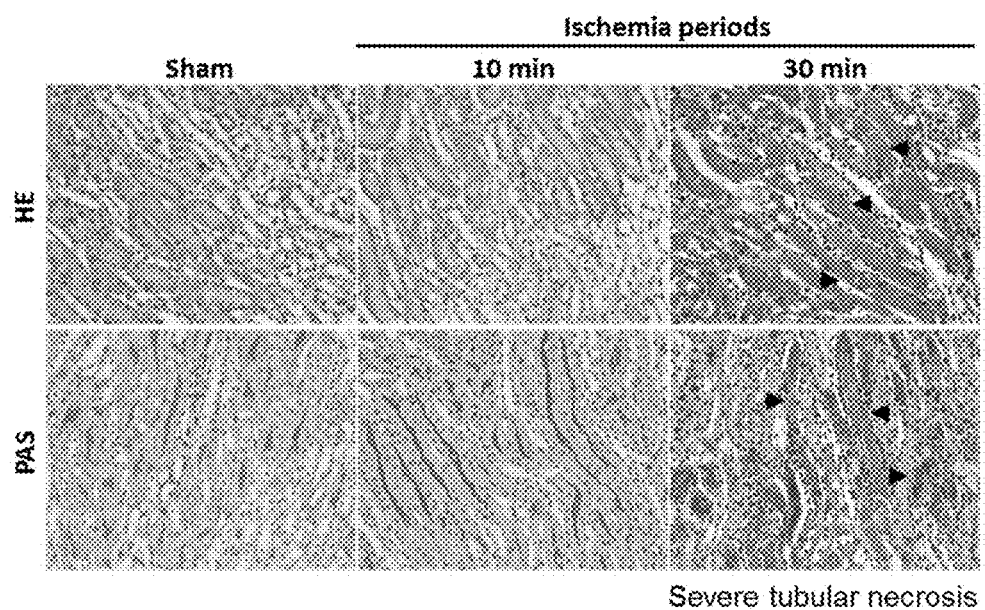
Figure 11H:
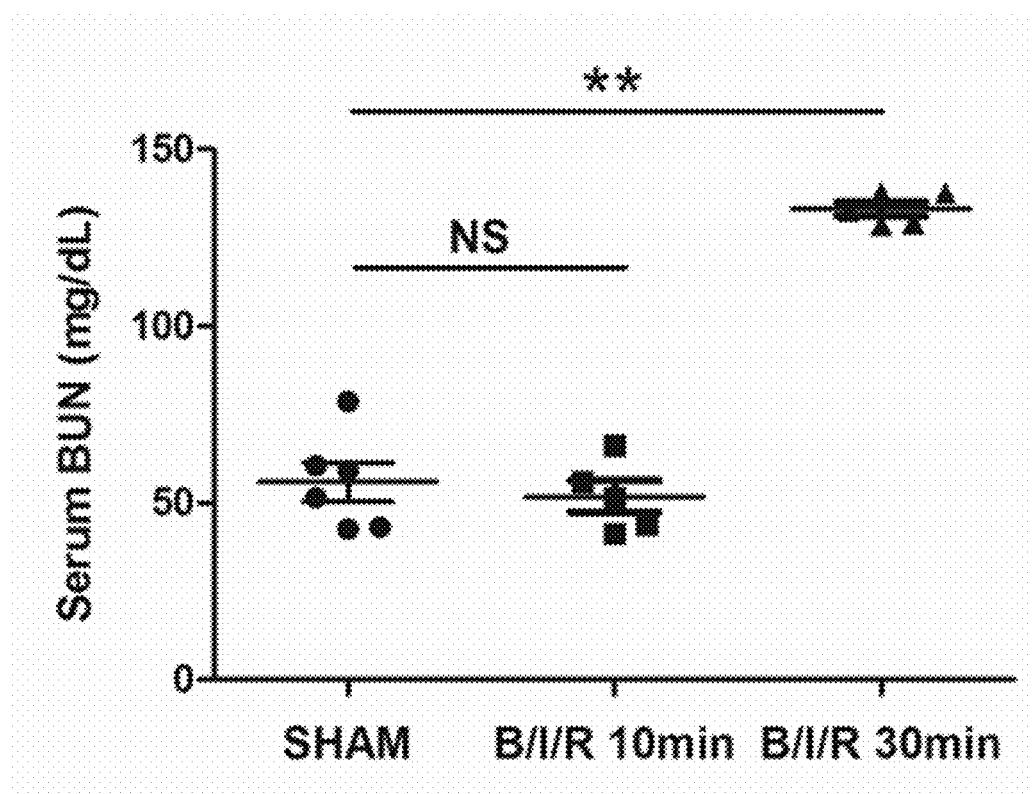
Figure 11J:
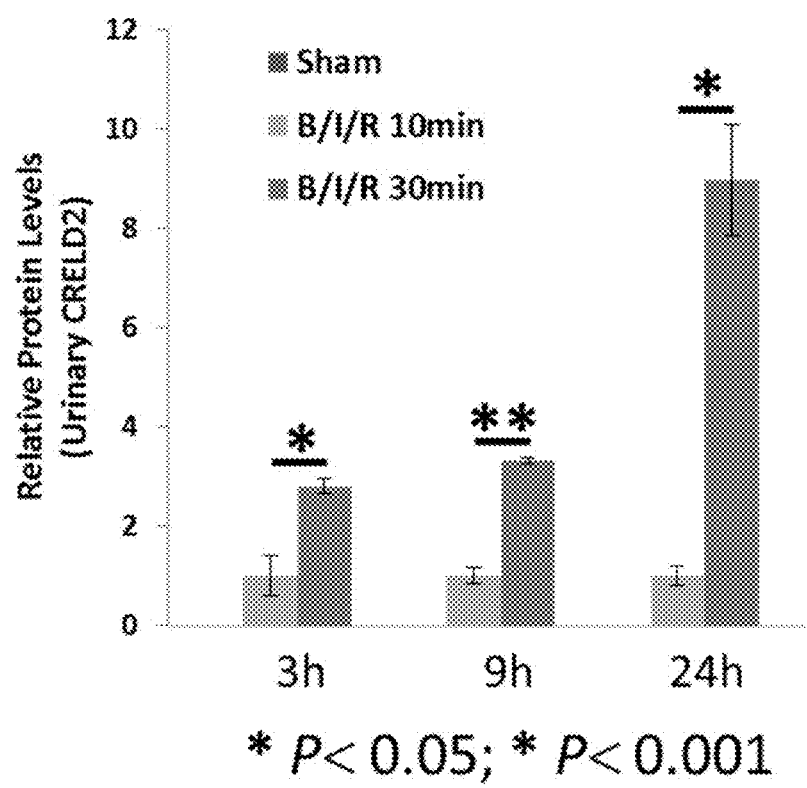
Figure 11K:
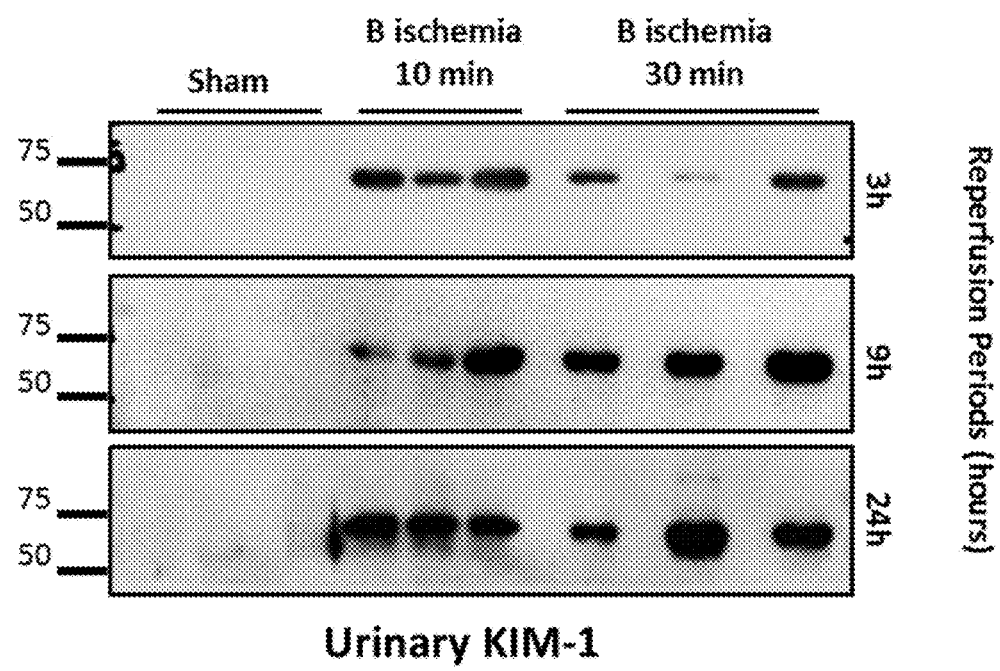

To further confirm that urinary CRELD2 excretion correlates with the disease severity, a bilateral ischemia 10 min model was utilized, which causes subclinical renal I/R injury (see e.g., FIG. 11G, FIG. 11H). At 24 h of reperfusion, compared with mice with 30 min bilateral ischemia, mice with 10 min bilateral ischemia did not manifest any histological or renal functional changes (see e.g., FIG. 11G, FIG. 11H). Urinary CRELD2 excretion was detected as early as 3 h of reperfusion in subclinical renal I/R injury even when post-ischemic kidneys did not show any evidence of kidney function decline or histologic changes. In addition, urinary CRELD2 levels correlated with severity of the ischemic injury (see e.g., FIG. 11I, FIG. 11J).

Figure 11L:
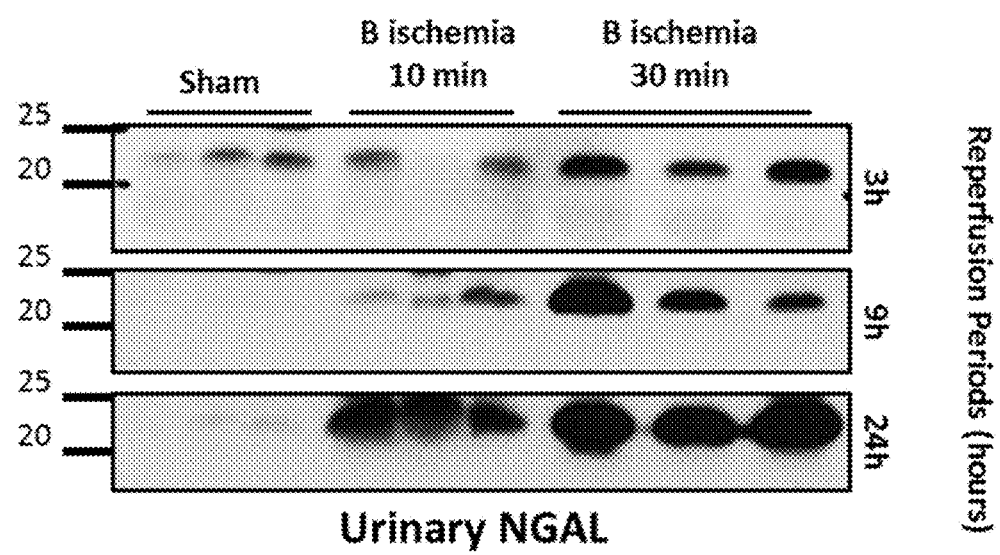

CRELD2 was compared to two known AKI biomarkers Kim-1 (see e.g., FIG. 11K) and NGAL (see e.g., FIG. 11L). These data clearly demonstrated the superiority of CRELD2 compared to Kim-1 and NGAL. Urinary Kim-1 excretion did not show significant difference between bilateral ischemia 10 min model and 30 min model at different reperfusion time points (see e.g., FIG. 11K). Although the level of urinary NGAL excretion showed difference between bilateral ischemia 10 min and 30 min injury at reperfusion of 3 h, 9 h and 24 h, there was no difference at 3 h of reflow between mice following bilateral ischemia 10 min and those with sham-operation (see e.g., FIG. 11L).

Together, these results clearly indicate that urinary CRELD2 excretion can serve as a mechanistic biomarker for ER-stressed tubular cells in the early phase of I/R-induced AKI and its excretion in the urine correlates with the severity of the ischemic injury.

(iv) CRELD2 Levels are Markedly Increased in Patients with ADTKD Caused by Mutations in UMOD The above data identified CRELD2 as a novel urinary ER stress biomarker in mouse models. These exciting results prompted further investigations into the utility of CRELD2 to serve as a urinary biomarker for monitoring kidney cell ER stress in human kidney diseases. ADTKD caused by UMOD mutations is a prototypical tubular ER stress disease.

Figure 12A:
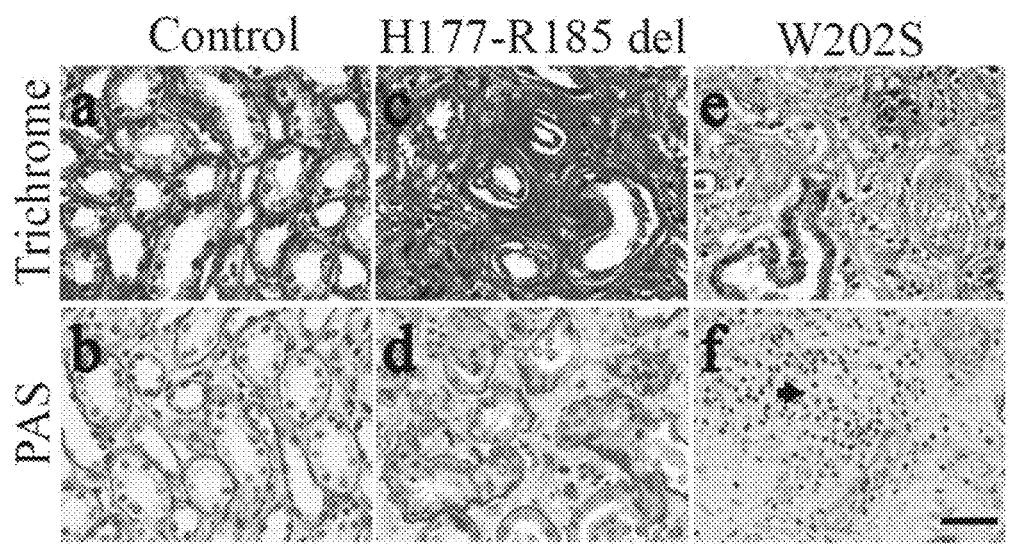
FIG. 12A-FIG. 12E is a series of images showing detection of CRELD2 in the urine from human ADTKD-UMOD patients caused by uromodulin (UMOD) mutations.
Figure 12B:
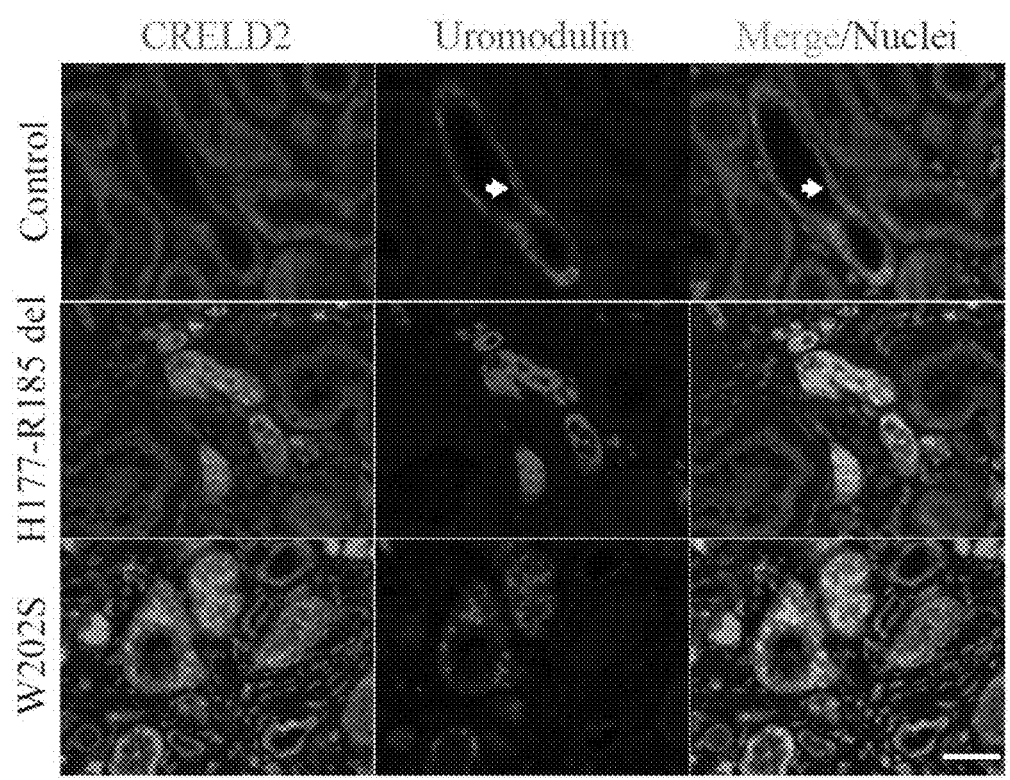
Figure 12C:
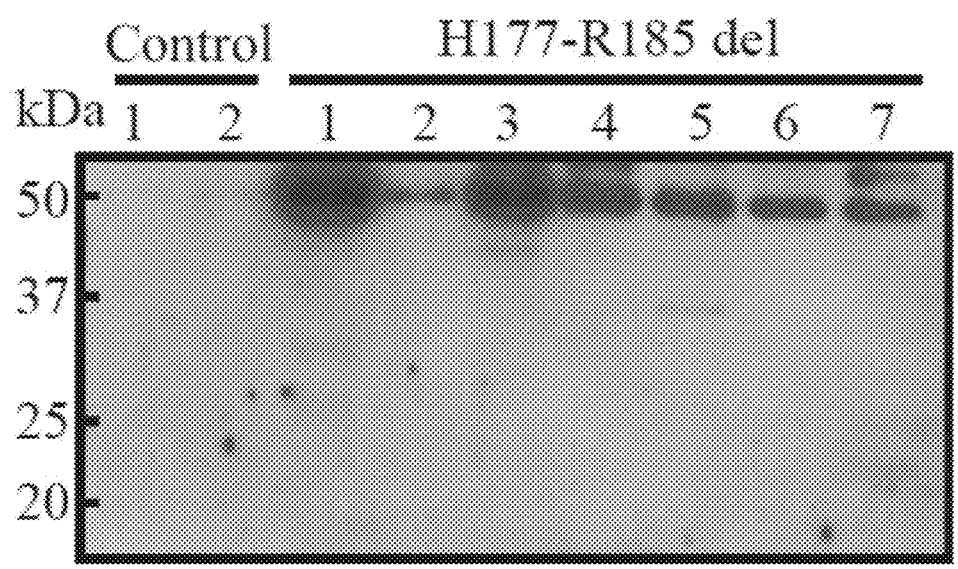
Figure 12D:
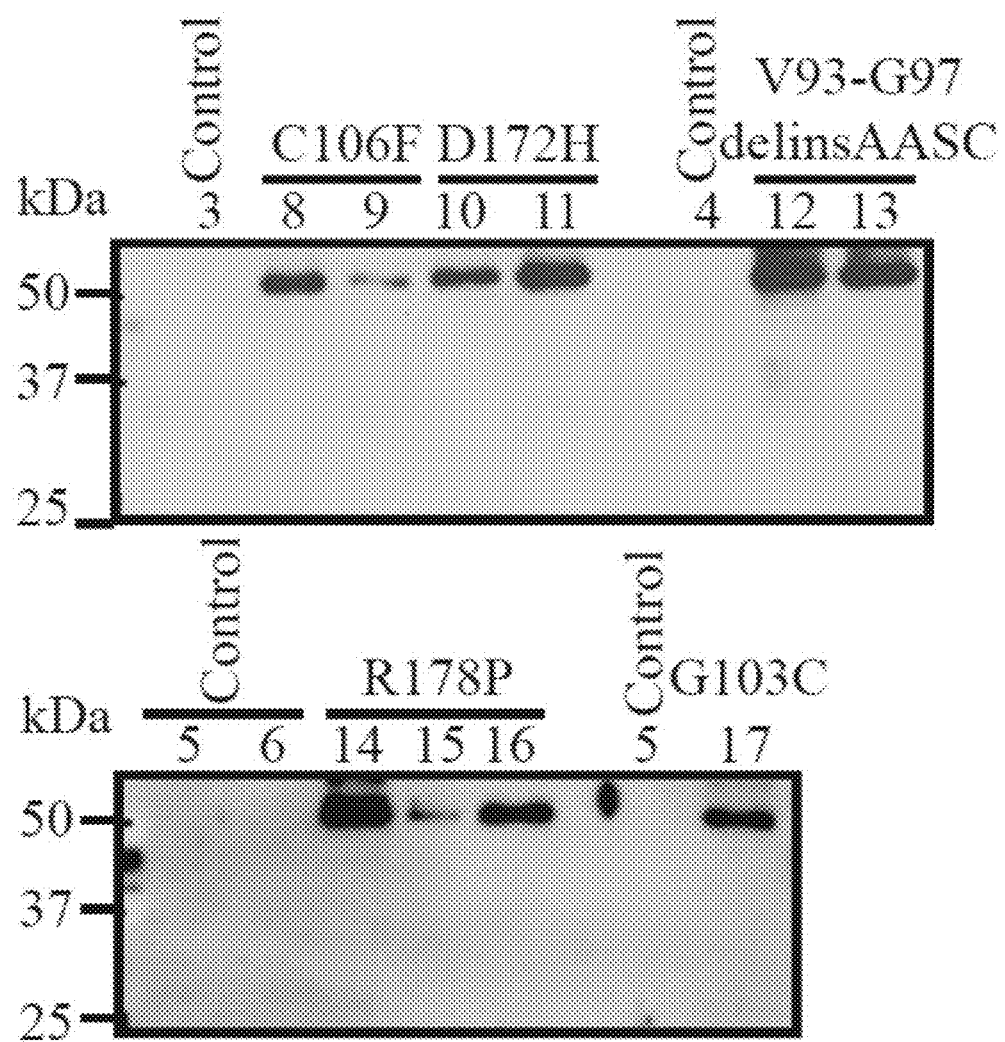
Figure 12E:
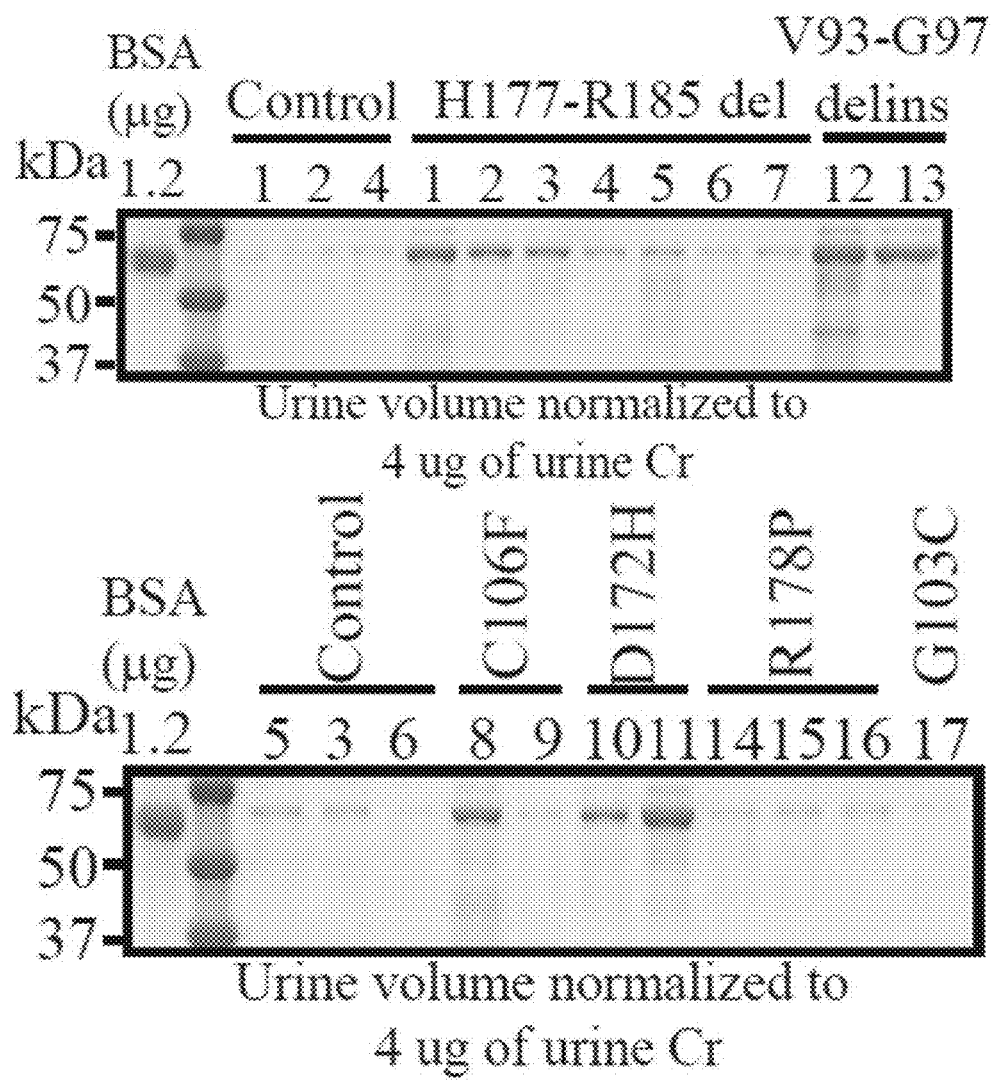

Consistent with prior studies of many mutations causing ADTKD-UMOD, trichrome staining of kidney biopsies from patients carrying the UMOD mutation H177-R185 del or W202S revealed significant interstitial fibrosis (see e.g., FIG. 12A, (c) and (e)). In addition, PAS staining showed tubular dilation, tubular atrophy with tubular basement membrane thickening (see e.g., FIG. 12A(d)) or interstitial inflammatory monocyte infiltration (see e.g., FIG. 12A(f)). Co-If staining of CRELD2 and uromodulin in human kidney biopsies were employed to assess protein expression and localization in renal epithelial cells lining the TAL. In agreement with previous studies with other UMOD mutations (14, 15, 17), native uromodulin was enriched at the apical membrane of TAL cells (see e.g., FIG. 12B, arrows). In sharp contrast, mutant H177-R185del uromodulin exhibited diffuse expression in the cytoplasm of TAL tubules and mutant W202S uromodulin displayed a punctate perinuclear distribution within TAL cells (see e.g., FIG. 12B). Intracellular and intraluminal protein aggregates were also noted in kidney biopsies harboring both mutations, reminiscent of defective intracellular trafficking and ER retention of uromodulin mutants (see e.g., FIG. 12B). Moreover, expression of ER stress response protein CRELD2 was markedly enhanced and completely co-localized with mutant uromodulin in TAL cells (see e.g., FIG. 12B). It was next determined if CRELD2 concentrations were elevated in the urine of ADTKD-UMOD patients. CRELD2 was easily detected in as little as 3-4 µl of unconcentrated urine from human ADTKD-UMOD patients (17 affected individuals from 13 different families carrying 6 different UMOD mutations), whereas urinary CRELD2 excretion was absent from all tested genetically unaffected controls (see e.g., FIG. 12C, FIG. 12D and TABLE 1). Of note, CRELD2 induction was observed in the urine of patients 4, 5, 9, 14 and 15 whose estimated glomerular filtration rate (eGFR) was 111.19, 66.34, 102.9, 75.79 and 66.4 ml/min, respectively (see e.g., FIG. 12 and TABLE 1). As expected, all urine samples from these ADTKD-UMOD patients showed trace to mild albuminuria (urinary albumin to Cr ratio (UACR) less than 300 µg/mg) when urine volume containing 4 µg of Cr was loaded to a gel and the density of the band was compared to that of 1.2 µg of bovine serum albumin (BSA) by Coomassie G-250 stain (see e.g., FIG. 12E), which excludes the possibility that tubular ER stress was due to heavy albuminuria. These results demonstrate the superb ability of CRELD2 to discriminate between controls and ADTKD patients with tubular ER stress.

TABLE 1. Clinical features of genetically unaffected controls and ADTKD patients harboring UMOD mutations Sex: M, Male; F, Female. Race: W, White; n/a, data not available. Age: yr, year.

|  | | UMOD mutation | Sex | Race | eGFR (ml/min) | Age at the listed eGFR (yr) | Age at the urine collection (yr) |
|---|---|---|---|---|---|---|---|
| Controls | 1 | — | M | W | n/a | n/a | 41 |
|  | 2 | — | F | W | 121.99 | 50 | 50 |
|  | 3 | — | M | W | 98.15 | 21 | 21 |
|  | 4 | — | M | W | 82.58 | 32 | 32 |
|  | 5 | — | M | n/a | n/a | n/a | 12 |
|  | 6 | — | M | W | 126.26 | 21 | 21 |
| Patients | 1 | p.H177-R185del | M | n/a | 8.79 | 29 | 29 |
|  | 2 | p.H177-R185del | M | W | 28.38 | 58 | 58 |
|  | 3 | p.H177-R185del | F | W | 21.34 | 39 | 39 |
|  | 4 | p.H177-R185del | F | W | 111.19 | 15 | 15 |
|  | 5 | p.H177-R185del | F | W | 66.34 | 16 | 17 |
|  | 6 | p.H177-R185del | F | W | 30.72 | 36 | 36 |
|  | 7 | p.H177-R185del | F | W | 33.37 | 52 | 52 |
|  | 8 | p.C106F | F | W | 20.11 | 47 | 48 |
|  | 9 | p.C106F | F | n/a | 102.9 | 30 | 30 |
|  | 10 | p.D172H | M | W | 45.12 | 53 | 53 |
|  | 11 | p.D172H | M | W | 27.14 | 53 | 53 |
|  | 12 | p.V93-G97delinsAASC | F | W | ESRD | 35 | 36 |
|  | 13 | p.V93-G97delinsAASC | M | W | 20.5 | 61 | 61 |
|  | 14 | p.R178P | F | W | 75.79 | 33 | 33 |
|  | 15 | p.R178P | F | W | 66.4 | 35 | 35 |
|  | 16 | p.R178P | F | W | 51.55 | 29 | 29 |
|  | 17 | p.G103C | F | W | 27.71 | 28 | 30 |

Figure 13A:
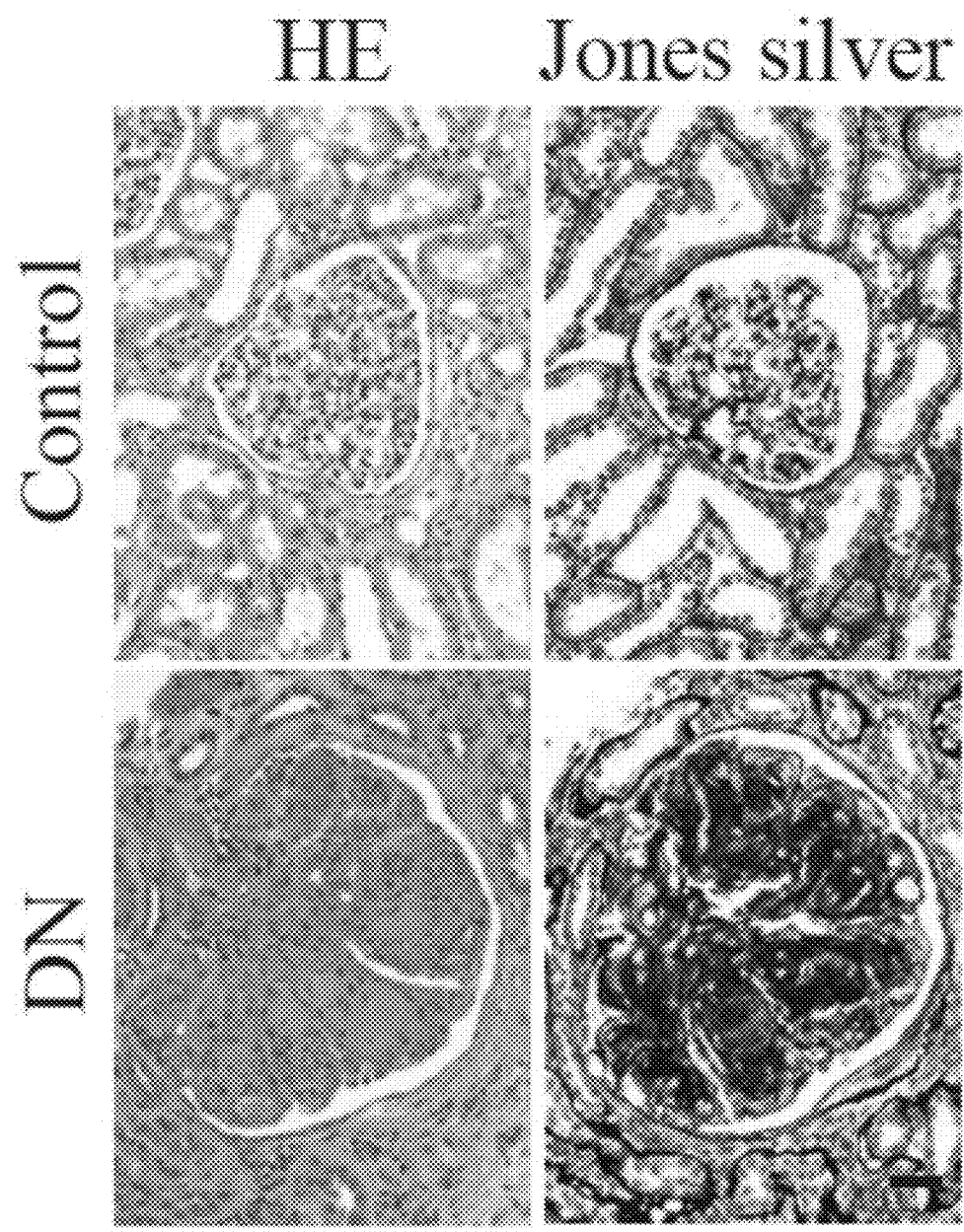
FIG. 13A-FIG. 13F is a series of images showing the detection of CRELD2 in the urine from human DN patients.
Figure 13B:
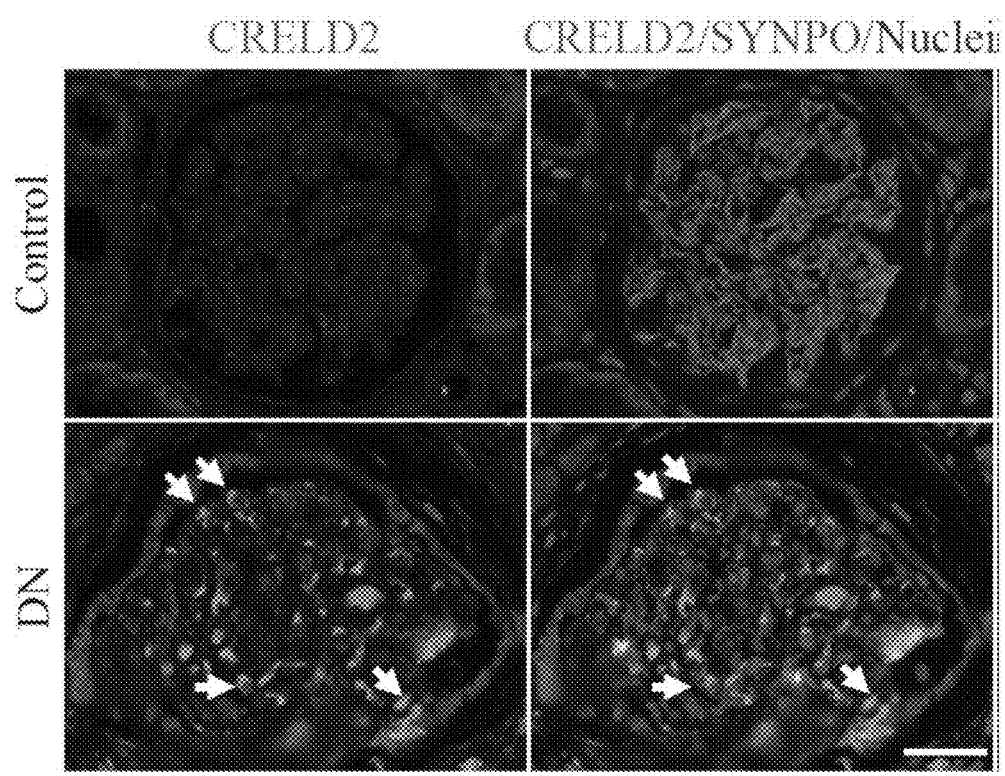
Figure 13C:
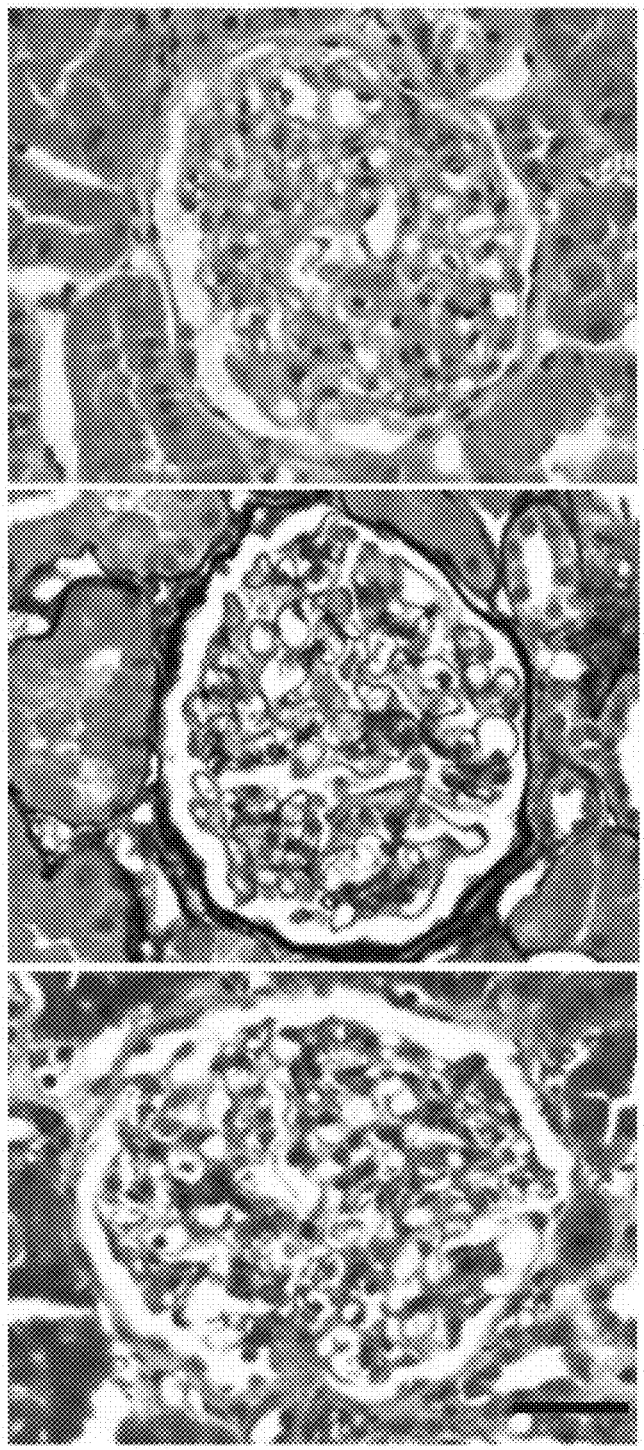
Figure 13D:
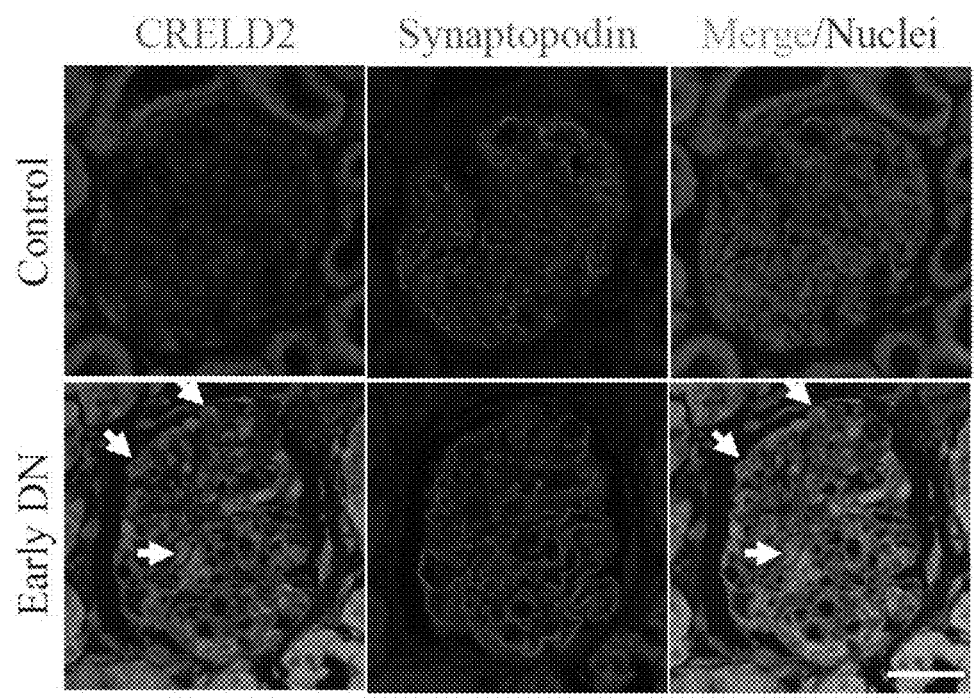
Figure 13E:
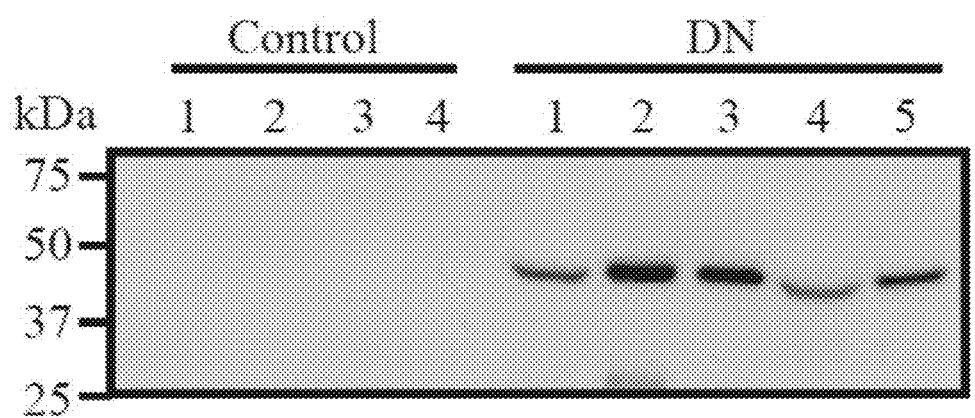
Figure 13F:
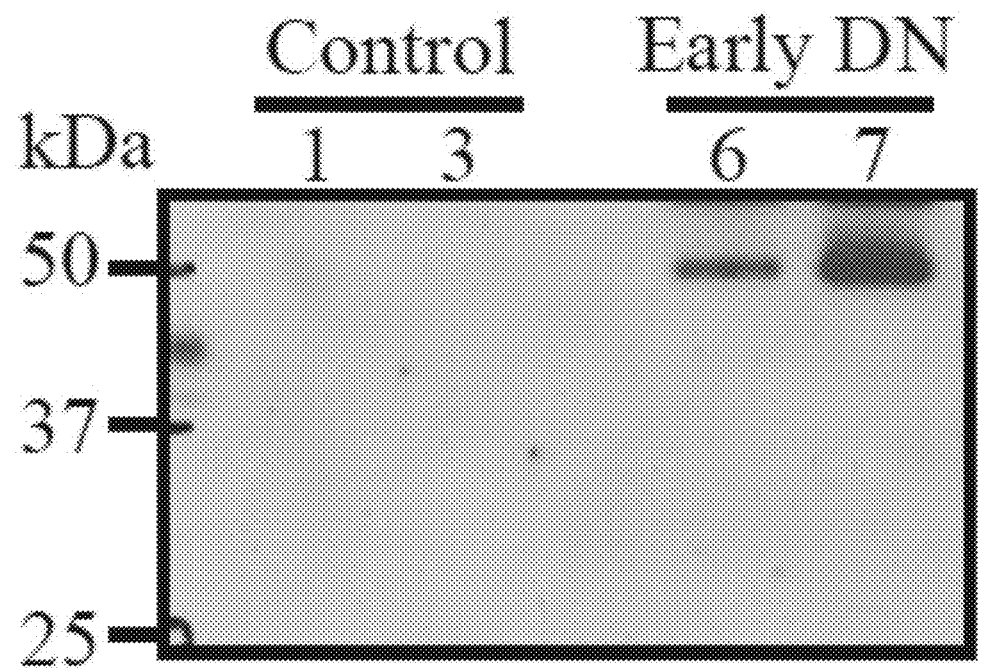

(v) CRELD2 Levels are Significantly Elevated in Patients with Diabetic Nephropathy Podocyte ER dysfunction and subsequent injury induced by impaired podocyte insulin signaling coupled with the metabolic milieu have been shown to be a key determinant of human DN and glomerulosclerosis (9, 32), the leading cause of ESRD. Thus, it presents an urgent need to develop sensitive mechanistic biomarkers for early therapeutic intervention. To determine the relevance of CRELD2 in human DN, kidney biopsy samples of seven patients with DN as well as normal kidney sections of four nephrectomy samples were obtained (see e.g., TABLE 2). Based on glomerular classification of DN (33), patients 1-5 either have nodular glomerular sclerosis (class III) or advanced diabetic glomerulosclerosis (class IV) (see e.g., TABLE 2). As illustrated by FIG. 13A, representative histology from patient 3 showed glomerulomegaly and nodular diabetic glomerulosclerosis. Patients 6-7 with macro- or micro-albuminuria and normal renal function exhibited early DN pathological changes either with histologically unremarkable findings in patient 6 (class I, see e.g., FIG. 13C and TABLE 2) or with mild mesangial expansion in glomeruli in patient 7 (class IIa, see e.g., TABLE 2). The co-localization of CRELD2 with the podocyte marker synaptopodin (SYNPO) was consistent with its induction in the podocytes of diabetic glomeruli compared with normal podocytes (see e.g., FIG. 13B, FIG. 13D). Notably, this induced CRELD2 appeared in a perinuclear ER distribution which was surrounded by SYNPO staining within podocytes (see e.g., FIG. 13B, FIG. 13D, arrows). It was also noted that SYNPO staining was reduced in diabetic glomeruli with more advanced stages when compared to that in normal glomeruli (see e.g., FIG. 13B) whereas its staining in early DN kidney sections was indistinguishable from that in normal kidney sections (see e.g., FIG. 13D). Importantly, the urinary excretion of CRELD2 was significantly increased in patients with both more advanced (see e.g., FIG. 13E) and early DN with delayed appearance (see e.g., FIG. 13F), but not in controls. Collectively, these results suggest that CRELD2 secreted from ER-stressed diabetic podocytes can be captured in the urine from DN patients.

TABLE 2. Clinical and demographic data for healthy controls and DN patients at the time of kidney biopsy and urine collection. Age: yr, year. Sex: M, Male; F, Female. Race: AA, African American; W, White. Proteinuria: n/a, data not available. HbA1c: hemoglobin A1c.

|  | ID | Age (yr) | Sex | Race | Proteinuria (g/day) | UACR (mg/g) | Serum Cr | HbA1c (%) | Albumin (mg/dl) | Kidney biopsy findings |
|---|---|---|---|---|---|---|---|---|---|---|
| Controls | 1 | 12 | F | AA | — | — | 0.4 | — | 4.4 | n/a |
|  | 2 | 39 | M | W | — | — | n/a | — | n/a | n/a |
|  | 3 | 34 | M | W | — | — | n/a | — | n/a | n/a |
|  | 4 | 48 | M | W | — | — | n/a | — | n/a | n/a |
| DN Patients | 1 | 23 | F | W | 9.76 | n/a | 2.37 | 8.5 | 2.6 | Nodular glomerular sclerosis (class III) |
|  | 2 | 69 | M | W | 10.2 | n/a | 2.37 | n/a | 3.8 | Advanced diabetic glomerulosclerosis (class IV) |
|  | 3 | 26 | F | W | n/a | 58 | 1.4 | 9.2 | 3.8 | Nodular glomerular sclerosis (class III) |
|  | 4 | 63 | M | W | 1.7 | n/a | 3.44 | 6.7 | 2.9 | Nodular glomerular sclerosis (class III) |
|  | 5 | 60 | M | AA | 0.718 | n/a | 3.66 | 8.2 | 3.9 | Nodular glomerular sclerosis (class III) |
|  | 6 | 17 | M | W | 0.47 | 356 | 0.6 | 7.8 | 4.6 | Early DN (class I) |
|  | 7 | 10 | F | W | 0.38 | 240 | 0.4 | 11.8 | 3.6 | Early DN (class IIa) |

(vi) Human Pediatric Acute Kidney Injury (AKI) Patients after Cardiopulmonary Bypass Surgery This example describes data obtained for human pediatric AKI patients after cardiopulmonary bypass surgery.

AKI is a frequent complication of pediatric cardiac surgery and negatively effects short- and long-term outcomes. Despite decades of research, no therapy has proven effective for the prevention or treatment of human AKI. Serum creatinine, the traditional marker of renal function, only rises appreciably after a 50% loss in kidney function. Serum creatinine is also affected by several nonrenal factors and on average does not peak until 2 days after cardiac surgery.

Two groups of patients after cardiac surgery were studied: no AKI and severe AKI. Severe AKI was defined by either receipt of acute dialysis or postoperative doubling of serum creatinine during hospital stay.

Figure 14A:
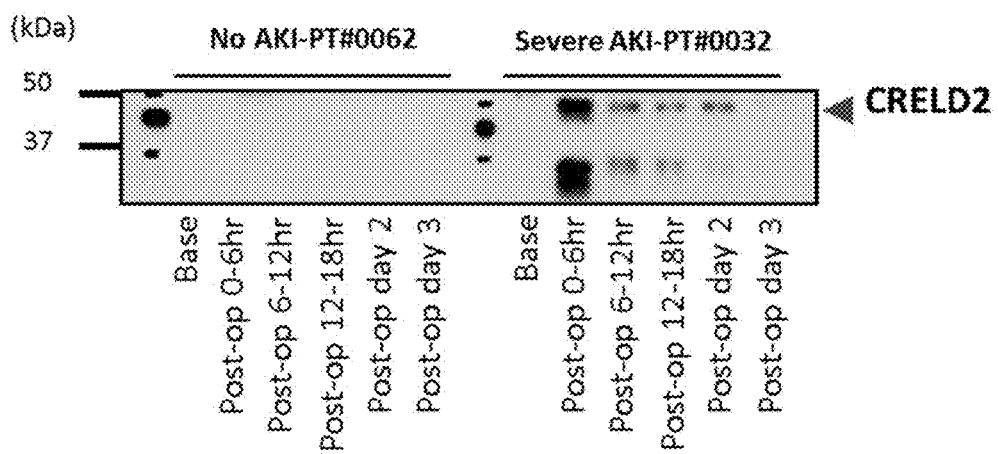
FIG. 14A-FIG. 14C are a series of Western blots showing urinary CRELD2 excretion in human pediatric patients undergoing cardiac surgery. Urine CRELD2 peaked at early as post-op 0-6 hours in the severe AKI group, whereas CRELD2 excretion was not detected in the urine of no AKI group. It demonstrates that early postoperative urine CRELD2 levels are associated with severe AKI and can predict which patient would develop severe AKI following cardiac surgery.
Figure 14B:
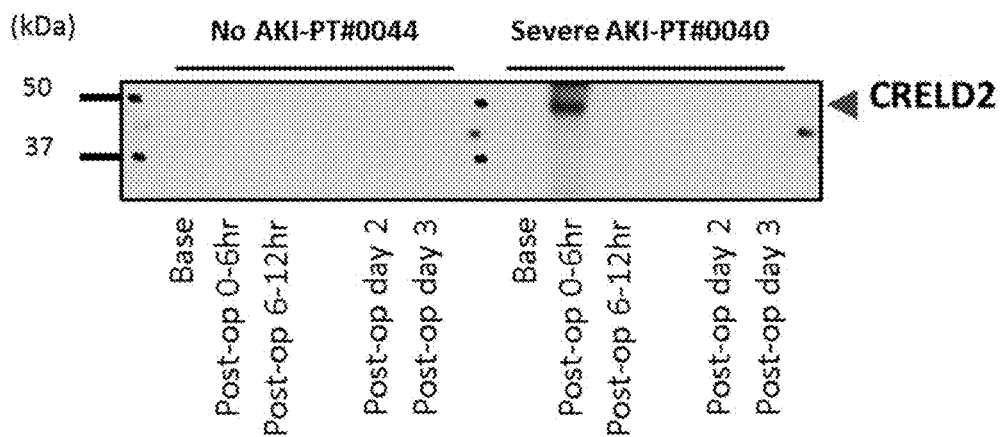
Figure 14C:
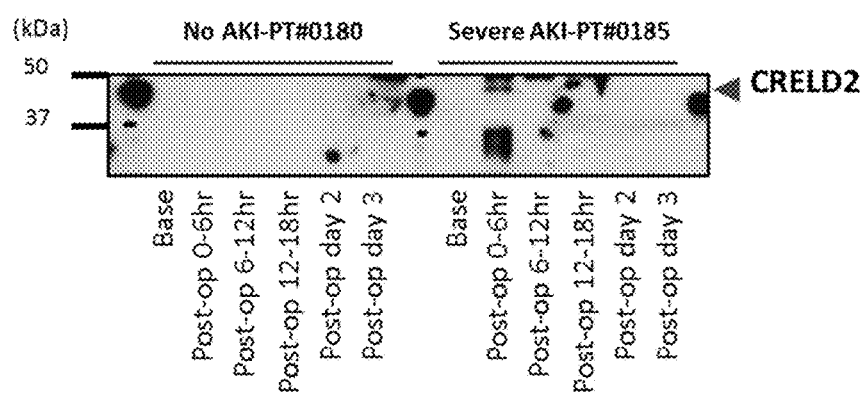

Urinary CRELD2 excretion peaked at early as post-op 0-6 hours in the severe AKI group, whereas CRELD2 excretion was not detected in the urine of no AKI group (see e.g., FIG. 14A-FIG. 14C).

This study demonstrates early postoperative urine CRELD2 levels are associated with severe AKI and can predict which patient would develop severe AKI following cardiac surgery later.

(vii) Discussion

This example is the first to show that CRELD2 represents an early, sensitive, noninvasive, and mechanistic biomarker in the urine for ER stress-mediated kidney diseases. Although growing evidence has highlighted that aberrant ER protein proteostasis and ER dysfunction underpin the initiation and/or development of a variety of glomerular and tubular diseases, ER stress biomarkers that can be applied in human kidney disease patients are still lacking. Here, it was demonstrated that CRELD2 was rapidly upregulated and secreted when renal cells were subjected to ER stress by utilizing mouse models of podocyte ER stress-induced NS and TM- or I/R-induced AKI. Moreover, CRELD2 was detectable in small aliquots of urine early in the disease course, often preceding clinical or histologic manifestation of the corresponding disease. Finally, the clinical utility of CRELD2 as a urine ER stress biomarker was validated in patients with kidney diseases associated with ER stress. The discriminative ability of urinary CRELD2 excretion to differentiate patients having ER stress from human controls is outstanding.

The use of CRELD2 as an ER stress biomarker in the kidney has many promising applications. Serum Cr—the primary marker of kidney disease and kidney function—only increases after approximately 25% of kidney function has been lost. When elevations of serum Cr occur, irreversible changes such as scarring and fibrosis of the kidney are often present, and treatment is unlikely to restore full kidney function. In contrast, the best markers are those that are associated with the central underlying pathogenesis of the disorder. These biomarkers will be elevated early on in the disease prior to loss of kidney function and elevations of serum Cr, and treatments that target the same pathogenesis of the disease will have an effect on these markers.

Thus, these mechanistic markers will allow the initiation of treatments early on in the disease and will allow one to detect the effect of interventions early on—dramatically reducing the amount of follow up time to determine treatment efficacy and making clinical trials much easier and less expensive to perform. In the current investigation, CRELD2 showed it can be such a biomarker. An ELISA assay can be used for measuring urinary excretion of CRELD2 (spot urinary CRELD2/Cr ratios) with absolute quantification and higher throughput, which will increase assay efficiency and enable widespread implementation in large-scale investigations.

An important implication of this study relates to early detection of tubular ER stress, which will be helpful in the development of mechanism-based treatment in AKI. Approximately 45% of critically ill patients and 20% of hospitalized patients develop AKI (34), which leads to increased hospital stays, infectious complications, and increased mortality, at significant cost (35, 36). In addition, AKI has been associated with future development of chronic kidney disease (37). For the early diagnosis of AKI, although significant progress has been made to discover blood and urine biomarkers including neutrophil gelatinase-associated lipocalin (NGAL), KIM-1, interleukin (IL)-18, cystatin C, α/β glutathione S-transferase (GST), liver type fatty acid-binding protein 1 (FABP1), and N-acetyl-β-D glucosaminidase (NAG) (38), very few of these biomarkers pinpoint to the underlying pathophysiology of AKI and none of them can capture the presence of tubular ER stress, which has been causally linked to AKI.

This study lead to validating this candidate biomarker in human patients undergoing cardiopulmonary bypass or renal transplantation, which mechanistically mimics the mouse I/R model, in prospective cohorts (see e.g., Example 2, section (vi)). The ultimate utility of CRELD2 is to identify an early therapeutic window during which a tubular ER stress modulators can be applied before a detectable change in function occurs. Considering the complexity of pathways involved in AKI, incorporation of different biomarkers that target distinct pathophysiological mechanisms together with CRELD2 into the diagnostic or prognostic panel may be required to profile the multifaceted response of the kidney to insults and thus to design combinational mechanism-based treatments in AKI.

Another important clinical implication of these findings pertains to determining the pathogenicity and assessing the functional impact of podocyte-specific genetic variations identified in genetic forms of NS and AS. Human genetic studies in the past two decades have illuminated podocyte dysfunction as the major contributor to GFB failure in primary NS. Mutations in more than 30 podocyte genes including NPHS1, NPHS2, WT-1, LAMB2, CD2AP, TRPC6, ACTN4, INF2 and COL4A have been implicated as causal factors for primary podocytopathy and GBM nephropathy (39). With the recent advent of next-generation sequencing, a large number of rare (minor allele frequency <0.5%) missense variants of unknown significance in both known and novel NS-causing podocyte genes are rapidly emerging in thousands of affected patients (40, 41). Without family data for segregation analysis in patients with de novo mutations, and with a sole reliance on bioinformatics-based prediction algorithms, reliably assigning pathogenicity to these genetic variants is challenging (42). In addition, in silico prediction of deleterious or damaging variants may not be completely accurate (43, 44) and more importantly cannot provide much mechanistic information. Detection of CRELD2 in urine may serve as a powerful high-throughput tool to functionally screen patients carrying rare genetic variants for causation of ER stress and thus may institute the targeted therapy at the early stage.

The identification of CRELD2 as an ER stress biomarker for ADTKD-UMOD is extremely important to research in this area. ADTKD is monogenic tubulointerstitial fibrosis that has important implications for understanding the pathogenesis of renal fibrosis and progression of chronic kidney disease. ADTKD-UMOD is a phenotypically heterogeneous disorder manifested by variable age of disease onset, disease severity and rate of disease progression among affected individuals within and between families and in the end it reaches ESRD between the ages of 25 and 70 years or older (12). Human mature uromodulin, mainly localized at the apical plasma membrane of TAL cells (45), contains a signal peptide, three EGF-like domains, a central domain of unknown function, a zona pellucida domain, and a glycosylphosphatidylinositol (GPI)-anchoring site (13). Uromodulin has extremely high cysteine content and extensive disulfide bond formation resulting in extremely slow transit through the ER. After being cleaved by a protease hepsin (46), uromodulin is released to the urine. UMOD mutations are clustered (94%) in exons 3 and 4 encoding for the N-terminal half of the protein and ~50% of known UMOD mutations affect cysteine (13). All mutations listed in TABLE 1 involve exon 3. No clear genotype-phenotype relationship in human patients has been established so far. Studies in cellular models and mouse genetic models as well as findings in patient renal biopsies have demonstrated that UMOD mutations lead to mutant protein retention and aggregation in the ER, likely due to protein misfolding (14-18). The activation of the UPR leads to progressive damage of TAL, triggering inflammation and interstitial fibrosis (47).

It is important to note that CRELD2 elevation in the urine was detected in ADTKD-UMOD patients with eGFR >60 ml/min, especially in two patients (patients 4 and 9) with normal eGFR. Thus, urinary excretion of CRELD2 may enable identification of disease activity early in the course of disease and allow for the monitoring of the effects of therapy, overcoming the challenge posed by the slow rates of rise in serum Cr in these individuals, which is the major reason that currently clinical trials in ADTKD-UMOD cannot be performed. A prospective longitudinal cohort will be assembled in asymptomatic UMOD mutation-carriers or ADTKD-UMOD patients with normal kidney function (eGFR 90 ml/min) to determine whether urine CRELD2 excretion occurs early in the disease course and correlates with disease onset, severity and progression as well as treatment response. Meanwhile, a larger cross-sectional cohort will be carried out to discern whether there is any correlation between urinary CRELD2 levels and clinical phenotypes.

In summary, this study has identified CRELD2 as a sensitive mechanistic urine biomarker in various ER stress-mediated kidney diseases, including glomerular disorders such as congenital NS and DN, as well as tubulointerstitial disorders such as AKI and ADTKD-UMOD. CRELD2 can be very valuable in the study of ER stress not only in these disorders but many other kidney disorders as well. The broad clinical applications of CRELD2 in ER dysfunction-mediated kidney diseases may include early diagnosis, stratification of patients at risk, monitoring treatment response and guiding ER stress modulator development in targeted patient groups.

(viii) Methods

Antibodies and reagents. Commercially available antibodies were obtained as follows: goat anti-mouse CRELD2 antibody was from R&D (Minneapolis, Minn.), rabbit anti-mouse CRELD2 antibody crossreacting with human was from Santa Cruz (Santa Cruz, Calif.) and rabbit anti-human CRELD2 antibody was from LSBio (Seattle, Wash.). Rabbit anti-mouse BiP antibody was from Proteintech (Chicago, Ill.). Mouse anti-human uromodulin antibody was from RayBiotech (Norcross, Ga.). Mouse IgG1 anti-human synaptopodin antibody was purchased from Fitzgerald (Acton, Mass.). Horseradish peroxidase (HRP)-conjugated anti-mouse β actin antibody was from Sigma (St. Louis, Mo.). Alexa 488- and Alexa 594-conjugated secondary antibodies were purchased from Molecular Probes (Carlsbad, Calif.). HRP-conjugated anti-rabbit and anti-goat secondary antibodies were from Santa Cruz. Biotinylated LTL and anti-mouse antibody were from Vector Laboratories (Burlingame, Calif.). Alexa 594-conjugated streptavidin was purchased from ThermoFisher (Waltham, Mass.). Hoechst 33258 was from ThermoFisher. Histochoice was purchased from Amresco (Solon, Ohio). Rat collagen I was from Trevigen (Gaithersburg, Md.). Tunicamycin, thapsigargin and acetic acid were from Sigma (Saint Louis, Mo.).

Mice.

The Lamb2 null, WT and mutant transgenic mice have all been described previously (5, 28). C57BL/6J mice were obtained from The Jackson Laboratory.

TM-Induced AKI Mouse Model.

TM was dissolved in DMSO at 2 mg/ml, and injected intraperitoneally at 1 mg/kg into 6-10 weeks old C57BL/6J mice. Urine was collected from metabolic cages in which the mice were immediately placed after the injection. 1 day or 5 days after the injection, sera were obtained, and kidneys were harvested. One kidney was snap frozen in dry ice and stored at −70 C until further processing for protein and RNA. The other kidney was fixed in 4% paraformaldehyde (PFA) (pH 7.4) at 4 C and then transferred to 15% and 30% sucrose/PBS for OCT-embedded cryosections.

Renal Bilateral I/R Mouse Model.

C57Bl/6 mice (20 males at age of 9 weeks) were subjected to bilateral renal ischemia for 10 minutes or 30 minutes. Briefly, mice were anesthetized with isoflurane, their body temperature was maintained at 37° C. on a heating pad, and monitored with a rectal probe throughout surgery. Ischemia was induced by non-traumatic clamping of bilateral renal vascular pedicles for 10 or 30 minutes, during which time the kidneys were kept warm and moist. The clamps were then removed and the kidneys were observed for return of blood flow. Sham-operated C57Bl/6 mice (9 males at age of 9 weeks) underwent an identical procedure without vascular pedicle clamping. Urines were collected from metabolic cages in which the mice were placed immediately after the surgery. 3 hours, 9 hours, 24 hours, 3 days, 7 days, or 14 days after reperfusion, sera were obtained, and kidneys were harvested. One kidney was snap frozen in dry ice and stored at −70 C until further processing for protein and RNA. The other kidney was fixed in Histochoice at 4° C. and then processed for paraffin blocks.

Isolation of Mouse Glomeruli.

Mice were perfused through the heart with magnetic 4.5 μm diameter Dynabeads (Dynabeads M-450 Tosylactivated, Invitrogen, Carlsbad, Calif.). Kidneys were minced into small pieces, digested by collagenase A (Gibco) and DNAse I (Sigma), filtered, and collected using a magnet. The purity of glomeruli was 95-100%.

Primary Podocyte Culture.

Isolated glomeruli from $Lamb2^{+/-}$, $Lamb2^{-/-}$; Tg-C321R and $Lamb2^{-/-}$; Tg-WT mice at P27 were suspended in DMEM/Ham's F-12 (2:1) that contained 0.45 μm-filtered 3T3-L1 supernatant, 5% heat inactivated FBS, ITS (Insulin-Transferrin-Sodium Selenite) liquid media supplement, and 100 U/ml penicillin-streptomycin; plated onto collagen type I-coated petri dishes; and incubated at 37° C. in room air with 5% $CO_2$. After 3 days, cell colonies began to sprout around the glomeruli. These cells (P0) showed an epithelial morphology with a polyhedral shape when confluence was reached and were characterized as podocytes by detection of the podocyte-specific markers, WT-1, nephrin and podocin, by immunofluorescence staining and WB. Only passages 1-2 podocytes from the indicated genotypes were used in the in vitro studies.

Immunofluorescence Staining.

For dual staining of CRELD2 with biotinylated LTL in mouse kidneys, paraffin-embedded sections were used. After dewaxing, PFA-fixed, sucrose-cryoprotected kidney sections from control or TM-treated mice were subjected to antigen retrieval by immersion in 10 mM citric acid buffer (pH 6.0) for 5 minutes at 95 C. Histochoice-fixed kidney sections from sham-operated or I/R injured-mice did not require antigen retrieval. Nonspecific avidin binding was blocked by an avidin/biotin blocking kit (Vector laboratories) before incubating kidney sections with 1% BSA for 30 minutes at room temperature. The slides were stained with a goat anti-mouse CRELD2 antibody (R&D) together with biotinylated LTL overnight at 4° C., followed by an Alexa 488-conjugated anti-goat secondary antibody and Alexa 594-conjugated streptavidin as well as Hoechst 33342. For CRELD2 staining in sham-operated and post-ischemic kidneys, the fluorescent signal was further amplified using a Fluorescein tyramide amplification kit (Perkin-Elmer, Waltham, Mass.) according to the manufacturer's instructions. Slides were analyzed under a fluorescence microscope (Nikon).

Formalin-fixed, paraffin-embedded sections of human kidneys underwent the same process of deparaffinization, antigen retrieval and blocking. The slides were incubated with a rabbit anti-human CRELD2 antibody (LSBio) in combination with a mouse IgG2b antibody against human uromodulin or a mouse IgG1 antibody against human SYNPO. A biotinylated anti-mouse antibody was used to amplify fluorescence signals for uromodulin, followed by Alexa 594-labelled streptavidin. The corresponding Alexa 488- or Alexa 594-conjugated secondary antibodies were used to detect CRELD2 and SYNPO, respectively, with Hoechst 33342 nuclear staining.

For immunocytochemistry, mouse primary podocytes were seeded on cover slips coated with 5 μg/ml rat collagen I that was dissolved in 0.02M acetic acid in 24 well plates for 48 hours. After 24 hours treatment with DMSO, TM or TG, the cells were fixed with 4% PFA for 20 minutes and permeabilized with 1% Triton X-100 for 5 minutes at room temperature, blocked with 1% BSA for 30 minutes at room temperature, followed by incubation with goat anti-mouse CRELD2 (R&D) and rabbit anti-mouse BiP antibodies for an additional 1 hour at room temperature. The cover slips were washed with PBS and incubated with the corresponding Alexa 594- or Alexa 488-conjugated secondary antibodies and Hoechst 33342 to stain nuclei. The cover slips were then mounted with anti-quench solution and visualized using a fluorescence microscope (Nikon).

Light Microscopy.

For light microscopy, mouse kidneys were fixed in 4% PFA or Histochoice and human kidneys were fixed in 10% formalin, dehydrated through graded ethanols, embedded in paraffin, sectioned at 4 μm, and stained with H&E, PAS, Masson's Trichrome or Jones Methenamine Silver by standard methods.

Western Blot Analysis.

Isolated mouse glomeruli and cultured mouse primary podocytes were lysed by RIPA buffer (Sigma) containing protease inhibitor cocktail (Roche, Indianapolis, Ind.). TM untreated- and treated-kidneys, as well as sham-operated and I/R-injured kidneys, were extracted using the same lysis buffer with the protease inhibitors and homogenized by sonication. The protein concentrations of cell, glomerular and kidney lysates were determined by Bio-Rad protein assay (Hercules, Calif.) using BSA as a standard. Denatured proteins were separated on SDS polyacrylamide gel electrophoresis (SDS-PAGE) and then transferred to PVDF membranes. Blots were blocked with 5% non-fat milk for 1 hour and then incubated overnight with primary antibodies. The membranes were washed with Tris-buffered saline/TWEEN® (polysorbate) buffer and incubated with the appropriate HRP-conjugated secondary antibodies. The proteins were then visualized in an x-ray developer using ECL plus detection reagents (GE, Pittsburgh, Pa.). To ensure equal protein loading, the same blot was stripped with stripping buffer (25 mM glycine+1 SDS, pH=2.0) and then incubated with a HRP-conjugated anti-mouse β-actin antibody. Relative intensities of protein bands were quantified using ImageJ (NIH) analysis software.

To determine secretion of CRELD2 from mouse primary podocytes, equal numbers of primary podocytes from the indicated genotypes or treatment groups were plated and their media were harvested after 48 hours of culturing or 24 hours of treatment, respectively. 20 μl of medium from the respective groups was subjected to the WB analysis. To compare urinary CRELD2 excretion, crude urine samples from the indicated groups that were normalized to urinary creatinine were applied to a gel.

mRNA Quantification by Real-Time PCR.

Total RNA from primary podocytes or whole kidneys was extracted using the RNeasy kit (Qiagen, Valencia, Calif.) with subsequent DNase I treatment. 1 μg of cellular or kidney RNA was then reverse-transcribed using an RT-PCR kit (Superscript III; Invitrogen). Gene expression was evaluated by quantitative real-time PCR. One μl of cDNA was added to SYBR Green PCR Master Mix (Qiagen) and subjected to PCR amplification (one cycle at 95 C for 20 seconds, 40 cycles at 95 C for 1 second, and 60 C for 20 seconds) in an Applied Biosystems 7900HT Fast Real-Time PCR System (Life Technologies, Grand Island, N.Y.). Q-PCR was conducted in triplicate for each sample. The sequences of primers were following:

mouse CRELD2 forward: CAACACGGCCAG-GAAGAATTT (SEQ ID NO: 1);

mouse CRELD2 reverse: CATGATCTCCAGAAGCCG-GAT CAACACGGCCAGGAAGAATTT (SEQ ID NO: 2);

mouse WT-1 forward: GAGAGCCAGCCTACCATCC CAACACGGCCAGGAAGAATTT (SEQ ID NO: 3), mouse WT-1 reverse: GGGTCCTCGTGTTTGAAGGAA CAACACGGCCAGGAAGAATTT (SEQ ID NO: 4);

mouse GAPDH forward: TGTAGACCATGTAGTT-GAGGTCA CAACACGGCCAGGAAGAATTT (SEQ ID NO: 5); and mouse GAPDH reverse: AGGTCGGTGTGAACG-GATTTG CAACACGGCCAGGAAGAATTT (SEQ ID NO: 6).

BUN Measurement.

BUN was measured by using a QuantiChrom™ urea assay kit (DIUR-500) (BioAssay Systems, Hayward, Calif.).

Urinalysis.

Mouse urines were collected by manual restraint or using a metabolic cage if 24 hours urine collection was required. The mouse urines were centrifuged at 1800 g for 10 minutes and human urines were spun at 1600 g for 10 minutes to remove debris before being frozen at −70° C. Coomassie G-250 stain was used to visualize urinary albumin (VWR, Radnor, Pa.). Urinary Cr concentration was quantified by a QuantiChrom™ creatinine assay kit (DICT-500) (BioAssay Systems).

Statistics.

Data were expressed as mean±SEM. Statistical analysis was performed using ANOVA with Tukey multiple comparison test. P<0.05 was considered significant.

Study Approval.

All animal experiments conformed to the National Institutes of Health (NIH) Guide for the Care and Use of Laboratory Animals and were approved by the Washington University Animal Studies Committee. Paraffin-embedded tissue blocks from renal biopsies of patients with DN (n=7) and from normal kidney tissues after nephrectomy (n=4), as well as their corresponding urine specimens, were retrieved from Kidney Translational Research Core at Washington University. All human urine samples from ADTKD patients (n=17) and their genetically unaffected controls (n=6), as well as their paraffin-embedded slides, were obtained from Wake Forest Cohort. All specimens used for the research were collected under protocols approved by the Institutional Review Board of Washington University School of Medicine and Wake Forest School of Medicine, respectively.

(ix) Conclusion

These studies (see e.g., Example 2) have identified CRELD2 as a novel urinary ER stress biomarker with utility in identifying the underlying pathogenesis of the disease as a mechanistic biomarker, which is a cornerstone for therapeutic intervention; early diagnosis; risk prediction; monitoring treatment responses or recovery; or developing highly-targeted therapies for ER stress disease in the emerging era of precision medicine.

Example 3: Immunoglobulin Binding Protein (BiP) as a Biomarker for Endoplasmic Reticulum (ER) Stress-Associated Kidney Disease This example describes the discovery of immunoglobulin binding protein (BiP) (a.k.a glucose-regulated protein (GRP)78 or heat shock 70 kDa) as a biomarker for endoplasmic reticulum (ER) stress-associated kidney diseases Endoplasmic reticulum (ER) stress and disrupted proteostasis contribute to the pathogenesis of a variety of glomerular and tubular diseases. Thus, it is imperative to develop noninvasive biomarkers for detecting ER stress in podocytes or tubular cells in the incipient stage of disease, when a kidney biopsy may not yet be clinically indicated. Immunoglobulin binding protein (BiP) localizes to the ER and is secreted in response to ER stress in several cell types.

In human DN patients, autosomal dominant tubulointerstitial kidney disease (ADTKD) and pediatric severe ischemic AKI patients as well as mouse models of human nephrotic syndrome caused by mutant laminin β2 protein-induced podocyte ER stress and acute kidney injury (AKI) triggered by tunicamycin- or ischemia reperfusion-induced tubular ER stress, BiP was shown to be an effective a biomarker for detecting ER stress in podocytes or renal tubular cells. ER stress upregulated BiP expression in podocytes and tubular cells. Notably, urinary BiP excretion, concurrent with podocyte or tubular cell ER stress, preceded clinical or histologic manifestations of the corresponding disease.

(i) BiP as a Biomarker in Diabetic Neuropathy (DN)

Figure 24A:
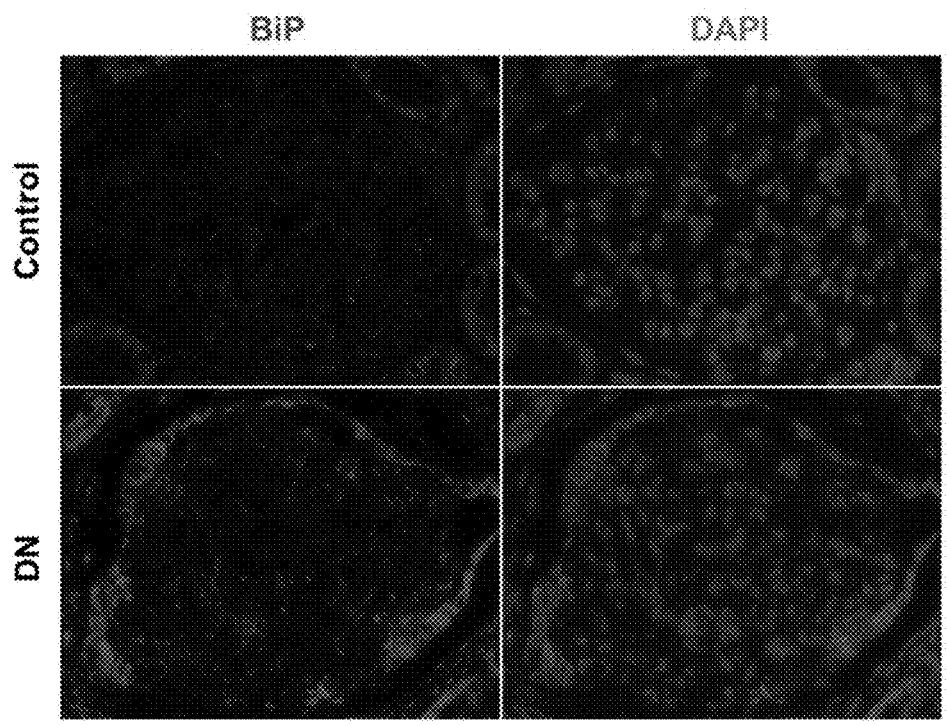
FIG. 24A illustrates that BiP is induced in the podocytes of human diabetic nephropathy (DN) patients.
Figure 24B:
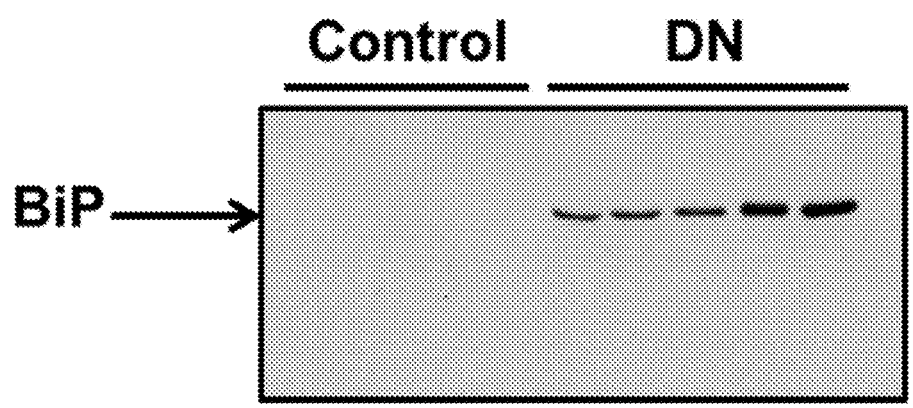
FIG. 24B illustrates that BiP excretion is detected in the urine of Human DN patients with podocyte ER stress.

It was discovered that urinary BiP excretion was detected in human diabetic nephropathy (DN) patients caused by podocyte ER stress, but not in healthy controls. FIG. 24A illustrates immunofluorescence detection of BiP expression in the podocytes of human diabetic nephropathy (DN) patients. FIG. 24B illustrates immunodetection of BiP in urine of human diabetic nephropathy (DN) patients.

(ii) BiP as a Biomarker in Nephrotic Syndrome (NS)

Figure 15A:
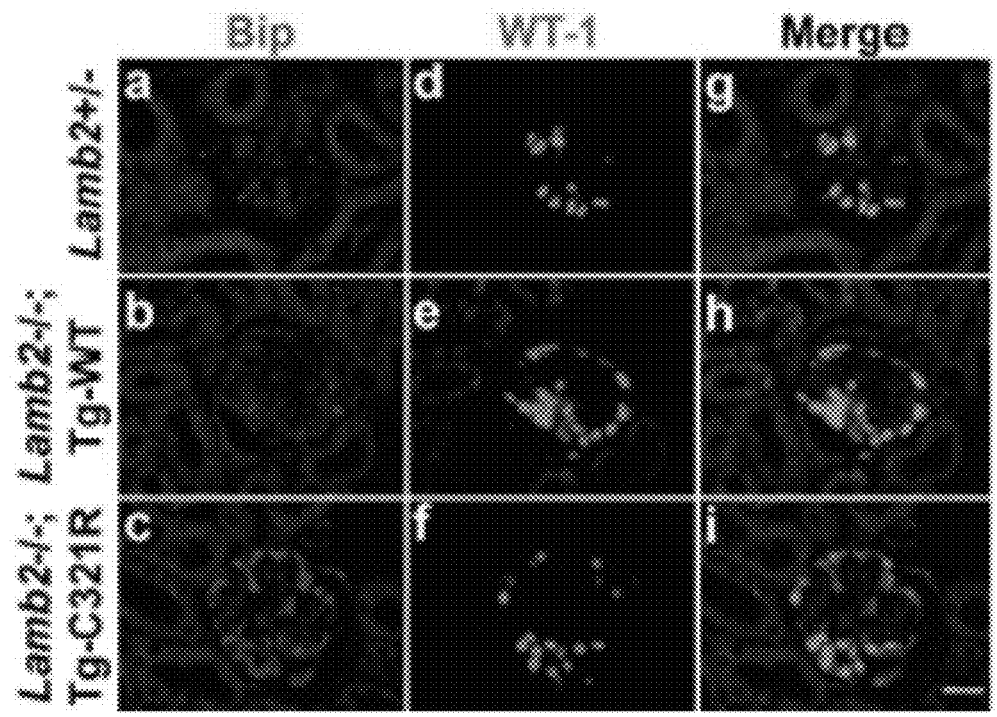
FIG. 15A-FIG. 15C is a series of images, a graph, and a Western blot illustrating that BiP is induced in ER-stressed podocytes in Tg-C321R mice at an early stage of disease.
Figure 15B:
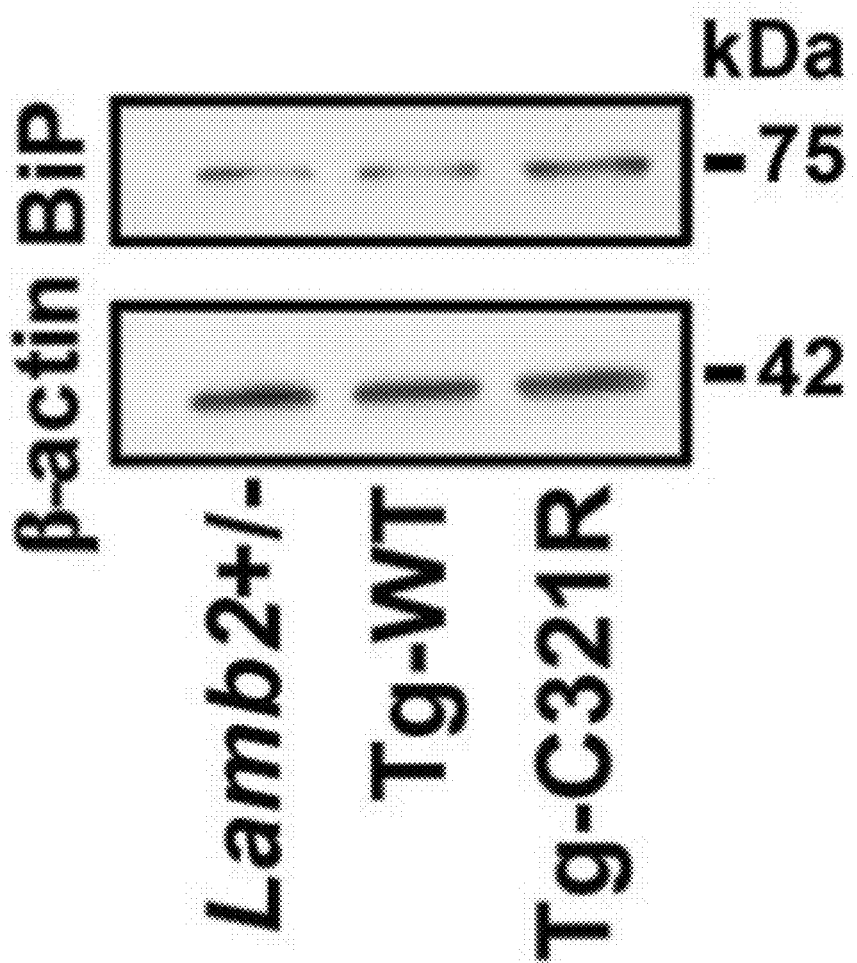
Figure 15C:
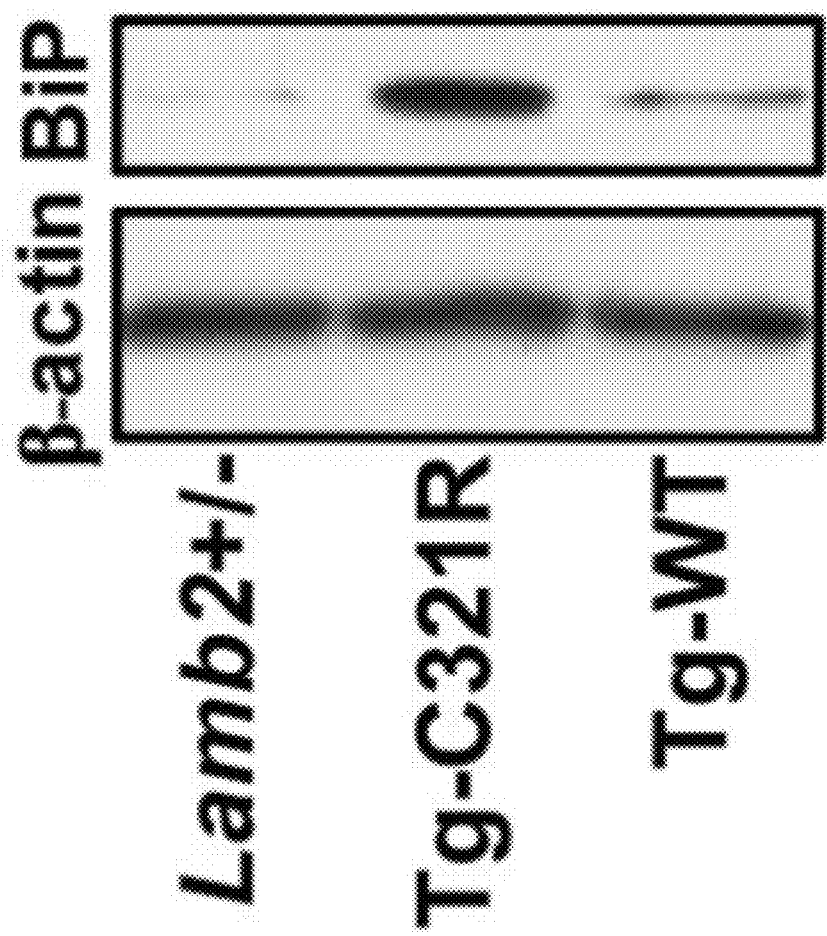
Figure 16:
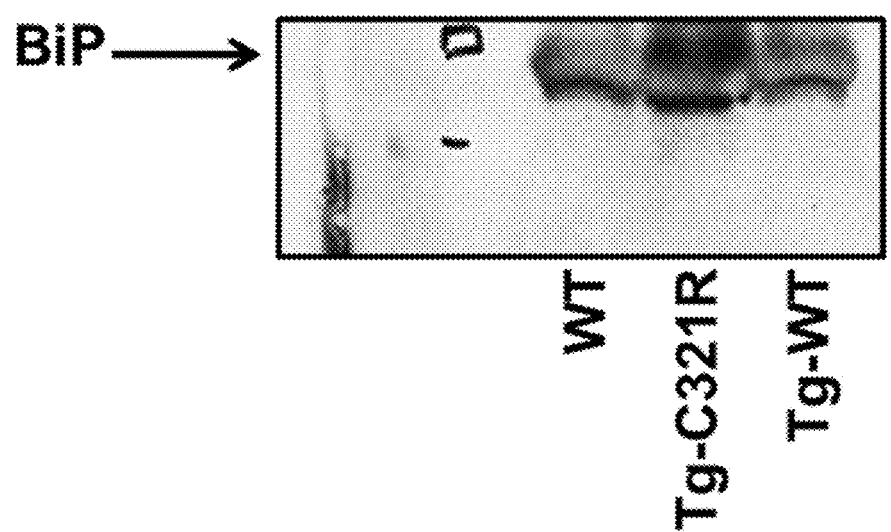
FIG. 16 illustrates that podocyte ER stress increases BiP secretion in vitro.
Figure 17:
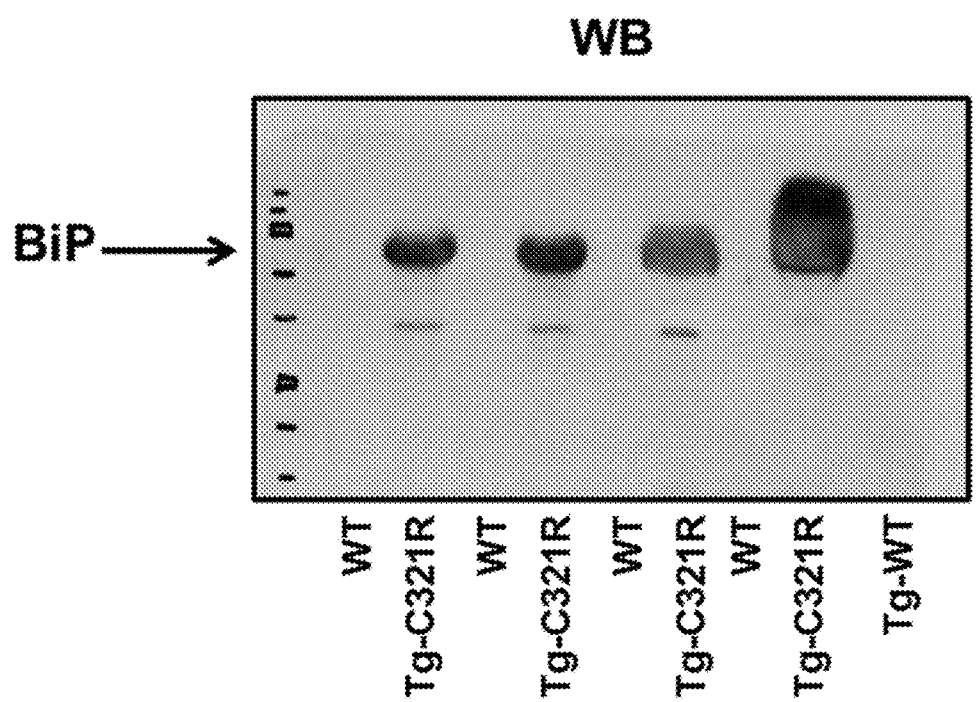
FIG. 17 illustrates that urinary excretion of BiP is detected from the C321R mutant mice in the incipient stage of nephrotic syndrome.

FIG. 15 illustrates that BiP is a urinary biomarker that can be used to detect podocyte ER stress in a podocyte ER stress-induced nephrotic syndrome (NS) mouse model. FIG. 15A shows upregulation of BiP in the podocytes of C321R-LAMB2 transgenic mice compared to BiP expression in the podocytes of control WT-LAMB2 transgenic mice. FIG. 15B shows immunodetection of BiP in glomerular lysates. FIG. 15C shows immunodetection of BiP in primary podocytes. FIG. 16 illustrates immunodetection of secreted BiP in media from stressed podocytes in vitro. FIG. 17 illustrates immunodetection of urinary excretion of BiP from C321R mutant mice at an incipient stage of nephrotic syndrome.

Figure 18:
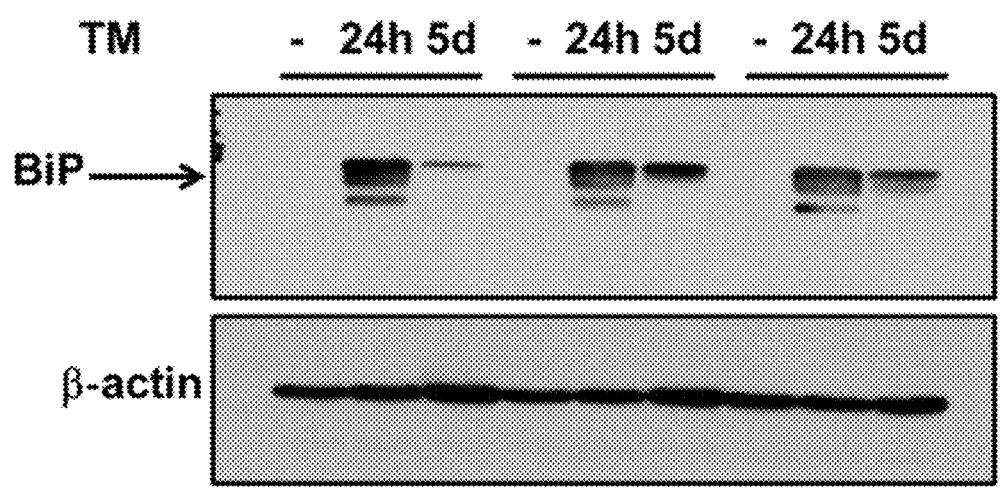
FIG. 18 illustrates that BiP is induced in kidney lysates from TM-injected mice.
Figure 19A:
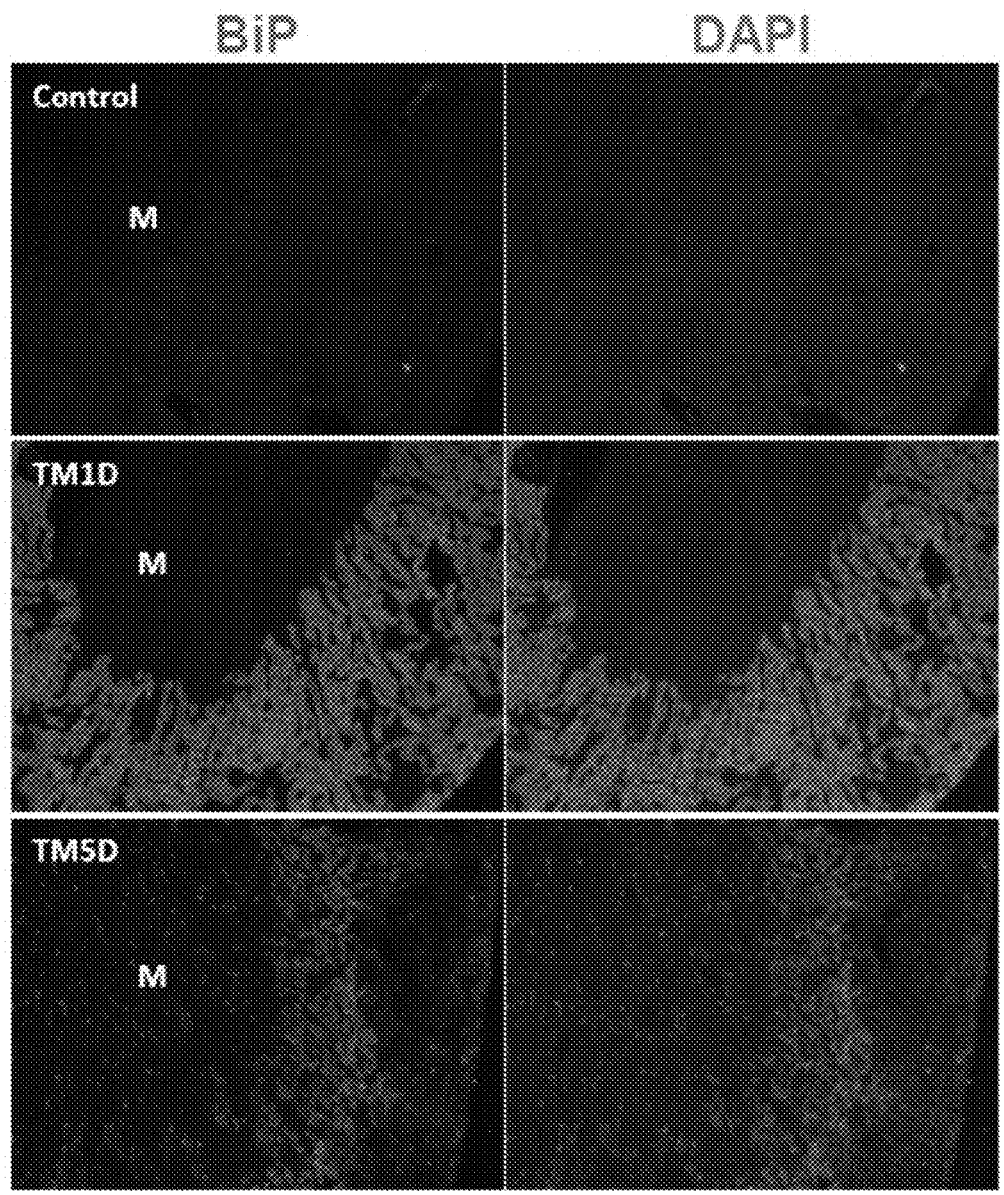
FIG. 19A-FIG. 19B illustrates that BiP is upregulated in the ER stressed-tubular cells at 1 day and 5 days post TM injection, respectively at 4× magnification (FIG. 19A) and at 40× magnification (FIG. 19B).
Figure 19B:
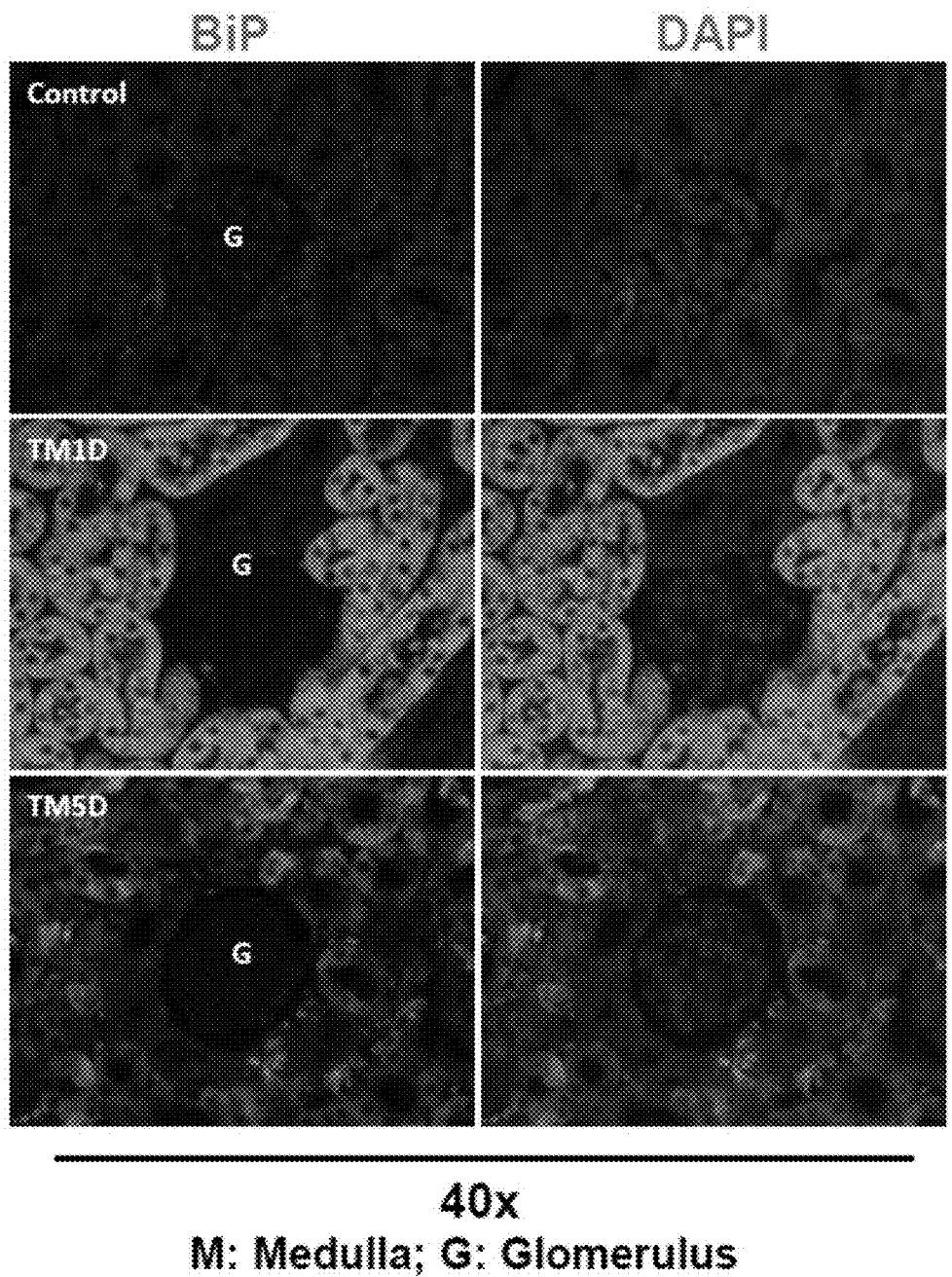
Figure 20:
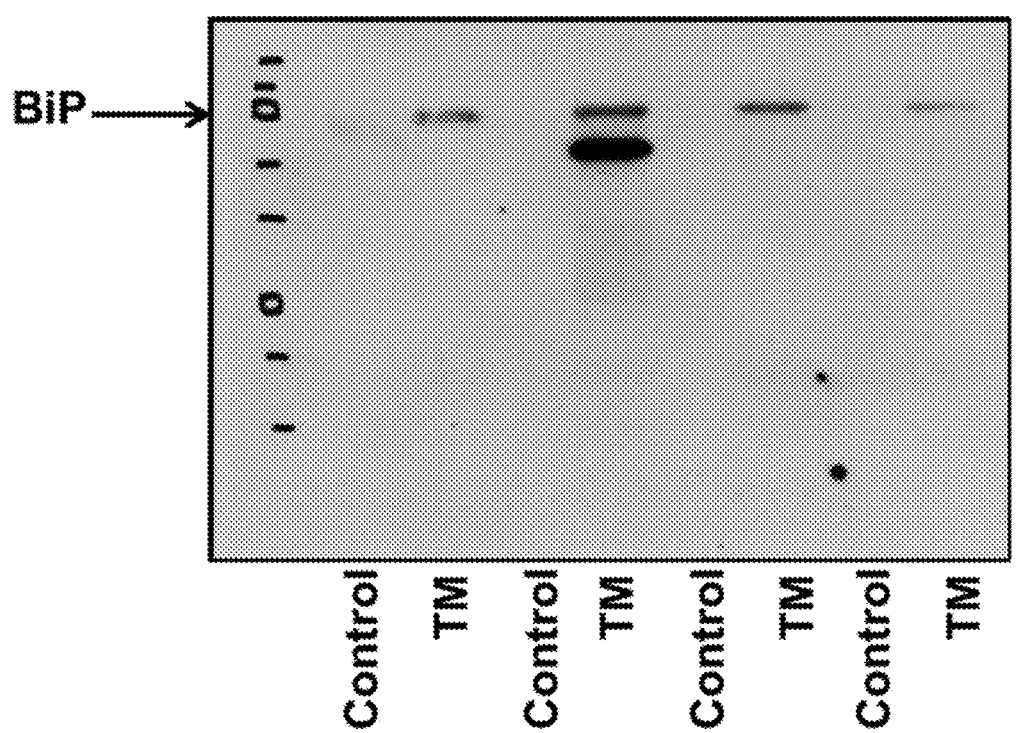
FIG. 20 illustrates that BiP is detected in the urine within 24 hrs from TM-injected mice, when there is no obvious histological changes of kidney injury.

(iii) BiP as a Biomarker for Monitoring Tubular ER Stress in the Tunicamycin (TM)-Induced Acute Kidney Injury (AKI) Mouse Model FIG. 18 illustrates immunodetection of BiP induced in kidney lysates from tunicamycin (TM)-injected mice. FIG. 19 illustrates immunofluorescence detection of BiP and its upregulation in ER stressed-tubular cells at 1 day and 5 days post tunicamycin injection. FIG. 20 illustrates immunodetection of BiP in urine within 24 hr from tunicamycin-injected mice, even when there is no obvious histological indications of kidney injury.

Figure 21A:
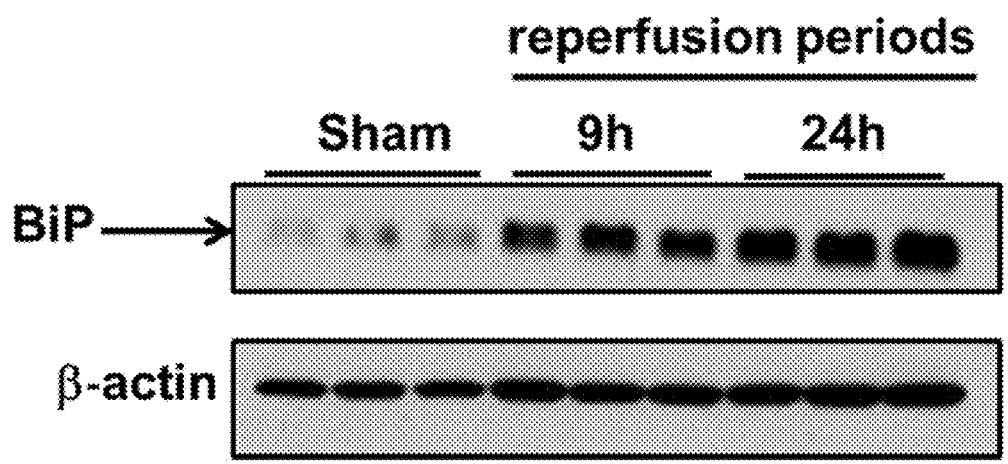
FIG. 21A illustrates that BiP is induced in kidney lysates from I/R-injured mice as early as 9 h after reperfusion.
Figure 21B:
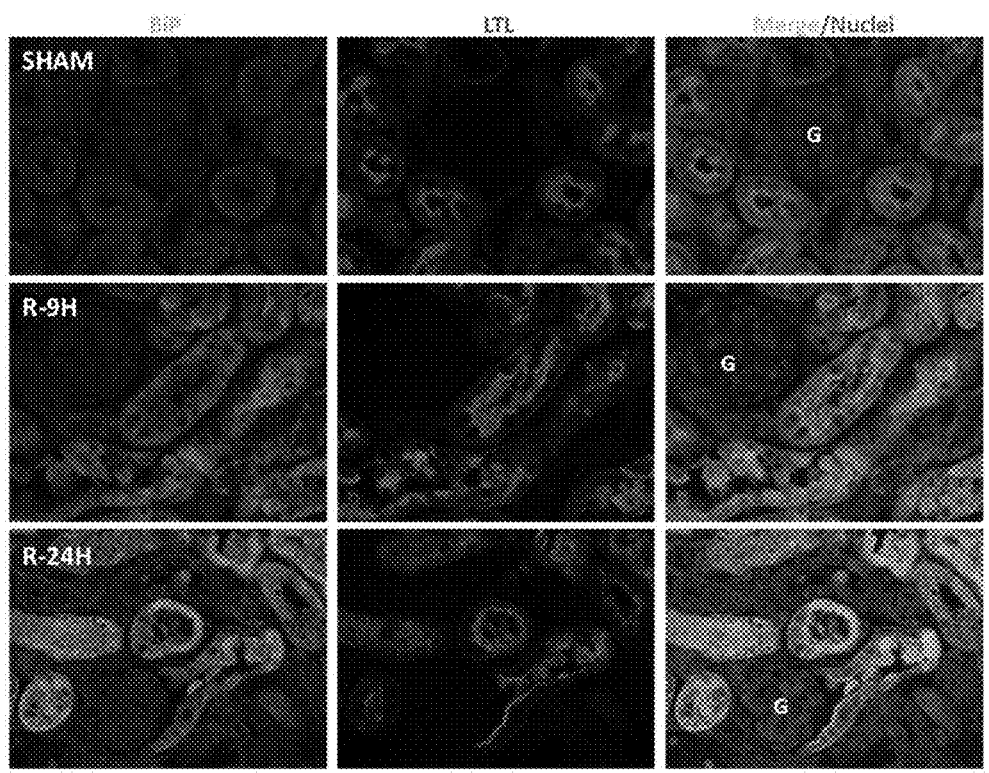
FIG. 21B is a series of images showing, consistent with WB, dual immunofluorescence (IF) staining of sham-operated and post-ischemic kidney sections for BiP and LTL, which is a marker for proximal tubules, demonstrates that significant BiP induction occurs in injured proximal tubular cells at 9 hours and a slight increase at 24 hours after the ischemic injury. In contrast, the glomeruli (G) are devoid of BiP expression.
Figure 22:
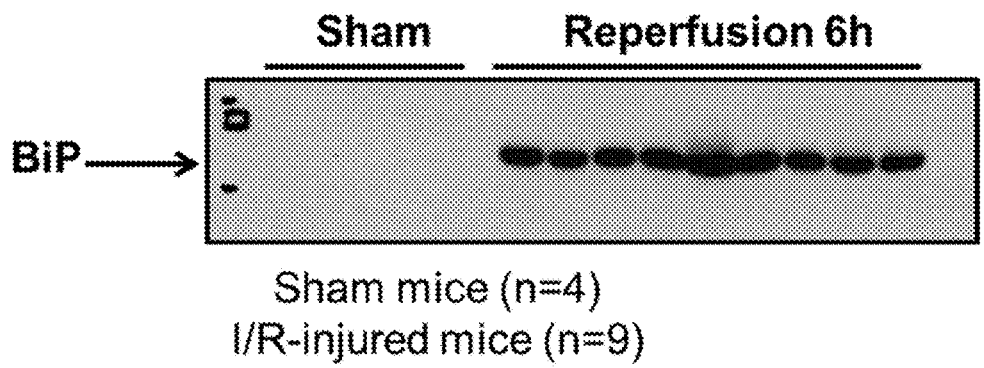
FIG. 22 is an image of a Western blot showing BiP is easily detected in urine specimens within 6 h of reflow from I/R injured mice after bilateral renal ischemia 30 minutes.

(iv) BiP as a Biomarker for ER-Stressed Tubular Cells in the Bilateral Renal Ischemia Acute Kidney Injury (AKI) Model FIG. 21A illustrates BiP is significantly induced in kidney lysates from I/R-injured mice following bilateral renal ischemia 30 minutes at 9 h and 24 h after reperfusion (R). In FIG. 21B, immunofluorescence data confirmed the same conclusion. Most importantly, BiP is easily detected in urine specimens within 6 h reflow from I/R injured mice after bilateral renal ischemia 30 minutes (see e.g., FIG. 22).

Figure 23A:
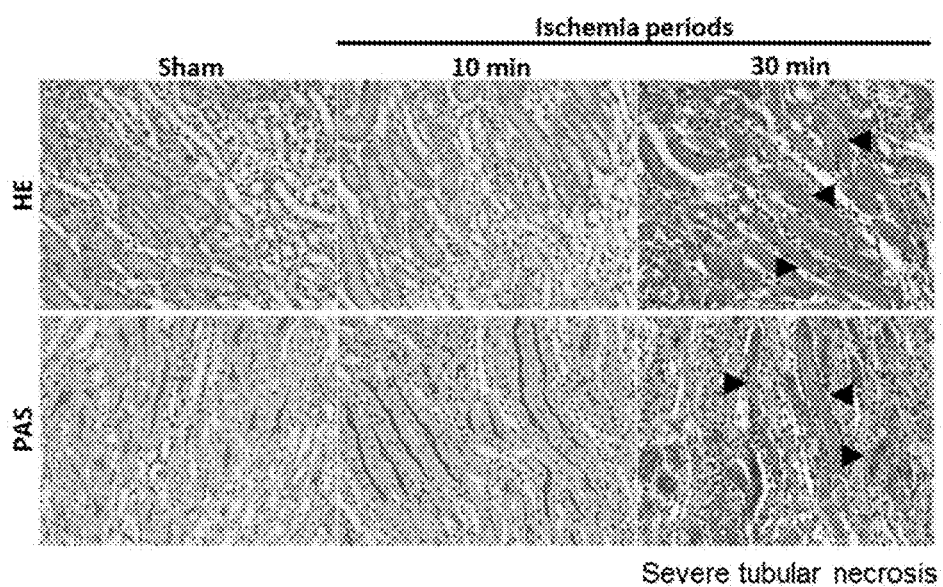
Figure 23B:
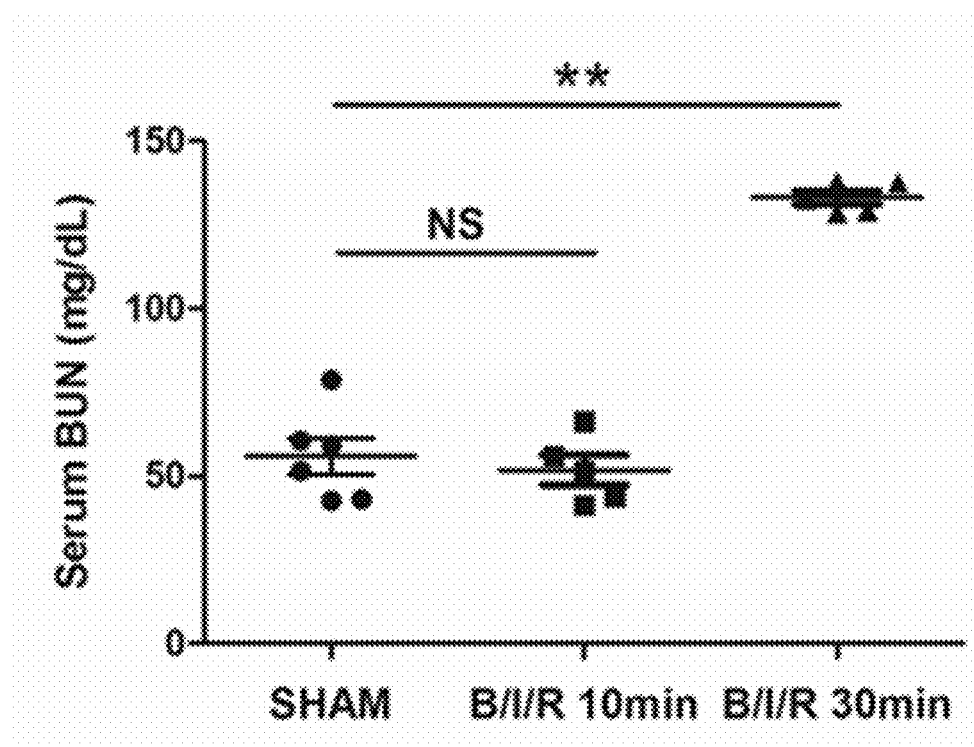
FIG. 23B is a graph of kidney function levels showing, at 24 h of reperfusion, compared with mice with 30 min bilateral ischemia, mice with 10 min bilateral ischemia do not manifest any renal functional changes.
Figure 23C:
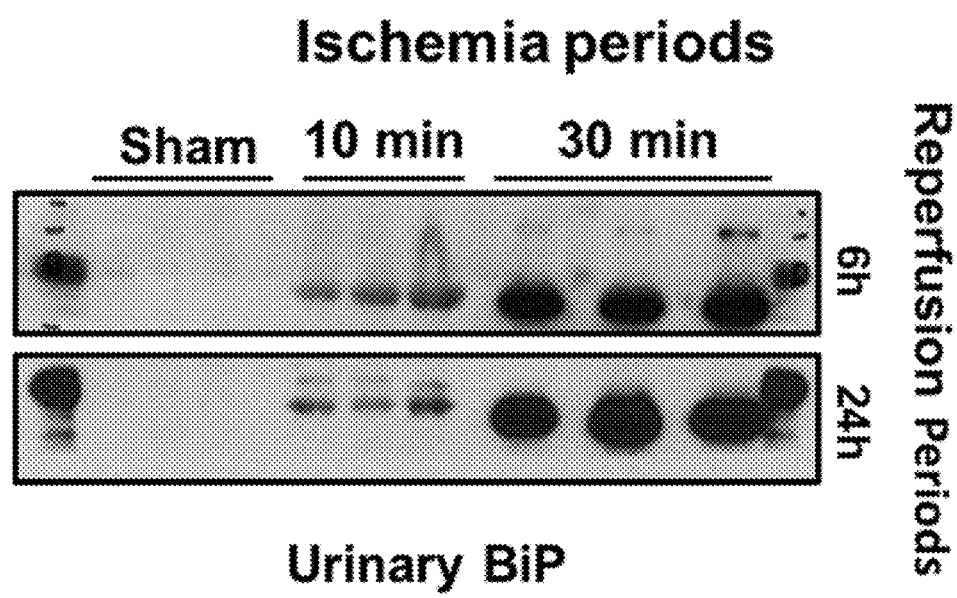
FIG. 23C is an image of a Western blot showing urinary BiP excretion can be detected in subclinical AKI caused by tubular ER stress and urinary BiP levels are correlated with the AKI severity.

To investigate whether BiP can be used to detect tubular ER stress in the absence of renal histopathological changes or kidney function declining, and whether urinary BiP excretion correlates with the disease severity, a subclinical AKI model following bilateral renal ischemia 10 min was also utilized. At 24 h of reperfusion, compared with mice with 30 min bilateral ischemia, mice with 10 min bilateral ischemia do not manifest any histological or renal functional changes (see e.g., FIGS. 23A and 23B). Urinary BiP excretion was detected in subclinical AKI caused by tubular ER stress and urinary BiP levels are correlated with the AKI severity (see e.g., FIG. 23C).

(v) BiP Levels are Markedly Increased in Autosomal Dominant Tubulointerstitial Kidney Disease (ADTKD)

ADTKD is a monogenic form of renal tubulointerstitial fibrosis characterized by hyperuricemia, gout, alterations in urinary concentration, and progressive loss of kidney function. ADTKD can represent as many as 25% of patients with inherited kidney disease, after exclusion of polycystic kidney disease and Alport syndrome. ADTKD caused by uromodulin (UMOD) mutations is a prototypical tubular ER stress disease.

Figure 25:
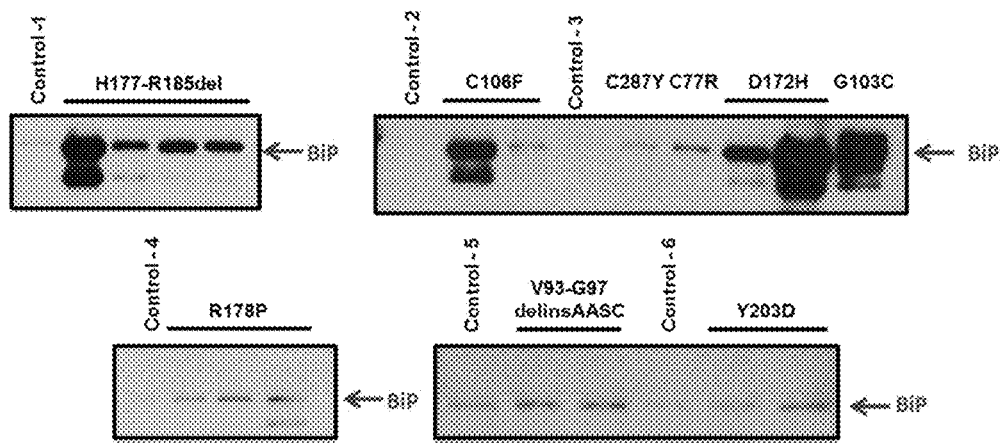
FIG. 25 is a series of Western blots showing the superb ability of BiP to discriminate between controls and ADTKD patients caused by UMOD mutations with tubular ER stress.

Urinary BiP levels are markedly increased in ADTKD patients caused by a variety of mutations in UMOD, whereas urinary BiP excretion is absent from all tested genetically unaffected family members (controls). In addition, BiP excretion is observed in the urine of a number of patients with normal or mildly impaired renal function (glomerular filtration rate above 60 ml/min) (see e.g., FIG. 25).

These results (see e.g., FIG. 25) demonstrate the superb ability of BiP to discriminate between controls and ADTKD patients with tubular ER stress. Moreover, urinary excretion of BiP may enable identification of disease activity early in the course of disease and allow for the monitoring of the effects of therapy, overcoming the challenge posed by the slow rise in serum creatinine, a current marker of renal function, in these individuals, which is the major reason that currently clinical trials in ADTKD-UMOD cannot be performed.

(vi) Human Pediatric AKI Patients after Cardiopulmonary Bypass Surgery

This example describes two groups of patients studied after cardiac surgery studied: no AKI and severe AKI patients.

AKI is a frequent complication of pediatric cardiac surgery and negatively effects short- and long-term outcomes. Despite decades of research, no therapy has proven effective for the prevention or treatment of human AKI. Serum creatinine, the traditional marker of renal function, only rises appreciably after a 50% loss in kidney function. Serum creatinine is also affected by several nonrenal factors and on average does not peak until 2 days after cardiac surgery. Severe AKI is defined by either receipt of acute dialysis or postoperative doubling of serum creatinine during hospital stay.

Figure 26:
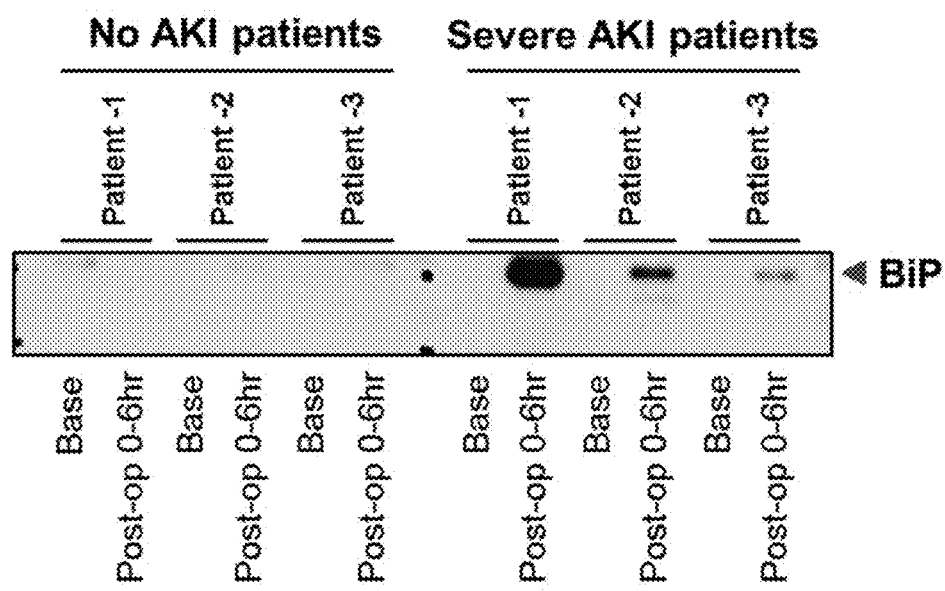
FIG. 26 is an image of a Western blot showing urinary BiP excretion is detected at early as post-op 0-6 hours in the severe AKI group of pediatric patients following cardiac surgery, whereas BiP excretion is not detected in the urine of no AKI group following the cardiac surgery.

Urinary BiP excretion was detected as early as post-op 0-6 hours in the severe AKI group, whereas BiP excretion is not detected in the urine of no AKI group following the cardiac surgery (see e.g., FIG. 26). This demonstrates that urinary BiP excretion can be used as an early ER stress biomarker to predict who will develop AKI later, which is critical to institute early therapeutic intervention.

(vii) Summary

In conclusion, BiP has been discovered to be secreted in response to ER stress. Furthermore, this example has shown that BiP is induced in ER-stressed podocytes and renal tubular cells, respectively, and excreted in the urine at very early stage of diseases, preceding renal histological or functional changes. It was shown that urinary BiP excretion has been detected in human DN patients associated with podocyte ER stress and in human ADTKD and AKI patients caused by tubular ER stress in the early stage of the disease. In addition, urinary BiP excretion levels correlate with the disease severity and can predict the disease outcome.

These findings have important diagnostic and prognostic values as a mechanistic biomarker. It also aids in early identification of individuals at risk for disease progression and for following the treatment response. There will be broad clinical uses of BiP as a urine biomarker for ER stress-mediated kidney diseases including, but not limited to, congenital nephrotic syndrome (CNS), focal segmental glomerulosclerosis (FSGS), and Alport syndrome caused by different podocyte gene mutations, ADTKD, or acute kidney injury, etc.

Thus, BiP can serve as a urine diagnostic or prognostic biomarker in ER stress-related kidney diseases to help stratify disease risk, predict disease progression, monitor treatment response, and identify subgroups of patients who can be treated with ER stress modulators in a highly targeted manner. Based on the presently disclosed results, there can be extensive clinical use of BiP as a urine biomarker for ER-stress-related kidney diseases including hereditary proteinuric diseases caused by different podocyte gene mutations, familial and non-familial forms of focal segmental glomerulosclerosis, Alport syndrome, membranous nephropathy, acute kidney injury, and medullary cystic kidney disease.

REFERENCES

1. Inagi, R., Ishimoto, Y., and Nangaku, M. 2014. Proteostasis in endoplasmic reticulum—new mechanisms in kidney disease. Nat Rev Nephrol 10:369-378.
2. Ron, D., and Walter, P. 2007. Signal integration in the endoplasmic reticulum unfolded protein response. Nat Rev Mol Cell Biol 8:519-529.
3. Hinkes, B. G., Mucha, B., Vlangos, C. N., Gbadegesin, R., Liu, J., Hasselbacher, K., Hangan, D., Ozaltin, F., Zenker, M., and Hildebrandt, F. 2007. Nephrotic syndrome in the first year of life: two thirds of cases are caused by mutations in 4 genes (NPHS1, NPHS2, WT1, and LAMB2). Pediatrics 119:e907-919.
4. Gast, C., Pengelly, R. J., Lyon, M., Bunyan, D. J., Seaby, E. G., Graham, N., Venkat-Raman, G., and Ennis, S. 2015. Collagen (COL4A) mutations are the most frequent mutations underlying adult focal segmental glomerulosclerosis. Nephrol Dial Transplant.
5. Chen, Y. M., Zhou, Y., Go, G., Marmerstein, J. T., Kikkawa, Y., and Miner, J. H. 2013. Laminin beta2 gene missense mutation produces endoplasmic reticulum stress in podocytes. J Am Soc Nephrol 24:1223-1233.
6. Pieri, M., Stefanou, C., Zaravinos, A., Erguler, K., Stylianou, K., Lapathitis, G., Karaiskos, C., Sawa, I., Paraskeva, R., Dweep, H., et al. 2014. Evidence for Activation of the Unfolded Protein Response in Collagen IV Nephropathies. J Am Soc Nephrol 25:260-275.
7. Cybulsky, A. V., Takano, T., Papillon, J., and Bijian, K. 2005. Role of the endoplasmic reticulum unfolded protein response in glomerular epithelial cell injury. J Biol Chem 280:24396-24403.
8. Cybulsky, A. V., Takano, T., Papillon, J., Khadir, A., Liu, J., and Peng, H. 2002. Complement C5b-9 membrane attack complex increases expression of endoplasmic reticulum stress proteins in glomerular epithelial cells. J Biol Chem 277:41342-41351.

9. Inoki, K., Mori, H., Wang, J., Suzuki, T., Hong, S., Yoshida, S., Blattner, S. M., Ikenoue, T., Ruegg, M. A., Hall, M. N., et al. 2011. mTORC1 activation in podocytes is a critical step in the development of diabetic nephropathy in mice. J Clin Invest 121:2181-2196.
10. Bek, M. F., Bayer, M., Muller, B., Greiber, S., Lang, D., Schwab, A., August, C., Springer, E., Rohrbach, R., Huber, T. B., et al. 2006. Expression and function of C/EBP homology protein (GADD153) in podocytes. Am J Pathol 168:20-32.
11. Markan, S., Kohli, H. S., Joshi, K., Minz, R. W., Sud, K., Ahuja, M., Anand, S., and Khullar, M. 2009. Up regulation of the GRP-78 and GADD-153 and down regulation of Bcl-2 proteins in primary glomerular diseases: a possible involvement of the ER stress pathway in glomerulonephritis. Mol Cell Biochem 324:131-138.
12. Eckardt, K. U., Alper, S. L., Antignac, C., Bleyer, A. J., Chauveau, D., Dahan, K., Deltas, C., Hosking, A., Kmoch, S., Rampoldi, L., et al. 2015. Autosomal dominant tubulointerstitial kidney disease: diagnosis, classification, and management-A KDIGO consensus report. Kidney International 88:676-683.
13. Rampoldi, L., Scolari, F., Amoroso, A., Ghiggeri, G., and Devuyst, O. 2011. The rediscovery of uromodulin (Tamm-Horsfall protein): from tubulointerstitial nephropathy to chronic kidney disease. Kidney International 80:338-347.
14. Bernascone, I., Janas, S., Ikehata, M., Trudu, M., Corbelli, A., Schaeffer, C., Rastaldi, M. P., Devuyst, O., and Rampoldi, L. 2010. A transgenic mouse model for uromodulin-associated kidney diseases shows specific tubulointerstitial damage, urinary concentrating defect and renal failure. Human Molecular Genetics 19:2998-3010.
15. Bernascone, I., Vavassori, S., Di Pentima, A., Santambrogio, S., Lamorte, G., Amoroso, A., Scolari, F., Ghiggeri, G. M., Casari, G., Polishchuk, R., et al. 2006. Defective intracellular trafficking of uromodulin mutant isoforms. Traffic 7:1567-1579.
16. Kemter, E., Prueckl, P., Sklenak, S., Rathkolb, B., Habermann, F. A., Hans, W., Gailus-Durner, V., Fuchs, H., de Angelis, M. H., Wolf, E., et al. 2013. Type of uromodulin mutation and allelic status influence onset and severity of uromodulin-associated kidney disease in mice. Human Molecular Genetics 22:4148-4163.
17. Rampoldi, L., Caridi, G., Santon, D., Boaretto, F., Bernascone, I., Lamorte, G., Tardanico, R., Dagnino, M., Colussi, G., Scolari, F., et al. 2003. Allelism of MCKD, FJHN and GCKD caused by impairment of uromodulin export dynamics. Human Molecular Genetics 12:3369-3384.
18. Vylet'al, P., Kublova, M., Kalbacova, M., Hodanova, K., Baresova, V., Stiburkova, B., Sikora, J., Hulkova, H., Zivny, J., Majewski, J., et al. 2006. Alterations of uromodulin biology: A common denominator of the genetically heterogeneous FJHN/MCKD syndrome. Kidney International 70:1155-1169.
19. Bando, Y., Tsukamoto, Y., Katayama, T., Ozawa, K., Kitao, Y., Hori, O., Stern, D. M., Yamauchi, A., and Ogawa, S. 2004. ORP150/HSP12A protects renal tubular epithelium from ischemia-induced cell death. FASEB J 18:1401-1403.
20. El Karoui, K., Viau, A., Dellis, O., Bagattin, A., Nguyen, C., Baron, W., Burtin, M., Broueilh, M., Heidet, L., Mollet, G., et al. 2016. Endoplasmic reticulum stress drives proteinuria-induced kidney lesions via Lipocalin 2. Nature Communications 7.
21. Kim, Y., Lee, H., Manson, S. R., Lindahl, M., Evans, B., Miner, J. H., Urano, F., and Chen, Y. M. 2016. Mesencephalic Astrocyte-Derived Neurotrophic Factor as a Urine Biomarker for Endoplasmic Reticulum Stress-Related Kidney Diseases. Journal of the American Society of Nephrology: JASN 27:2974-2982.
22. Oh-hashi, K., Koga, H., Ikeda, S., Shimada, K., Hirata, Y., and Kiuchi, K. 2009. CRELD2 is a novel endoplasmic reticulum stress-inducible gene. Biochem Biophys Res Commun 387:504-510.
23. Oh-hashi, K., Kunieda, R., Hirata, Y., and Kiuchi, K. 2011. Biosynthesis and secretion of mouse cysteine-rich with EGF-like domains 2. FEBS letters 585:2481-2487.
24. Oh-hashi, K., Norisada, J., Hirata, Y., and Kiuchi, K. 2015. Characterization of the Role of MANF in Regulating the Secretion of CRELD2. Biological & Pharmaceutical Bulletin 38:722-731.
25. Hartley, C. L., Edwards, S., Mullan, L., Bell, P. A., Fresquet, M., Boot-Handford, R. P., and Briggs, M. D. 2013. Armet/Manf and Creld2 are components of a specialized ER stress response provoked by inappropriate formation of disulphide bonds: implications for genetic skeletal diseases. Human Molecular Genetics 22:5262-5275.
26. Olden, K., Pratt, R. M., Jaworski, C., and Yamada, K. M. 1979. Evidence for role of glycoprotein carbohydrates in membrane transport: specific inhibition by tunicamycin. Proceedings of the National Academy of Sciences of the United States of America 76:791-795.
27. Thastrup, O., Cullen, P. J., Drobak, B. K., Hanley, M. R., and Dawson, A. P. 1990. Thapsigargin, a tumor promoter, discharges intracellular Ca2+ stores by specific inhibition of the endoplasmic reticulum Ca2(+)-ATPase. Proceedings of the National Academy of Sciences of the United States of America 87:2466-2470.
28. Miner, J. H., Go, G., Cunningham, J., Patton, B. L., and Jarad, G. 2006. Transgenic isolation of skeletal muscle and kidney defects in laminin beta2 mutant mice: implications for Pierson syndrome. Development 133:967-975.
29. Zinszner, H., Kuroda, M., Wang, X., Batchvarova, N., Lightfoot, R. T., Remotti, H., Stevens, J. L., and Ron, D. 1998. CHOP is implicated in programmed cell death in response to impaired function of the endoplasmic reticulum. Genes Dev 12:982-995.
30. Dong, B., Zhou, H., Han, C., Yao, J., Xu, L., Zhang, M., Fu, Y., and Xia, Q. 2014. Ischemia/reperfusion-induced CHOP expression promotes apoptosis and impairs renal function recovery: the role of acidosis and GPR4. PLoS One 9:e110944.
31. Yang, J. R., Yao, F. H., Zhang, J. G., Ji, Z. Y., Li, K. L., Zhan, J., Tong, Y. N., Lin, L. R., and He, Y. N. 2014. Ischemia-reperfusion induces renal tubule pyroptosis via the CHOP-caspase-11 pathway. Am J Physiol Renal Physiol 306:F75-84.
32. Madhusudhan, T., Wang, H. J., Dong, W., Ghosh, S., Bock, F., Thangapandi, V. R., Ranjan, S., Wolter, J., Kohli, S., Shahzad, K., et al. 2015. Defective podocyte insulin signalling through p85-XBP1 promotes ATF6-dependent maladaptive ER-stress response in diabetic nephropathy. Nature Communications 6.
33. Tervaert, T. W. C., Mooyaart, A. L., Amann, K., Cohen, A. H., Cook, H. T., Drachenberg, C. B., Ferrario, F., Fogo, A. B., Haas, M., de Heer, E., et al. 2010. Pathologic Classification of Diabetic Nephropathy. Journal of the American Society of Nephrology 21:556-563.

34. Li, P. K. T., Burdmann, E. A., Mehta, R. L., and Comm, W. K. D. S. 2013. Acute kidney injury: global health alert. Kidney International 83:372-376.
35. Himmelfarb, J., and Ikizler, T. A. 2007. Acute kidney injury: changing lexicography, definitions, and epidemiology. Kidney International 71:971-976.
36. Singbartl, K., and Kellum, J. A. 2012. AKI in the ICU: definition, epidemiology, risk stratification, and outcomes. Kidney International 81:819-825.
37. Bydash, J. R., and Ishani, A. 2011. Acute Kidney Injury and Chronic Kidney Disease: A Work in Progress. Clinical Journal of the American Society of Nephrology 6:2555-2557.
38. Siew, E. D., Ware, L. B., and Ikizler, T. A. 2011. Biological Markers of Acute Kidney Injury. Journal of the American Society of Nephrology 22:810-820.
39. Lovric, S., Ashraf, S., Tan, W., and Hildebrandt, F. 2015. Genetic testing in steroid-resistant nephrotic syndrome: when and how? Nephrology, dialysis, transplantation: official publication of the European Dialysis and Transplant Association—European Renal Association.
40. Sampson, M. G., Gillies, C. E., Robertson, C. C., Crawford, B., Vega-Warner, V., Otto, E. A., Kretzler, M., and Kang, H. M. 2015. Using Population Genetics to Interrogate the Monogenic Nephrotic Syndrome Diagnosis in a Case Cohort. Journal of the American Society of Nephrology: JASN.
41. Trautmann, A., Bodria, M., Ozaltin, F., Gheisari, A., Melk, A., Azocar, M., Anarat, A., Caliskan, S., Emma, F., Gellermann, J., et al. 2015. Spectrum of steroid-resistant and congenital nephrotic syndrome in children: the PodoNet registry cohort. Clinical journal of the American Society of Nephrology: CJASN 10:592-600.
42. Sampson, M. G., and Pollak, M. R. 2015. Opportunities and Challenges of Genotyping Patients With Nephrotic Syndrome in the Genomic Era. Seminars in nephrology 35:212-221.
43. Gillies, C. E., Robertson, C. C., Sampson, M. G., and Kang, H. M. 2015. GeneVetter: a web tool for quantitative monogenic assessment of rare diseases. Bioinformatics 31:3682-3684.
44. Grimm, D. G., Azencott, C. A., Aicheler, F., Gieraths, U., MacArthur, D. G., Samocha, K. E., Cooper, D. N., Stenson, P. D., Daly, M. J., Smoller, J. W., et al. 2015. The evaluation of tools used to predict the impact of missense variants is hindered by two types of circularity. Human mutation 36:513-523.
45. Pennica, D., Kohr, W. J., Kuang, W. J., Glaister, D., Aggarwal, B. B., Chen, E. Y., and Goeddel, D. V. 1987. Identification of Human Uromodulin as the Tamm-Horsfall Urinary Glycoprotein. Science 236:83-88.
46. Brunati, M., Perucca, S., Han, L., Cattaneo, A., Consolato, F., Andolfo, A., Schaeffer, C., Olinger, E., Peng, J. H., Santambrogio, S., et al. 2015. The serine protease hepsin mediates urinary secretion and polymerisation of Zona Pellucida domain protein uromodulin. Elife 4.
47. Schaeffer, C., Creatore, A., and Rampoldi, L. 2014. Protein trafficking defects in inherited kidney diseases. Nephrology Dialysis Transplantation 29:33-44.

What is claimed is:

1. A method of detecting an endoplasmic reticulum (ER) stress-associated kidney disease in a subject, comprising:
providing a biological sample from a subject suspected of having an endoplasmic reticulum (ER) stress-associated kidney disease;
centrifuging the biological sample;
contacting the biological sample with at least one antibody that binds an ER stress biomarker under conditions sufficient for formation of a primary complex comprising the at least one antibody and the ER stress biomarker comprising Cysteine-rich with EGF-like domain protein 2 (CRELD2) or Immunoglobulin binding protein (BiP) if present;
measuring a quantity of the primary complex;
comparing the quantity of the primary complex to a quantity of a control complex formed from the at least one antibody and a biological sample of an individual who does not have an endoplasmic reticulum (ER) stress-associated kidney disease; and
detecting an endoplasmic reticulum (ER) stress-associated kidney disease if the primary complex comprises the ER stress biomarker comprising CRELD2 or BiP at a statistically significant elevated level compared to the control complex,
wherein,
the subject is a human or a mouse;
the endoplasmic reticulum (ER) stress-associated kidney disease is a podocyte ER stress-induced kidney disease or a tubular ER stress-induced kidney disease;
the biological sample is urine; and
the centrifuging concentrates urine proteins in the biological sample.

2. The method of claim 1, wherein the ER stress biomarker consists of BiP or CRELD2.

3. The method of claim 1, wherein the ER associated kidney disease, disorder, or condition is selected from one or more of the group consisting of advanced diabetic glomerulosclerosis, autosomal dominant tubulointerstitial kidney disease (ADTKD), acute kidney injury (AKI), acute renal failure, Alport syndrome, chronic kidney disease associated with a kidney disease-risk allele, congenital nephrotic syndrome (CNS), diabetic nephropathy (DN), focal segmental glomerulosclerosis (FSGS), genetic mutations of renal proteins, hereditary nephritis, hereditary proteinuric disease, ischemia-reperfusion-induced acute kidney injury, kidney disease associated with missense mutations in nephrin or podocin, kidney disease associated with underglycosylation of nephrin, membranous nephropathy, minimal change disease (MCD), nephrotic syndrome (NS), protein overload, puromycin aminonucleoside nephrosis (PAN), renal fibrosis, tunicamycin-induced acute kidney injury or proteinuria, or polycystic kidney disease.

4. The method of claim 1, wherein the method is performed before significant proteinuria or glomerulosclerosis develops.

5. The method of claim 1, further comprising identifying a subject with a high risk for development or progression of proteinuria or renal function deterioration if CRELD2 or BiP levels are statistically significantly elevated compared to a control.

6. The method of claim 1, wherein the at least one antibody is a monoclonal antibody.

7. The method of claim 1, wherein the at least one antibody is a polyclonal antibody.

8. The method of claim 1, wherein the detecting comprises an immunoprecipitation assay, an ELISA, a radioimmunoassay, a Western blot assay, a dip stick assay, or a bead assay.

9. The method of claim 1, wherein the contacting comprises:

a) contacting the biological sample with a solid surface that binds the ER stress biomarker selected from CRELD2 or BiP if present; and b) subsequent to a), contacting the solid surface with the at least one antibody.

10. The method of claim 9, wherein the ER stress biomarker consists essentially of BiP and CRELD2.

11. The method of claim 1, wherein the at least one antibody is bound to a polystyrene bead.

12. The method of claim 1, further comprising:
contacting a control biological sample from a person not suspected of having an endoplasmic reticulum (ER) stress-associated kidney disease with the at least one antibody that binds CRELD2 or BiP under conditions sufficient for formation of a control complex comprising the at least one antibody and CRELD2 or BiP if present; and
measuring the quantity of the control complex.

13. The method of claim 1, wherein the detecting comprises a Western blot assay or an ELISA.

14. The method of claim 1, wherein the ER stress-associated kidney disease is a hereditary proteinuric disease, human diabetic neuropathy, nephrotic syndrome (NS), acute kidney injury after bypass surgery, or autosomal dominant tubulointerstitial kidney disease (ADTKD).

15. The method of claim 1, wherein the ER stress-associated kidney disease is glomerulosclerosis.

16. The method of claim 15, wherein the glomerulosclerosis is a focal segmental glomerulosclerosis, a familial form of focal segmental glomerulosclerosis, a non-familial form of focal segmental glomerulosclerosis, nodular glomerular sclerosis, or advanced diabetic glomerulosclerosis.

17. The method of claim 1, wherein the ER stress-associated kidney disease is Alport syndrome, membranous nephropathy, acute kidney injury, congenital nephrotic syndrome (CNS), nephrotic syndrome, minimal change disease, human diabetic nephropathy (DN), medullary cystic kidney disease, or polycystic kidney disease.

18. The method of claim 1, wherein the ER stress biomarker is detected
after a suspected kidney injury;
after cardiopulmonary bypass surgery;
after treatment of an ER stress associated kidney disease to monitor treatment response or kidney condition or recovery;
before diagnosis of an ER associated kidney disease for early detection or risk determination;
within 30 minutes, 3 hours, 9 hours, or 24 hours after a suspected kidney injury; or
between 0 and 6 hours, between 0 and 9 hours, or up to 2 days after cardiopulmonary bypass surgery.

19. A method of treating an endoplasmic reticulum (ER) stress-associated kidney disease in a subject, comprising:
providing a biological sample from a subject suspected of having an endoplasmic reticulum (ER) stress-associated kidney disease;
centrifuging the biological sample;
contacting the biological sample with at least one antibody that binds an ER stress biomarker under conditions sufficient for formation of a primary complex comprising the at least one antibody and the ER stress biomarker comprising Cysteine-rich with EGF-like domain protein 2 (CRELD2) or Immunoglobulin binding protein (BiP) if present;
measuring a quantity of the primary complex;
comparing the quantity of the primary complex to a quantity of a control complex formed from the at least one antibody and a biological sample of an individual who does not have an endoplasmic reticulum (ER) stress-associated kidney disease;
detecting an endoplasmic reticulum (ER) stress-associated kidney disease if the primary complex comprises the ER stress biomarker comprising (CRELD2 or BiP at a statistically significant elevated level compared to the control complex; and
treating the subject by (i) administering a therapeutically effective amount of a pharmaceutical agent suitable for treatment of an ER stress associated disease or (ii) administering a therapeutic method suitable for treatment of an ER stress associated disease,
wherein,
the subject is a human or a mouse;
the endoplasmic reticulum (ER) stress-associated kidney disease is a podocyte ER stress-induced kidney disease or a tubular ER stress-induced kidney disease;
the biological sample is urine; and
the centrifuging concentrates urine proteins in the biological sample.

20. The method of claim 1, wherein the ER stress biomarker comprises CRELD2.

21. The method of claim 1, wherein the detecting is performed using an ELISA.

* * * * *

SEQUENCE LISTING

```
<160> NUMBER OF SEQ ID NOS: 6

<210> SEQ ID NO 1
<211> LENGTH: 21
<212> TYPE: DNA
<213> ORGANISM: Artificial Sequence
<220> FEATURE:
<223> OTHER INFORMATION: synthetic primer

<400> SEQUENCE: 1
caacacggcc aggaagaatt t                                             21

<210> SEQ ID NO 2
<211> LENGTH: 21
<212> TYPE: DNA
<213> ORGANISM: Artificial Sequence
<220> FEATURE:
<223> OTHER INFORMATION: synthetic primer

<400> SEQUENCE: 2
catgatctcc agaagccgga t                                             21

<210> SEQ ID NO 3
<211> LENGTH: 19
<212> TYPE: DNA
<213> ORGANISM: Artificial Sequence
<220> FEATURE:
<223> OTHER INFORMATION: synthetic primer

<400> SEQUENCE: 3
gagagccagc ctaccatcc                                                19

<210> SEQ ID NO 4
<211> LENGTH: 21
```

```
<212> TYPE: DNA
<213> ORGANISM: Artificial Sequence
<220> FEATURE:
<223> OTHER INFORMATION: synthetic primer

<400> SEQUENCE: 4
gggtcctcgt gtttgaagga a                                              21

<210> SEQ ID NO 5
<211> LENGTH: 23
<212> TYPE: DNA
<213> ORGANISM: Artificial Sequence
<220> FEATURE:
<223> OTHER INFORMATION: synthetic primer

<400> SEQUENCE: 5
tgtagaccat gtagttgagg tca                                            23

<210> SEQ ID NO 6
<211> LENGTH: 21
<212> TYPE: DNA
<213> ORGANISM: Artificial Sequence
<220> FEATURE:
<223> OTHER INFORMATION: synthetic primer

<400> SEQUENCE: 6
aggtcggtgt gaacggattt g                                              21
```